(12) United States Patent
Tam et al.

(10) Patent No.: US 8,980,555 B2
(45) Date of Patent: Mar. 17, 2015

(54) RAPID GENOTYPING ANALYSIS AND DEVICES THEREOF

(71) Applicant: Diagcor Bioscience Incorporation Limited, Kowloon Bay (CN)

(72) Inventors: Joseph Wing On Tam, Daly City, CA (US); Joseph Kwok Fai Chow, Hong Kong (CN); Xiumei Guo, Hong Kong (CN); Wendy Wing Shan Yeung, Hong Kong (CN); Lai On Chu, Hong Kong (CN)

(73) Assignee: Diagcor Bioscience Incorporation Limited, Hong Kong (CN)

( * ) Notice: Subject to any disclaimer, the term of this patent is extended or adjusted under 35 U.S.C. 154(b) by 0 days.

(21) Appl. No.: 13/839,067

(22) Filed: Mar. 15, 2013

(65) Prior Publication Data

US 2013/0244887 A1 Sep. 19, 2013

Related U.S. Application Data

(63) Continuation-in-part of application No. 12/770,034, filed on Apr. 29, 2010.

(51) Int. Cl.
*C12Q 1/68* (2006.01)
*C12P 19/34* (2006.01)
*C12Q 1/70* (2006.01)

(52) U.S. Cl.
CPC .............. *C12Q 1/689* (2013.01); *C12Q 1/6888* (2013.01); *C12Q 1/6883* (2013.01); *C12Q 1/708* (2013.01); *C12Q 1/705* (2013.01); *C12Q 1/706* (2013.01); *C12Q 2600/156* (2013.01)
USPC .......................................... 435/6.1; 435/91.2

(58) Field of Classification Search
CPC .... C12Q 1/6888; C12Q 1/6883; C12Q 1/689; C12Q 260/156; G01N 2800/52
See application file for complete search history.

(56) References Cited

U.S. PATENT DOCUMENTS

| | | | |
|---|---|---|---|
| 5,310,650 A | 5/1994 | McMahon et al. | |
| 5,527,673 A | 6/1996 | Reinhartz et al. | |
| 5,550,039 A | 8/1996 | Trachtenberg | |
| 5,741,647 A | 4/1998 | Tam | |
| 6,020,187 A | 2/2000 | Tam | |
| 6,670,124 B1 | 12/2003 | Chow et al. | |
| 6,818,393 B1 | 11/2004 | Mach et al. | |
| 7,132,239 B2 | 11/2006 | Livak et al. | |
| 7,732,138 B2 | 6/2010 | Tam | |
| 2004/0185452 A1 | 9/2004 | Chen et al. | |
| 2004/0209253 A1 | 10/2004 | Tam | |
| 2005/0079493 A1 | 4/2005 | Tam | |
| 2007/0031826 A1 | 2/2007 | Lee et al. | |
| 2007/0031827 A1 | 2/2007 | Lin et al. | |
| 2008/0206773 A1 | 8/2008 | Tam | |
| 2011/0111389 A1 | 5/2011 | Tam et al. | |

FOREIGN PATENT DOCUMENTS

| | | |
|---|---|---|
| CN | 1804043 | 7/2006 |
| CN | 101017141 | 8/2007 |
| CN | 102985565 | 3/2013 |
| EP | 1746168 | 1/2007 |
| EP | 2563939 | 3/2013 |
| WO | 03100095 | 12/2003 |
| WO | 2004023092 | 3/2004 |
| WO | 2007115491 | 10/2007 |
| WO | 2008122241 | 10/2008 |
| WO | 2009044370 | 4/2009 |
| WO | 2011139750 | 11/2011 |

OTHER PUBLICATIONS

Brightwell Mol. Cel. Prob. 16(4): 297-305, 2002.
Chakraborty et al., Jul. 1996, "Paternity exclusion by DNA markers: effects of paternal mutations", Journal of Forensic Science, vol. 41(4): 671-677.
Edwards et al., Oct. 1991, "DNA typing and genetic mapping with trimeric and tetrameric tandem repeats", American Journal of Human Genetics, vol. 49(4): 746-756.
Gill et al., Dec. 1985, "Forensic application of DNA 'fingerprints'", Nature, vol. 318(6046): 577-579.
Robinson et al., Jan. 2003, "IMGT/HLA and IMGT/MHC: sequence databases for the study of the major histocompatibility complex", Nucleic Acids Research, vol. 31(1):311-314.
Robinson et al., Jan. 2001, "IMGT/HLA Database—a sequence database for the human major histocompatibility complex", Nucleic Acids Research, vol. 29(1):210-213.
Thomas, E. Donnall, Sep. 1983, "Marrow Transplantation for Malignant Diseases", Journal of Clinical Oncology, vol. 1(9): 517-531.
Weiss, Kenneth M., Jul. 1998, "In search of human variation", Genome Research, vol. 8(7): 691-697.
Zhao et al., Jul. 1998, "Mapping of complex traits by single-nucleotide polymorphisms", American Journal of Human Genetics, vol. 63(1): 225-240.
Bunce M et al. Nov. 1995, "Phototyping: comprehensive DNA typing for HLA-A, B, C, DRB1, DRB3, DRB4, DRB5 & DQB1 by PCR with 144 primer mixes utilizing sequence-specific primers (PCR-SSP)" Tissue Antigens, 46, 355-367.
Mach B et al., 1990, in Molecular Biology of HLA Class II Antigens, ed. Silver J (CRC, Boca Raton, FL), pp. 201-223.
Kaneshige T et. al., Feb. 1993, Rapid and Practical HLA Class II Genotyping by Reversed Dot Blotting, Transplantation Proceedings 25(1): 194-198.

(Continued)

*Primary Examiner* — Jehanne Sitton
(74) *Attorney, Agent, or Firm* — Law Offices of Albert Wai-Kit Chan, PLLC

(57) ABSTRACT

The present invention discloses methods, primer, probes, and kits for genotyping various mutations or disease-causing agent. In one embodiment, the present invention is applied to detecting the presence of multidrug-resistant *Mycobacterium tuberculosis*, HBV, beta-globin mutations, mutations related to thrombophilia, or the presence of sexually transmitted diseases in a subject.

4 Claims, 38 Drawing Sheets

(56) References Cited

OTHER PUBLICATIONS

Inagaki S., et. al., 2004, "A new 39-plex analysis method for SNPs including 15 blood group loci" Forensic Science International 144:45-57.

Dixon L.A., Murray C.M., Archer E. J., Dobbins A.E., Koumi P., Gill P., Nov. 2005, "Validation of a 21-locus autosomal SNP multiplex for forensic identification purposes." Forensic Science International 154:62-72.

Lessig R., Zoledziewska M., Fahr K., Edelmann J., Kostrzewa M., Dobosz T., and Kldelmann W. J. Y, Nov. 2005, "Y-SNP-genotyping—a new approach in forensic analysis", Forensic Science International 154:128-136.

Li L. et al., Oct. 2006, "SNP genotyping by multplex amplification and microarrays assay for forensic application", Forensic Science International 162:74-79.

Kidd K.K., et al., Dec. 2006, Developing a SNP panel for forensic identification of individuals, Forensic Science International 164:20-32.

Reich d.E., et. al., Sep. 2002, Human genome sequence variation and the influence of gene history, mutation and recombination, Nat. Genet. 32:135-140.

Huang Q. Y. et al., Mar. 2002, Mutation patterns at dinucleotide microsatellite loci in humans, Am. J. Hum. Genet. 70:625-634.

Sanchez J.J., et al., May 2006, a multiplex assay with 52 single nucleotide polymorphisms for human identification, Electrophoresis 27:1713-1724.

Dynal Biotech 510 K Summary, 2003.

Application Instruction for HLA DQB1 Genotyping kit, 2000.

Michou et al., Apr. 2006, "Validation of the reshaped shared epitope HLA-DRB1 classification in rheumatoid arthritis." Arthritis Research & Therapy vol. 8(3): 1-6.

Allen et al., 2005, "Universal Tag Arrays in Forensic SNP Analysis", Methods in Molecular Biology, vol. 297:141-154.

Alonso et al., Dec. 2006, "Usefulness of Microchip Electrophoresis for the Analysis of Mitochonrial DNA in Forensic and Ancient DNA Studies", Electrophoresis, vol. 27(24): 5101-9.

Bouakaze et al., Nov. 2007, "First Successful Assay of Y-SNP Typing by SNaPshot minisequencing on Ancient DNA", International Journal of Legal Medicine, vol. 121(6): 493-499.

Budowle et al., Jul. 2005, "Forensic Aspects of Mass Disasters: Strategic Considerations for DNA-based Human Identification", Leg Med (Tokyo), vol. 7(4):230-243.

Lee et al., Mar. 2005, "Selection of Twenty-Four Highly Informative SNP Markers for Human Identification and Paternity Analysis in Koreans", Forensic Science International, vol. 148(2-3): 107-112.

Morling, N., Feb. 2003, "Forensic Genetics", Ugeskr Larger, vol. 165(9): 922-925.

Onofori et al., May 2007, "Y-Chromosome Genetic Structure in Sub-Apennine Populations of Central Italy by SNP and STR Analysis", International Journal of Legal Medicine, vol. 121(3): 234-237.

Pakstis et al., May 2007, "Candidate SNPs for a Universal Individual Identification Panel", Human Genetics, vol. 121 (3-4): 305-317.

Petkovski et al., May 2005, "SNPs and MALDI-TOF MS: Tools for DNA typing in Forensic Paternity Testing and Anthropology", Journal of Forensic Science, vol. 50(3): 535-541.

Divne, Anna-Maria, and Allen, Marie, 2005, "A DNA Microarray System for Forensic SNP analysis", Forensic Science International, vol. 154(1): 111-121.

Olerup SSP™ HLA Products From GenoVision: Full Product Review, 2006.

Buck et al., Sep. 1999, ""Design strategies and performance of custom DNA sequencing primers."" Biotechniques, 27(3): 528-536.

"Demidov et al., Feb. 2004, ""Two sides of the coin: affinity and specificity of nucleic acid interactions""" Trends is Biochemical Sciences, vol. 29: 62-71".

Munoz et al., Feb. 2003, "Epidemiologic classification of human papillomavirus types associated with cervical cancer." N Engl J Med, 348:518-27.

Anttila et al, Oct. 2009, "Cervical cancer screening policies and coverage in Europe" Eur J Cancer 45:2649-58.

Center for Disease Control and Prevention, Apr. 2007, "Human Papillomavirus: HPV information for Clinicians".

Walboomers et al., Sep. 1999, "Human papillomavirus is a necessary cause of invasive cervical cancer worldwide." J Pathol, 189:12-9.

Kjaer et al., Sep. 2002, "Type specific persistence of high risk human papillomavirus (HPV) as indicator of high grade cervical squamous intraepithelial lesions in young women: population based prospective follow up study" BMJ, 2002, 325:572.

"Chow, 2008, ""A Membrane-Based Flow-through Hybridization Technology: A Rapid and Versatile tool for Molecular Diagnostics""" Open Biotechnol J., 2:22-28".

Grondahl et al., Jan. 1999, "Rapid Identification of Nine Microorganisms Causing Acute Respiratory Tract Infections by Single-Tube Multiplex Reverse Transcription-PCR: Feasibility Study" J Clin Microbiol, 37:1-7.

Mackay et al., Jan. 2003, "Molecular assays for detection of human metapneumovirus." J Clin Microbiol, 100-105.

U.S. Office Action, Oct. 25, 2004, for U.S. Appl. No. 10/291,168, filed Nov. 7, 2002.

U.S. Office Action, Mar. 21, 2005, for U.S. Appl. No. 10/291,168, filed Nov. 7, 2002.

U.S. Office Action, Jan. 4, 2006, for U.S. Appl. No. 10/291,168, filed Nov. 7, 2002.

U.S. Office Action, Sep. 7, 2007, for U.S. Appl. No. 10/293,248, filed Nov. 9, 2002.

U.S. Office Action, Nov. 2, 2007, for U.S. Appl. No. 11/398,433, filed Apr. 4, 2006.

PCT International Search Report, Aug. 16, 2007, for Int' App'l PCT/CN2007/001108, filed Apr. 4, 2007.

PCT Written Opinion, Aug. 16, 2007, for Int' App'l PCT/CN2007/001108, filed Apr. 4, 2007.

U.S. Office Action, Jun. 6, 2008, for U.S. Appl. No. 11/398,433, filed Apr. 4, 2006.

U.S. Office Action, May 1, 2009, for U.S. Appl. No. 12/044,126, filed Mar. 7, 2008.

PCT International Search Report and Written Opinion, Apr. 30, 2009, for Int' App'l PCT/IB2008/054044, filed Oct. 3, 2008.

U.S. Office Action, Dec. 18, 2009, for U.S. Appl. No. 11/398,433, filed Apr. 4, 2006.

PCT International Search Report, Oct. 4, 2011, for Int' App'l PCT/US2011/034100, filed Apr. 27, 2011.

PCT Written Opinion, Oct. 4, 2011, for Int' App'l PCT/US2011/034100, filed Apr. 27, 2011.

U.S. Office Action, Nov. 29, 2011, for U.S. Appl. No. 12/770,034, filed Apr. 29, 2010.

U.S. Office Action, Feb. 21, 2012, for U.S. Appl. No. 12/770,034, filed Apr. 29, 2010.

U.S. Office Action, Jul. 9, 2011, for U.S. Appl. No. 12/770,034, filed Apr. 29, 2010.

Chinese Office Action, Oct. 9, 2013, for Chinese App'l 201180032327.1, filed Dec. 28, 2012 (with English Translation).

Mitiaeva et al., Mar. 2007, "Development and Application of Hydrogel Oligonucleotide Microships for Forensic-Medical Personal Identification as Illustrated by ABO Locus", Sud. Med. Ekspert, vol. 50(2): 51-25.

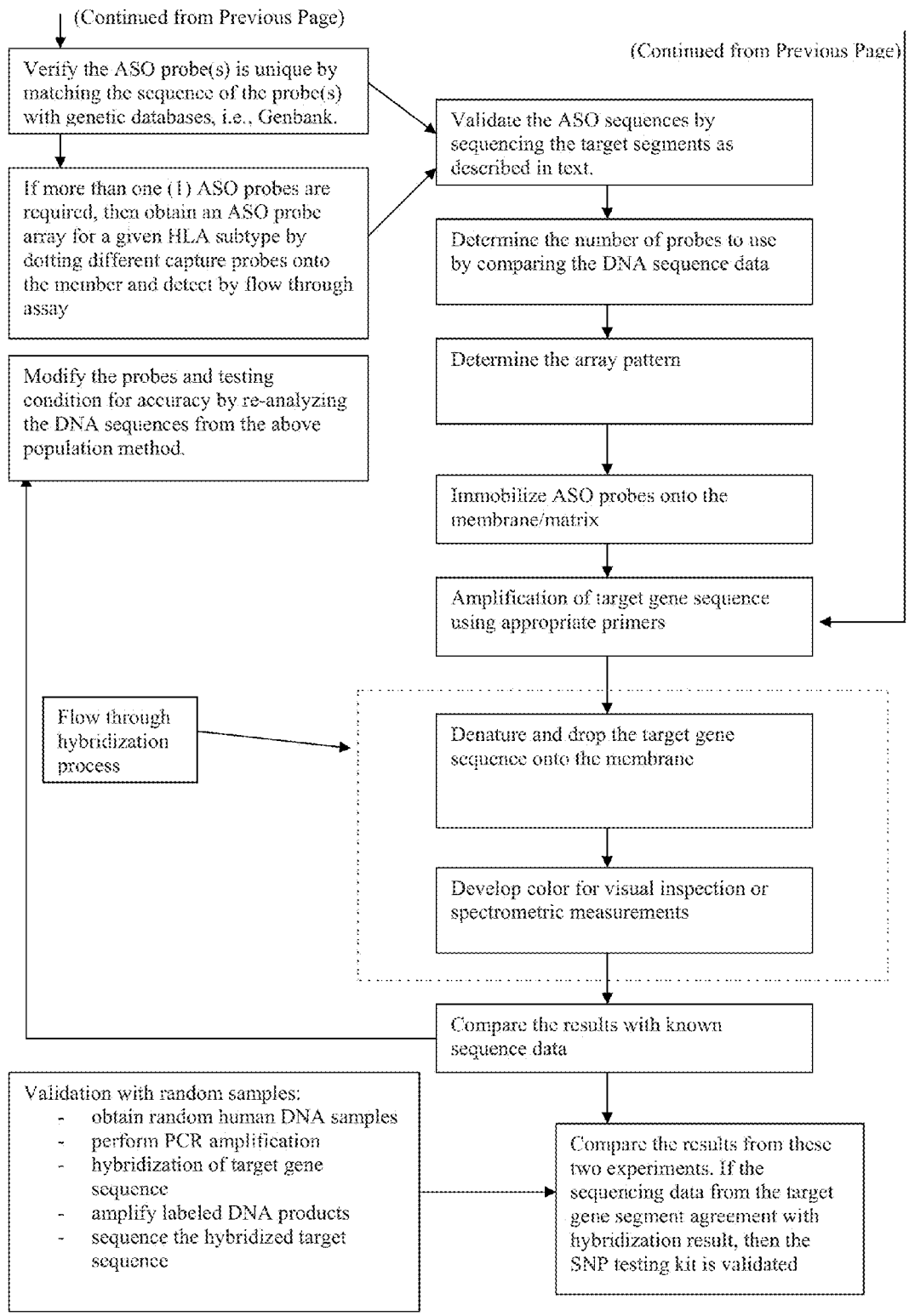
Figure 1A (Con't)

Figure 6
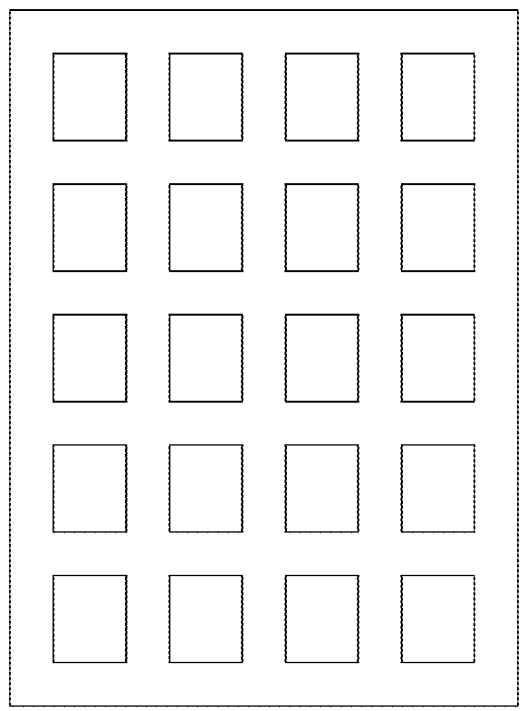
B. Typical images of *TWO* of the 24 Arrays testing for multiple genes or sequences.
A. a 20 Arrays membrane Figure 7
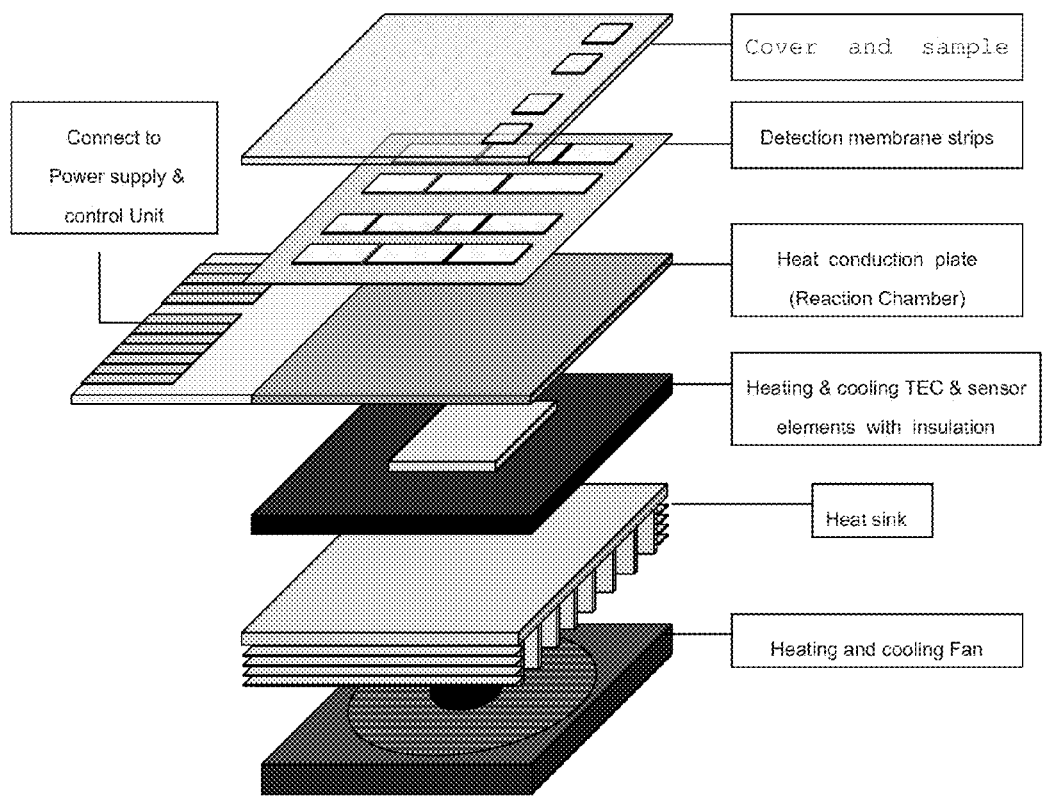
A. Miniature DNA Lateral Flow Device
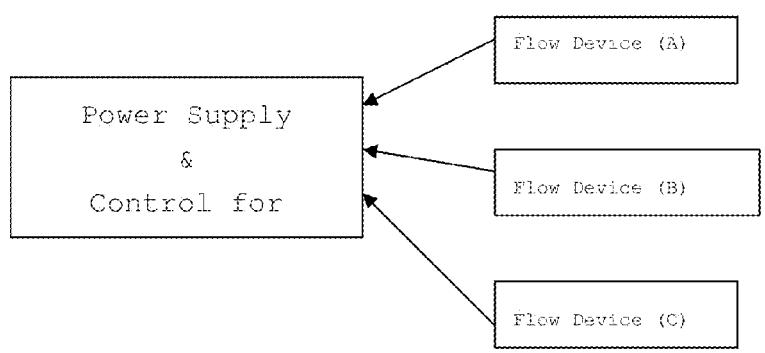
B. The Arrangement Structure for Multiple Miniature Devices

Figure 11

HLA-DPB1 Gene typing results

| Samples | Genotype | | Samples | Genotype | |
|---|---|---|---|---|---|
| BR-101 | 0301/1301 | | BR-134 | 6501/0501 | |
| BR-102 | 0301/1301 | | BR-135 | 0401/0401 | |
| BR-104 | 4701/4801 | | BR-136 | 0501/0501 | |
| BR-105 | 0202/1701 | | BR-139 | 2201/0402 | |
| BR-109 | 0601/7901 | | BR-140 | 0501/0501 | |
| BR-110 | 02012/0501 | | BR-141 | 0501/0501 | |
| BR-111 | 0601/26012 or 2701/2901 | | BR-142 | 0501/0301 | |
| BR-112 | 0501/0301 | | BR-145 | 1601/3901 | |
| BR-113 | 0501/0401 | | BR-146 | 02012/4801 | |
| BR-116 | 0501/0202 | | BR-147 | 0501/0501 | |
| BR-117 | 0501/0501 | | BR-148 | 0402/2201 or 0501/02012 | |
| BR-118 | 02012/0202 | | BR-149 | 0501/0202 | |
| BR-119 | 0402/0501 | | BR-150 | 0501/0501 | |
| BR-120 | 0501/0501 | | BR-137 | 2201/0402 | |
| BR-121 | 0501/0501 | | BR-138 | 0501/3101 | |
| BR-122 | 0401/1701 | | BR-143 | 0501/0402 | |
| BR-123 | 02012/0202 | | BR-144 | 1301/0402 | |
| BR-124 | 0501/0501 | | 31A | 0501/02012 | |
| BR-125 | 02012/0101 | | 31B | 02012/1301 | |
| BR-126 | 0501/0401 or 2401/6301 | | 32A | 02012/5001 | |
| BR-127 | 0402/3301 | | 32B | 0501/02012 | |
| BR-128 | 1301/2101 | | TH1A | 0501/1301 | |
| BR-129 | 0501/0501 | | TH1B | 0501/0501 | |
| BR-130 | 0501/1901 | | TH15A | 0501/0202 | |
| BR-131 | 0501/02012 | | TH15B | 0501/0401 | |
| BR-132 | 0501/0501 | | 20003 | 0501/0501 | |
| BR-133 | 0501/02012 | | TH2B | 0501/02012 | |
| TH2A | 02012/5001 | | | | |

Table 1

Figure 12

Table 2 Allele and genotype frequencies of HLA-DPB1

| Genotype | n | Frequencies(n=47) (%) | Alleles | n | Frequencies(n=94) (%) |
|---|---|---|---|---|---|
| 0202/1701 | 1 | 2.13 | 101 | 1 | (1.06) |
| 0101/02012 | 1 | 2.13 | 2012 | 14 | (14.89) |
| 02012/0202 | 1 | 2.13 | 202 | 8 | (8.51) |
| 02012/1301 | 1 | 2.13 | 301 | 2 | (2.13) |
| 02012/4801 | 1 | 2.13 | 401 | 3 | (3.19) |
| 02012/5001 | 2 | 4.26 | 402 | 4 | (4.26) |
| 02012/6301 | 1 | 2.13 | 501 | 46 | (48.94) |
| 0301/1301 | 2 | 4.26 | 1301 | 6 | (6.38) |
| 0401/1701 | 1 | 2.13 | 1601 | 1 | (1.06) |
| 0402/3301 | 1 | 2.13 | 1701 | 2 | (2.13) |
| 0401/0401 | 1 | 2.13 | 1901 | 1 | (1.06) |
| 0501/02012 | 6 | 12.77 | 2101 | 1 | (1.06) |
| 0501/0202 | 3 | 6.38 | 3101 | 1 | (1.06) |
| 0501/0402 | 2 | 4.26 | 3301 | 1 | (1.06) |
| 0501/1301 | 1 | 2.13 | 3901 | 1 | (1.06) |
| 0501/1901 | 1 | 2.13 | 4101 | 1 | (1.06) |
| 0501/3101 | 1 | 2.13 | 4801 | 1 | (1.06) |
| 0501/4101 | 1 | 2.13 | 5001 | 2 | (2.13) |
| 0501/6501 | 1 | 2.13 | 6301 | 1 | (1.06) |
| 0501/0501 | 15 | 31.91 | 6501 | 1 | (1.06) |
| 1301/2101 | 1 | 2.13 | | | |
| 1301/0402 | 1 | 2.13 | | | |
| 1601/3901 | 1 | 2.13 | | | |

Table 2

Figure 13

Table 3. Oligonucleotide (ASO) Probe Sequences used for the identification of HLA-DRB specific alleles

| SEQ ID No. | Name | Codon | Sequence (5'→3') | Specificity (Allele) | Tm (°C) |
|---|---|---|---|---|---|
| 1 | (1) DRB1*01 | 26-32 | TTG CTG GAA AGA TGC AT | 1*01 all | 47.9 |
| 2 | (2) DRB1-03a | 69-73 | GAG CAG AAG CGG GG | 1*03 all, 1*0422, 1*1107, DRB3 all | 54 |
| 3 | DRB1*03b | 78-73 | CAG TAA TTG TCC ACC | 1*03012, 1*03022, 1*0104 | 46.26 |
| 4 | (3) DRB1*04b | 29-35 | AGATACTTCTATCACCAAGA | 1*0401, 1-0427 | 46.11 |
| 5 | (4) DRB1*07a | 78-74 | CAC GGT GTC CAC CTG | 1*0701, 1*0703 | 52 |
| 6 | DRB1-07b | 10-15 | CAG GGT AAG TAT AAG TGT | 1*07 all | 46.65 |
| 7 | (5) DRB1*08 | 74-69 | AGG GCC CGC CTG TC | 1*0801-08043, 1*0806-08017, 0819, 1*1604 1*0412,18,25, 1*1123, 1125 | 60 |
| 8 | (6) DRB1*09a | 8-13 | C TTG AAG CAG GAT AA | 1*09012 | 45 |
| 9 | DRB1*09b | 25-30 | TAT CTG CAC AGA GGC | 1*09012 | 44.7 |
| 10 | (7) DRB1*10a | 8-13 | TTG GAGGAGGTTAAGT | 1*1001 | 44.77 |
| 11 | DRB1*10b | 28-33 | A AGA CGC GTC CAT AA | 1*1001 | 47.94 |
| 12 | (8) DRB1*11 | 62-57 | TTC CAG TAC TCC TCA TCA | 1*11 all | 43.23 |
| 13 | (9) DRB1*12 | 35-40 | GAG CTC CTG CGC TTC | 1*1201-1204, 1*12021 1*12022, 1*1204 | 53.44 |
| 14 | (10) DRB1*13 | 73-69 | GGC CCG CTC GTC TT | 1*1301-1332 (1302,04,08,15*322) 1*1416, 1*0402, 1*0414 | 56.47 |
| 15 | (11) DRB1*14a | 62-56 | A GTG CTC CGC GCA | 1*1401-04,07,10,16,22, 25,26,28,31, 1*0707, 1*0310 | 53.42 |
| 16 | DRB1*14b | 74-70 | TCG GCC CGC CTC CT | 1*1407-11, 1*1414, 1*1418,23,26,28 | 62.68 |
| 17 | (12) DRB1*15 | 71-67 | CGC CTG CTC CAG GA | 1*15all, DRB5*0106 DRB5*0201-0204 | 55.85 |
| 18 | DRB1*15b | 10-15 | CAG CCT AAG AGG GAG T | 1*15all, 1*16all | 47.53 |
| 19 | (13) DRB1*1603 | 69-73 | AA GAC AGG GCC GCC | 1*1603 | 56.7 |
| 20 | (14) DRB1*1607 | 26-30 | CCC GGA CAG ATA CTT | 1*1607 | 45 |

Figure 13 (cont'd)

Table 3. Oligonucleotide (ASO) Probe Sequences used for the identification of HLA-DRB specific alleles (con't)

| SEQ ID No. | Name | Codon | Sequence (5'→3') | Specificity (Allele) | Tm (°C) |
|---|---|---|---|---|---|
| 21 | (15) DRB3a | 9-14 | GGAG CTG CTT AAG TCT<br>** * | DRB3*0103-0303 | 44.86 |
| 22 | DRB3b | 35-40 | GAG TTC CTG CGC TTC<br>* * | DRB3*01, DRB1*1205 | 50 |
| 23 | DRB3c | 77-73 | ATT GTC CAC CTG GCC<br>* ** * | DRB3*0202, *0204<br>DRB3*0206-0208<br>DRB3*0301-0302 | 52 |
| 24 | (16) DRB4a | 25-30 | TGG AAC CTG ATC AGA TAC<br>* *** *** | | 48.22 |
| 25 | DRB4b | 40-44 | GC TAC AAC AGT GACCTG | DRB4 all | 46.82 |
| 26 | (17) DRB5a | 26-30 | TTC CTG CAC AGA GAC<br>* * * * * | DRB5*01011, 01012, 0104, -0107, 0109, 0201 | 44.07 |
| 27 | DRB5b | 26-30 | TTC CTG CAC AGA GGC<br>* * * * * | DRB5*0102, 0103, 0108N<br>DRB5*0201, 02012, 0203, 0204 | 51.43 |
| 28 | DRB5c | 35-40 | AGG AGG ACT TGC GCT T<br>* * * | DRB5*0101, 01012, 0104, DRB5*0106, 0107, 0109 | 56.40 |
| 29 | (18) DRB all | 61-65 | TGG AAC AGC CAG AAG | DRB all | |

Table 4. PCR primers pairs for amplifying the HLA-DRB fragments

| SEQ ID No. | Name | Codon | Sequence (5'→3') | Tm (°C) |
|---|---|---|---|---|
| 97 | DRB-F1 | In intern-1 | ATCCTTCGTGTCCCCACAGCACG | |
| 98 | DRB-R1 | | GCCGCTGCACTGTGAAGCTCTC | |

Figure 13 (cont'd)
Table 5. Oligonucleotide (ASO) Probe Sequences used for the identification of HLA-DQB1 specific alleles

| SEQ ID No. | Name | Codon | Sequence (5'→3') | Specificity | Tm(°C) |
|---|---|---|---|---|---|
| 30 | Probe1 | 26-31 | GT GTG ACC AGA CAC AT | 0501,0502,05031,05032, | 43 |
| 31 | Probe2 | 27-32 | GTGACCAGATACATCTATAA | 0504,0305,0401,0402, | 44.48 |
| 32 | Prboe3 | 24-30 | CGTCTTGTGACCAGATA | 0602,0610,0611,0613, 0302,0303,0306,0307, | 47.28 |
| 33 | Probe4 | 26-31 | CGTCTTGTAACCAGAC | 0603,0604,0607,0608,0614, | 43.28 |
| 34 | Probe5 | 25-31 | GTCTTGTAACCAGATACAT | 06051,06052,0606,0609, 0612, | 43.98 |
| 35 | Probe6 | 23-29 | CGTGCGTTATGTGA | 06011,06012,06013, 03011,03012,0304, | 44.33 |
| 36 | Probe7 | 20-26 | GGACCGAGCTCGTG | 0401. | 51 |
| 37 | Probe8 | 19-23 | ACCAACGGGACCGAG | 0305,0402,0401 | 55.99 |
| 38 | Probe8b | 19-24 | AACGGGACCGAGCG | 0305,0402, | 57.47 |
| 39 | Probe9 | 55-59 | GCCTAGCGCCGAGTA | 0502,0504,0610, | 54 |
| 40 | Probe10 |  | TGGGGCTGCCTGCC | 0201,0202 |  |
| 41 | Probe11 | 44-48 | GTGGGGGAGTTCCG | 0201,0202,0203, | 53.2 |
| 42 | Probe12 | 20-24 | TGCCTGACGCCGAG | 0203. | 57.12 |
| 43 | Probe13 | 20-25 | GCTTGACGCCGAGTA | 0401,0402. | 51.88 |
| 44 | Probe14 | 43-49 | CGACGTGGAGGTGTAC | 03011,03012,0304 | 50.55 |
| 45 | Probe15 | 34-39 | AGGAGGACGTGCGCT | 06013,06012,06011 | 56.06 |
| 46 | Probe16 |  | TATCGGGCGGTGACC | 06012, | 57.15 |
| 47 | Probe17 |  | GTGAGCAGAAGCATC | 0201,0202,0203 | 43.84 |
| 48 | Probe18 | 33-39 | CCGAGAAGAGTACGTGC | 0504. | 52.34 |
| 49 | Probe19 | 75-80 | GTGGACAGAGTGTGCA | 0502,05031 | 48.66 |
| 50 | Probe20 | 55-59 | CGCCTGCCGCCGAG | 0302,0304,0305,0307 | 65.33 |
| 51 | Probe21 | 55-59 | CGCCTGACGCCGAG | 03011,03012,03021, | 59.76 |
| 52 | Probe22 | 46-51 | TACCGGGCAGTGAC | 0501 | 48.63 |
| 53 | Probe23 | 55-60 | CTGTCGCCGACTAC | 06052, | 44.95 |

Figure 13 (cont'd)

Table 6. PCR primers pairs for amplifying the HLA-DQB gene fragment

| SEQ ID No | Name | Codon | Sequence (5'-3') | Specificity | Tm(°C) |
|---|---|---|---|---|---|
| 99 | DQB-E2-F2 | -6 to 6 | CGGTGATTCCCCGCAGAGGAT | | |
| 100 | DQB-E2-R2 | 86-79 | CCACCTCGTAGTTGTGTCTGC | | |

Figure 13 (cont'd)

Table 7. Oligonucleotide (ASO) Probe Sequences used for the identification of HLA-DPB specific alleles

| SEQ ID No. | Name | Position of amino acid | Sequence (5'→3') | Specificity (Allele) | Tm(°C) |
|---|---|---|---|---|---|
| 54 | SSO1 | 8-11 VYQG | AC GTG TAC CAG GGA C | 01011,01012,1501,1801,5001 | 46.07 |
| 55 | SSO2 | 8-9 LF | AC CTT TTC CAG GGA C | | 47.61 |
| 56 | SSO2b | 12 Q | G GGA CGA CAG GAA T | 02011 | 45.81 |
| 57 | SSO3 | 11 L | G TAC CAG TTA CGG CAG | 6401N | 47.03 |
| 58 | SSO4 | 8-11 H-L | GTG CAC CAG TTA CGG | | 48.5 |
| 59 | SSO5 | 8-11 D-L | T TAC GTG GAC CAG TTA | 7001, | 44.72 |
| 60 | SSO6 | 33-36 EEYA | GAG TAC GCG CGC TT | | 52.11 |
| 61 | SSO7 | 35-36 –FV | GAG TTC GTG CGC TT | | 48.32 |
| 62 | SSO8 | 35-36 –LV | GAG CTC GTG CGC TT | | 51.91 |
| 63 | SSO9 | 35 F | GAG TTC GCG CGC TT | 11011 | 55.18 |
| 64 | SSO10 | 33 Q | TAC AAC CGG CAG GAG | 1501, 7401, | 51.46 |
| 65 | SSO10b | 32 R | TAC AAC AGG CAG GAG | 11011 | 44.72 |
| 66 | SSO11 | 55-57 AAE | T GCT GCG GAG TAC T | | 45.23 |
| 67 | SSO12 | 55-56 DE | G CCT GAT GAG GAG TAC T | | 47.25 |
| 68 | SSO12b | 55-56 DE | CCT GAC GAG GAG TAC T | | 44.83 |
| 69 | SSO13 | 55 E | CT GAG GCG GAG TAC T | | 46.02 |
| 70 | SSO14 | 55-57 DED | G CCT GAT GAG GAC TAC T | | 47.25 |
| 71 | SSO15 | 65 I | G AAG GAC ATC CTG GA | | 46.08 |
| 72 | SSO16 | 65 L | AAG GAC CTC CTG GA | | 45.39 |
| 73 | SSO17 | 65 F | AG AAG GAC TTC CTG G | 4101, | 44.51 |
| 74 | SSO18 | 65 N | AG AAG GAC AAC CTG G | 6001, | 45.41 |
| 75 | SSO19 | 69 K | GAG AAG CGG GCA GT | | 50.22 |
| 76 | SSO20 | 69 E | GAG GAG CGG GCA GT | | 53.28 |
| 77 | SSO21 | 69 R | GAG AGG CGG GCA GT | 11011,11012, 1501,6901,7401, | 53.28 |
| 78 | SSO22 | 72 L | GCA TTG CCG GAC AG | 3101,3401 | 52.92 |
| 79 | SSO23 | 73 L | GC AGTG CTG GAC AGG | 7801, | 51.83 |
| 80 | SSO24 | 76 V | C AGG GTA TGC AGA CA | | 45.43 |

Figure 13 (cont'd)

Table 7. Oligonucleotide (ASO) Probe Sequences used for the identification of HLA-DPB specific alleles (con't)

| SEQ ID No. | Name | Position of amino acid | Sequence (5'→3') | Specificity (Allele) | Tm(°C) |
|---|---|---|---|---|---|
| 81 | SSO25 | 76 I | AC AGG ATA TGC AGA CA | | 43.95 |
| 82 | SSO26 | 76 M | AC AGG ATG TGC AGA C | | 43.47 |
| 83 | SSO27 | 83-86 DEAV | TAC GAG CTG GAC GAG | | 48.43 |
| 84 | SSO28 | 83-86 GGPM | TAC GAG CTG GGC GG | | 55.89 |
| 85 | SSO29 | 83-86 VGPM | TAC GAG CTG GTC GG | | 49.2 |
| 86 | SSO30 | 61-66 | AA GGA CCT CCT GTA GG | 6101N | 47.05 |
| 87 | SSO31 | 10-14 | CA GGG ACT GCA GGA A | 7701 | 46.9 |
| 88 | SSO32 | 14-19 | AATG CTACCCGTTTA | 3801 | 44.11 |
| 89 | | 6-12 | TAAGTGTACCAGTTACGG | 6401N | 46.33 |
| 90 | | 30-34 | ATCTACAACCGGCAG | 1501, 7401 | |
| 91 | | 40-46 | GACGTGGGAGAGTTC | 01012, 11011,11012, 1501, 26011 | 45.57 |
| 92 | | 61-66 | AAGGACCTCCTGTAGG | 6101N | 47.05 |
| 93 | | 69-74 | AAGCGGGCATTGCC | 3101, 3401 | 57.5 |
| 94 | | 70-74 | GGGCAGTGCTAGAC | 7801 | 43.63 |
| 95 | | 14-19 | AATGCTACCCGTTTA | 3801 | 44.11 |
| 96 | | 7-12 | TTACGTGGACCAGT | 7001 | 45.14 |

Figure 13 (cont'd)

Table 8. Primers for HLA-DPB gene fragment (f: forwards and r: backwards primers)

| SEQ ID No. | Name | Position of amino acid | Sequence (5'→3') | Tm(°C) |
|---|---|---|---|---|
| 101 | Primer1-f | 3-9 | GCCACTCCAGAGAATTACCTTTT<br>              * * * | 60.02 |
| 102 | Primer2-f | 4-9 | CCAGAGAATTACGTGTACCAGTT<br>             ** | 57.39 |
| 103 | Primer3-f | 4-11 | CCAGAGAATTACGTGCACCAGTT<br>         *   ** | 62.62 |
| 104 | Primer4-r | 89-84 | CAGGGTCATGGGCCCGC<br>     * * * * | 68 |
| 105 | Primer5-f | 90-84 | GCAGGGTCATGGGCCCGA<br>      * ** * | 70 |
| 106 | Primer6-r | 89-84 | CAGGGTCACGGCCTCGTC | 65.34 |

Figure 14

The Oligonucleotide probe and PCR primer sequences used for HPV genotyping Analyses

| SEQ ID No. | Name | Primer Sequence (5' to 3') | 5' Modification | Length | Target sequence |
|---|---|---|---|---|---|
| 116 | HPVF | GCMCAGGGWCATAAYAATGG | Biotin | 20 | Reverse strand of HPV L1 |
| 117 | HPVR | CGTCCMARRGGAWACTGATC | Biotin | 20 | Forward strand of HPV L1 |
| 118 | HPVR2 | GCGACCCAATGCAAATTGGT | None | 20 | Forward strand of HPV L1 |
| 119 | IC-F | GTGCACCTGACTCCTGAGGAG | None | 21 | Reverse strand of β-globin |
| 120 | IC-R | CCTTGATACCAACCTGCCCAG | Biotin | 21 | Forward strand of β-globin |

| | Name | Probe Sequence (5' to 3') | 5' Modification | Length | Target sequence |
|---|---|---|---|---|---|
| 121 | 11 F | ATCTGTGTCTAAATCTGCTACA | Amine | 22 | Reverse strand of HPV 11 |
| 122 | 11 R | GTACATATCTATAAGTATCCTCCAGT | Amine | 26 | Forward strand of HPV 11 |
| 123 | 16 F | GCCATATCTACTTCAGAAACTAC | Amine | 23 | Reverse strand of HPV 16 |
| 124 | 18 F | TGCTTCTACACAGTCTCCT | Amine | 19 | Reverse Strand of HPV 18 |
| 125 | 18 R | TATTTTCAGCCGGTGCAGCAT | Amine | 21 | Forward strand of HPV 18 |
| 126 | 26 F | GCATCTGCATCCACTC | Amine | 16 | Reverse strand of HPV 26 |
| 127 | 31 F | GCAATTGCAAACAGTGATAC | Amine | 20 | Reverse strand of HPV 31 |
| 128 | 31 R | GATCTTCCTTGGGCTTTTGG | Amine | 20 | Forward strand of HPV 31 |
| 129 | 33 F | TGCACACAAGTAACTAGTGA | Amine | 20 | Reverse strand of HPV 33 |
| 130 | 33 R | TTTGGAGGTACTGTTTTTGA | Amine | 21 | Forward strand of HPV 33 |
| 131 | 35 F | CTGCTGTGTCTTCTAGTGA | Amine | 19 | Reverse strand of HPV 35 |

Figure 14
(cont'd)

| | | | | | |
|---|---|---|---|---|---|
| 132 | 39 F | TACATTATCTACCTCTATAGA | Amine | 21 | Reverse strand of HPV 39 |
| 133 | 39 R | GCAGACTGTAGGTATCTGTAAGTG | Amine | 24 | Forward strand of HPV 39 |
| 134 | 40 F | CCACCAACCCCATATAA | Amine | 19 | Reverse strand of HPV 40 |
| 135 | 42 F | GCCACTGCAACATCTGGTG | Amine | 19 | Reverse strand of HPV 42 |
| 136 | 42 R | GCGTTGTTACCTTAGCCTGA | Amine | 20 | Forward strand of HPV 42 |
| 137 | 43 F | TCTACTGACCCTACTGTG | Amine | 18 | Reverse strand of HPV 43 |
| 138 | 44 F | TACTAGTGAACAATATAAGCA | Amine | 21 | Reverse strand of HPV 44 |
| 139 | 44 R | TTAATTTTGCATAGGGGTCCT | Amine | 21 | Forward strand of HPV 44 |
| 140 | 45 F | TAATTTAACATTATGTGCCTC | Amine | 21 | Reverse strand of HPV 45 |
| 141 | 51 F | CCCAACATTTACTCCAAGTAACT | Amine | 23 | Reverse strand of HPV 51 |
| 142 | 51 R | CTGTTCAAGAATGGTAGGATC | Amine | 21 | Forward strand of HPV 51 |
| 143 | 52 F | TGCTGAGGTTAAAAAGGAAAGCACATATAA | Amine | 30 | Reverse strand of HPV 52 |
| 144 | 53 F | CCACACAGTCTATGTCTAC | Amine | 19 | Reverse strand of HPV 53 |
| 145 | 53 R | CCAGTCTTCCAGTAAGGTAGAA | Amine | 22 | Forward strand of HPV 53 |
| 146 | 54 F | ATTGTGTGCTACAGCATC | Amine | 18 | Reverse strand of HPV 54 |
| 147 | 55 F | ACAACTCAGTCTCCATCTAC | Amine | 20 | Reverse strand of HPV 55 |
| 148 | 56 F | GATGCACGAAAAATTAATCAG | Amine | 21 | Reverse strand of HPV 56 |
| 149 | 56 R | TCCTCCAGTAGGTTAGCATT | Amine | 20 | Forward strand of HPV 56 |
| 150 | 57 F | CCACTGTAACCACCAGAAACTAA | Amine | 22 | Reverse strand of HPV 57 |
| 151 | 58 F | ACTGAAGTAACTAAGGAAGGTAC | Amine | 23 | Reverse strand of HPV 58 |
| 152 | 59 F | AGAATATGCCAGACATGTG | Amine | 19 | Reverse strand of HPV 59 |
| 153 | 59 R | GGGTCCTGTTTAACTGGC | Amine | 18 | Forward strand of HPV 59 |
| 154 | 6 F | CATCCGTAACTACATCTTCCA | Amine | 21 | Reverse strand of HPV 6 |

Figure 14
(cont'd)

| | | | | | |
|---|---|---|---|---|---|
| 155 | 61 F | CCTGTATCTGAATATAAAGCCAC | Amine | 23 | Reverse strand of HPV 61 |
| 156 | 66 F | CGTGAAATCAATCAATACCTTC | Amine | 22 | Reverse strand of HPV 66 |
| 157 | 66 R | CGTCTAATAAAGTATTATTCATATTATGC | Amine | 29 | Forward strand of HPV 66 |
| 158 | 68 F | CTGAATCAGCTGTACCAAA | Amine | 19 | Reverse strand of HPV 68 |
| 159 | 70 F | GCCATACCTGCTGTATATAG | Amine | 20 | Reverse strand of HPV 70 |
| 160 | 71 F | GCTACCAAAACTGTTGAGTC | Amine | 20 | Reverse strand of HPV 71 |
| 161 | 72 F | CAGCGTCCTCTGTATCA | Amine | 17 | Reverse strand of HPV 72 |
| 162 | 73 F | GTATGCCAACTCWAATTTTAA | Amine | 21 | Reverse strand of HPV 73 |
| 163 | 81 F | GCACAGCTACATCTGCTGCTGCAGAATACA | Amine | 30 | Reverse strand of HPV 81 |
| 164 | 81 R | GAACAAGGCACTGTTGGATG | Amine | 20 | Forward strand of HPV 81 |
| 165 | 82 F | TACTCCATCTGTTGCACAAA | Amine | 20 | Reverse strand of HPV 82 |
| 166 | 82 R | ACAGGATGTTGCTGCATT | Amine | 18 | Forward strand of HPV 82 |
| 167 | 84 F | CTACCAACACCGAATCAGA | Amine | 19 | Reverse strand of HPV 84 |
| 168 | AC Probe | AAGGTGAACGTGGATGAAGTTGGTGG | Amine | 26 | Reverse of β-globin gene |
| 169 | HC Probe | GTTCCAACTAGGAACATCA | Amine | 19 | N/A |
| 170 | Uni 1 | CATGB!GGAGG+AGTTTGATTTACAAT+TTATGT+TTCA | Amine | 36 | Forward strand of HPV L1 |
| 171 | Uni 2 | GAAGAGTA+TGATTTGCAATTTATAT+TTCA | Amine | 29 | Forward strand of HPV L1 |
| 172 | Uni 3 | TTTG+TTACTGTGGTAGAT+ACTAC | Amine | 23 | Reverse strand of HPV L1 |
| 173 | Uni 4 | GA+AAAATA+AACTGTAAATCATAT+TC | Amine | 25 | Forward strand of HPV L1 |

Figure 16
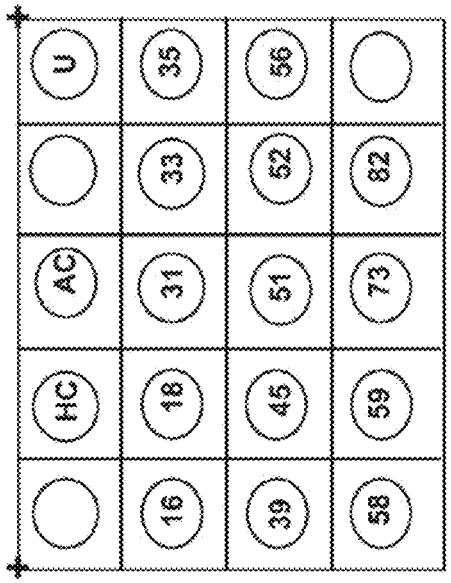
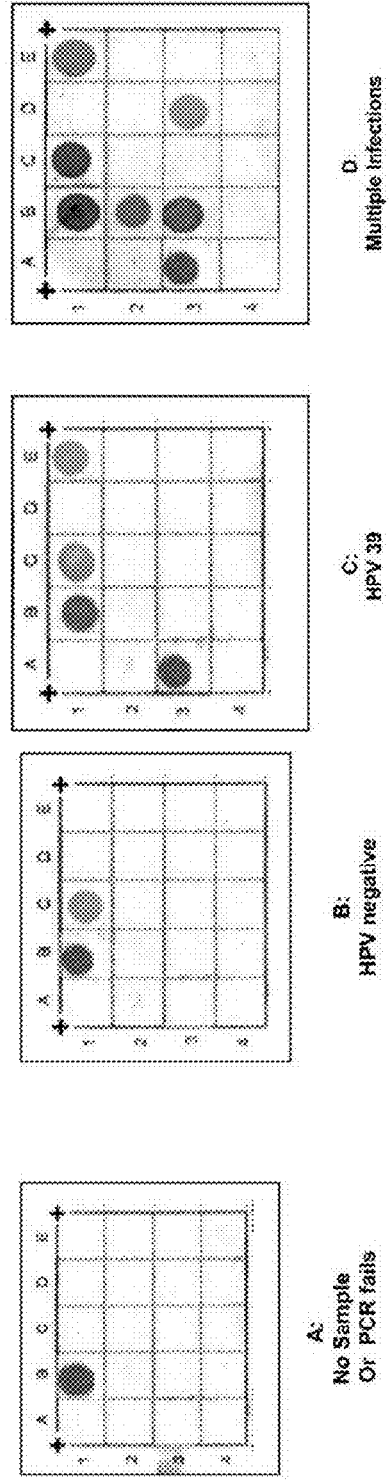

Figure 18

AC= Internal Control
16= HPV16
18= HPV18
HR1= HPV31;33;35;39;45;58
HR2= HPV51;52;56;59;73;82
U= Generic HPV AC= Internal Control
16= HPV16
18= HPV18
HR1= HPV31;33;35;39
HR2= HPV45;51;52;56
HR3= HPV58;59;73;82

AC= Internal Control
16= HPV16
18= HPV18
HR= HPV31;33;35;39;45;51;
   52;56;58;59;68;82
LR = HPV6;11;26;40;42;43;44;
   53;54;55;57;61;66;
   70;71;72;73;81;84
U = Generic HPV

```
                        SEQUENCE LISTING

<160> NUMBER OF SEQ ID NOS: 314

<210> SEQ ID NO 1
<211> LENGTH: 21
<212> TYPE: DNA
<213> ORGANISM: Homo sapiens

<400> SEQUENCE: 1
cggtgattcc ccgcagagga t                                             21

<210> SEQ ID NO 2
<211> LENGTH: 21
<212> TYPE: DNA
<213> ORGANISM: Homo sapiens

<400> SEQUENCE: 2
ccacctcgta gttgtgtctg c                                             21

<210> SEQ ID NO 3
<211> LENGTH: 16
<212> TYPE: DNA
<213> ORGANISM: Homo sapiens

<400> SEQUENCE: 3
gtgtgaccag acacat                                                   16

<210> SEQ ID NO 4
<211> LENGTH: 20
<212> TYPE: DNA
<213> ORGANISM: Homo sapiens

<400> SEQUENCE: 4
gtgaccagat acatctataa                                               20

<210> SEQ ID NO 5
<211> LENGTH: 17
<212> TYPE: DNA
<213> ORGANISM: Homo sapiens

<400> SEQUENCE: 5
cgtcttgtga ccagata                                                  17

<210> SEQ ID NO 6
<211> LENGTH: 16
<212> TYPE: DNA
```

```
<213> ORGANISM: Homo sapiens

<400> SEQUENCE: 6
cgtcttgtaa ccagac                                                  16

<210> SEQ ID NO 7
<211> LENGTH: 33
<212> TYPE: DNA
<213> ORGANISM: Homo sapiens

<400> SEQUENCE: 7
gtcttgtaac cagatacatc gtgcgttatg tga                               33

<210> SEQ ID NO 8
<211> LENGTH: 14
<212> TYPE: DNA
<213> ORGANISM: Homo sapiens

<400> SEQUENCE: 8
ggaccgagct cgtg                                                    14

<210> SEQ ID NO 9
<211> LENGTH: 15
<212> TYPE: DNA
<213> ORGANISM: Homo sapiens

<400> SEQUENCE: 9
accaacggga ccgag                                                   15

<210> SEQ ID NO 10
<211> LENGTH: 14
<212> TYPE: DNA
<213> ORGANISM: Homo sapiens

<400> SEQUENCE: 10
aacgggaccg agcg                                                    14

<210> SEQ ID NO 11
<211> LENGTH: 15
<212> TYPE: DNA
<213> ORGANISM: Homo sapiens

<400> SEQUENCE: 11
gcctagcgcc gagta                                                   15

<210> SEQ ID NO 12
<211> LENGTH: 14
<212> TYPE: DNA
<213> ORGANISM: Homo sapiens

<400> SEQUENCE: 12
tggggctgcc tgcc                                                    14

<210> SEQ ID NO 13
<211> LENGTH: 14
<212> TYPE: DNA
<213> ORGANISM: Homo sapiens

<400> SEQUENCE: 13
gtgggggagt tccg                                                    14

<210> SEQ ID NO 14
<211> LENGTH: 14
```

```
<212> TYPE: DNA
<213> ORGANISM: Homo sapiens

<400> SEQUENCE: 14
tgcctgacgc cgag                                                      14

<210> SEQ ID NO 15
<211> LENGTH: 15
<212> TYPE: DNA
<213> ORGANISM: Homo sapiens

<400> SEQUENCE: 15
gcttgacgcc gagta                                                     15

<210> SEQ ID NO 16
<211> LENGTH: 16
<212> TYPE: DNA
<213> ORGANISM: Homo sapiens

<400> SEQUENCE: 16
cgacgtggag gtgtac                                                    16

<210> SEQ ID NO 17
<211> LENGTH: 15
<212> TYPE: DNA
<213> ORGANISM: Homo sapiens

<400> SEQUENCE: 17
aggaggacgt gcgct                                                     15

<210> SEQ ID NO 18
<211> LENGTH: 15
<212> TYPE: DNA
<213> ORGANISM: Homo sapiens

<400> SEQUENCE: 18
tatcgggcgg tgacc                                                     15

<210> SEQ ID NO 19
<211> LENGTH: 15
<212> TYPE: DNA
<213> ORGANISM: Homo sapiens

<400> SEQUENCE: 19
gtgagcagaa gcatc                                                     15

<210> SEQ ID NO 20
<211> LENGTH: 17
<212> TYPE: DNA
<213> ORGANISM: Homo sapiens

<400> SEQUENCE: 20
ccgagaagag tacgtgc                                                   17

<210> SEQ ID NO 21
<211> LENGTH: 16
<212> TYPE: DNA
<213> ORGANISM: Homo sapiens

<400> SEQUENCE: 21
gtggacagag tgtgca                                                    16

<210> SEQ ID NO 22
```

```
<211> LENGTH: 14
<212> TYPE: DNA
<213> ORGANISM: Homo sapiens

<400> SEQUENCE: 22
cgcctgccgc cgag                                                       14

<210> SEQ ID NO 23
<211> LENGTH: 14
<212> TYPE: DNA
<213> ORGANISM: Homo sapiens

<400> SEQUENCE: 23
cgcctgacgc cgag                                                       14

<210> SEQ ID NO 24
<211> LENGTH: 14
<212> TYPE: DNA
<213> ORGANISM: Homo sapiens

<400> SEQUENCE: 24
taccgggcag tgac                                                       14

<210> SEQ ID NO 25
<211> LENGTH: 14
<212> TYPE: DNA
<213> ORGANISM: Homo sapiens

<400> SEQUENCE: 25
ctgtcgccga gtac                                                       14

<210> SEQ ID NO 26
<211> LENGTH: 15
<212> TYPE: DNA
<213> ORGANISM: Homo sapiens

<400> SEQUENCE: 26
acgtgtacca gggac                                                      15

<210> SEQ ID NO 27
<211> LENGTH: 14
<212> TYPE: DNA
<213> ORGANISM: Homo sapiens

<400> SEQUENCE: 27
gggacgacag gaat                                                       14

<210> SEQ ID NO 28
<211> LENGTH: 18
<212> TYPE: DNA
<213> ORGANISM: Homo sapiens

<400> SEQUENCE: 28
taagtgtacc agttacgg                                                   18

<210> SEQ ID NO 29
<211> LENGTH: 15
<212> TYPE: DNA
<213> ORGANISM: Homo sapiens

<400> SEQUENCE: 29
cagggactgc aggaa                                                      15
```

```
<210> SEQ ID NO 30
<211> LENGTH: 15
<212> TYPE: DNA
<213> ORGANISM: Homo sapiens

<400> SEQUENCE: 30
tacaacaggc aggag                                                      15

<210> SEQ ID NO 31
<211> LENGTH: 15
<212> TYPE: DNA
<213> ORGANISM: Homo sapiens

<400> SEQUENCE: 31
atctacaacc ggcag                                                      15

<210> SEQ ID NO 32
<211> LENGTH: 15
<212> TYPE: DNA
<213> ORGANISM: Homo sapiens

<400> SEQUENCE: 32
gacgtgggag agttc                                                      15

<210> SEQ ID NO 33
<211> LENGTH: 15
<212> TYPE: DNA
<213> ORGANISM: Homo sapiens

<400> SEQUENCE: 33
agaaggactt cctgg                                                      15

<210> SEQ ID NO 34
<211> LENGTH: 15
<212> TYPE: DNA
<213> ORGANISM: Homo sapiens

<400> SEQUENCE: 34
agaaggacaa cctgg                                                      15

<210> SEQ ID NO 35
<211> LENGTH: 16
<212> TYPE: DNA
<213> ORGANISM: Homo sapiens

<400> SEQUENCE: 35
aaggacctcc tgtagg                                                     16

<210> SEQ ID NO 36
<211> LENGTH: 14
<212> TYPE: DNA
<213> ORGANISM: Homo sapiens

<400> SEQUENCE: 36
gagaggcggg cagt                                                       14

<210> SEQ ID NO 37
<211> LENGTH: 14
<212> TYPE: DNA
<213> ORGANISM: Homo sapiens

<400> SEQUENCE: 37
aagcgggcat tgcc                                                       14
```

```
<210> SEQ ID NO 38
<211> LENGTH: 14
<212> TYPE: DNA
<213> ORGANISM: Homo sapiens

<400> SEQUENCE: 38
gggcagtgct agac                                                      14

<210> SEQ ID NO 39
<211> LENGTH: 15
<212> TYPE: DNA
<213> ORGANISM: Homo sapiens

<400> SEQUENCE: 39
aatgctaccc gttta                                                     15

<210> SEQ ID NO 40
<211> LENGTH: 14
<212> TYPE: DNA
<213> ORGANISM: Homo sapiens

<400> SEQUENCE: 40
ttacgtggac cagt                                                      14

<210> SEQ ID NO 41
<211> LENGTH: 23
<212> TYPE: DNA
<213> ORGANISM: Homo sapiens

<400> SEQUENCE: 41
gccactccag agaattacct ttt                                            23

<210> SEQ ID NO 42
<211> LENGTH: 23
<212> TYPE: DNA
<213> ORGANISM: Homo sapiens

<400> SEQUENCE: 42
ccagagaatt acgtgtacca gtt                                            23

<210> SEQ ID NO 43
<211> LENGTH: 23
<212> TYPE: DNA
<213> ORGANISM: Homo sapiens

<400> SEQUENCE: 43
ccagagaatt acgtgcacca gtt                                            23

<210> SEQ ID NO 44
<211> LENGTH: 17
<212> TYPE: DNA
<213> ORGANISM: Homo sapiens

<400> SEQUENCE: 44
cagggtcatg ggcccgc                                                   17

<210> SEQ ID NO 45
<211> LENGTH: 18
<212> TYPE: DNA
<213> ORGANISM: Homo sapiens

<400> SEQUENCE: 45
gcagggtcat gggcccga                                                  18
```

```
<210> SEQ ID NO 46
<211> LENGTH: 18
<212> TYPE: DNA
<213> ORGANISM: Homo sapiens

<400> SEQUENCE: 46
cagggtcacg gcctcgtc                                                 18

<210> SEQ ID NO 47
<211> LENGTH: 17
<212> TYPE: DNA
<213> ORGANISM: Homo sapiens

<400> SEQUENCE: 47
ttgctggaaa gatgcat                                                  17

<210> SEQ ID NO 48
<211> LENGTH: 14
<212> TYPE: DNA
<213> ORGANISM: Homo sapiens

<400> SEQUENCE: 48
gagcagaagc gggg                                                     14

<210> SEQ ID NO 49
<211> LENGTH: 15
<212> TYPE: DNA
<213> ORGANISM: Homo sapiens

<400> SEQUENCE: 49
cagtaattgt ccacc                                                    15

<210> SEQ ID NO 50
<211> LENGTH: 20
<212> TYPE: DNA
<213> ORGANISM: Homo sapiens

<400> SEQUENCE: 50
agatacttct atcaccaaga                                               20

<210> SEQ ID NO 51
<211> LENGTH: 15
<212> TYPE: DNA
<213> ORGANISM: Homo sapiens

<400> SEQUENCE: 51
cacggtgtcc acctg                                                    15

<210> SEQ ID NO 52
<211> LENGTH: 18
<212> TYPE: DNA
<213> ORGANISM: Homo sapiens

<400> SEQUENCE: 52
cagggtaagt ataagtgt                                                 18

<210> SEQ ID NO 53
<211> LENGTH: 14
<212> TYPE: DNA
<213> ORGANISM: Homo sapiens

<400> SEQUENCE: 53
```

```
agggcccgcc tgtc                                                    14

<210> SEQ ID NO 54
<211> LENGTH: 15
<212> TYPE: DNA
<213> ORGANISM: Homo sapiens

<400> SEQUENCE: 54
cttgaagcag gataa                                                   15

<210> SEQ ID NO 55
<211> LENGTH: 15
<212> TYPE: DNA
<213> ORGANISM: Homo sapiens

<400> SEQUENCE: 55
tatctgcaca gaggc                                                   15

<210> SEQ ID NO 56
<211> LENGTH: 16
<212> TYPE: DNA
<213> ORGANISM: Homo sapiens

<400> SEQUENCE: 56
ttggaggagg ttaagt                                                  16

<210> SEQ ID NO 57
<211> LENGTH: 15
<212> TYPE: DNA
<213> ORGANISM: Homo sapiens

<400> SEQUENCE: 57
aagacgcgtc cataa                                                   15

<210> SEQ ID NO 58
<211> LENGTH: 18
<212> TYPE: DNA
<213> ORGANISM: Homo sapiens

<400> SEQUENCE: 58
ttccagtact cctcatca                                                18

<210> SEQ ID NO 59
<211> LENGTH: 15
<212> TYPE: DNA
<213> ORGANISM: Homo sapiens

<400> SEQUENCE: 59
gagctcctgc gcttc                                                   15

<210> SEQ ID NO 60
<211> LENGTH: 14
<212> TYPE: DNA
<213> ORGANISM: Homo sapiens

<400> SEQUENCE: 60
ggcccgctcg tctt                                                    14

<210> SEQ ID NO 61
<211> LENGTH: 13
<212> TYPE: DNA
<213> ORGANISM: Homo sapiens

<400> SEQUENCE: 61
```

```
agtgctccgc gca                                                          13

<210> SEQ ID NO 62
<211> LENGTH: 14
<212> TYPE: DNA
<213> ORGANISM: Homo sapiens

<400> SEQUENCE: 62
tcggcccgcc tcct                                                         14

<210> SEQ ID NO 63
<211> LENGTH: 14
<212> TYPE: DNA
<213> ORGANISM: Homo sapiens

<400> SEQUENCE: 63
cgcctgctcc agga                                                         14

<210> SEQ ID NO 64
<211> LENGTH: 16
<212> TYPE: DNA
<213> ORGANISM: Homo sapiens

<400> SEQUENCE: 64
cagcctaaga gggagt                                                       16

<210> SEQ ID NO 65
<211> LENGTH: 14
<212> TYPE: DNA
<213> ORGANISM: Homo sapiens

<400> SEQUENCE: 65
aagacagggc cgcc                                                         14

<210> SEQ ID NO 66
<211> LENGTH: 15
<212> TYPE: DNA
<213> ORGANISM: Homo sapiens

<400> SEQUENCE: 66
cccggacaga tactt                                                        15

<210> SEQ ID NO 67
<211> LENGTH: 16
<212> TYPE: DNA
<213> ORGANISM: Homo sapiens

<400> SEQUENCE: 67
ggagctgctt aagtct                                                       16

<210> SEQ ID NO 68
<211> LENGTH: 15
<212> TYPE: DNA
<213> ORGANISM: Homo sapiens

<400> SEQUENCE: 68
gagttcctgc gcttc                                                        15

<210> SEQ ID NO 69
<211> LENGTH: 15
<212> TYPE: DNA
<213> ORGANISM: Homo sapiens
```

```
<400> SEQUENCE: 69
attgtccacc tggcc                                                  15

<210> SEQ ID NO 70
<211> LENGTH: 18
<212> TYPE: DNA
<213> ORGANISM: Homo sapiens

<400> SEQUENCE: 70
tggaacctga tcagatac                                               18

<210> SEQ ID NO 71
<211> LENGTH: 17
<212> TYPE: DNA
<213> ORGANISM: Homo sapiens

<400> SEQUENCE: 71
gctacaacag tgacctg                                                17

<210> SEQ ID NO 72
<211> LENGTH: 15
<212> TYPE: DNA
<213> ORGANISM: Homo sapiens

<400> SEQUENCE: 72
ttcctgcaca gagac                                                  15

<210> SEQ ID NO 73
<211> LENGTH: 15
<212> TYPE: DNA
<213> ORGANISM: Homo sapiens

<400> SEQUENCE: 73
ttcctgcaca gaggc                                                  15

<210> SEQ ID NO 74
<211> LENGTH: 16
<212> TYPE: DNA
<213> ORGANISM: Homo sapiens

<400> SEQUENCE: 74
aggaggactt gcgctt                                                 16

<210> SEQ ID NO 75
<211> LENGTH: 15
<212> TYPE: DNA
<213> ORGANISM: Homo sapiens

<400> SEQUENCE: 75
tggaacagcc agaag                                                  15

<210> SEQ ID NO 76
<211> LENGTH: 15
<212> TYPE: DNA
<213> ORGANISM: Homo sapiens

<400> SEQUENCE: 76
acgtgtacca gggac                                                  15

<210> SEQ ID NO 77
<211> LENGTH: 15
<212> TYPE: DNA
<213> ORGANISM: Homo sapiens
```

```
<400> SEQUENCE: 77
accttttcca gggac                                              15

<210> SEQ ID NO 78
<211> LENGTH: 14
<212> TYPE: DNA
<213> ORGANISM: Homo sapiens

<400> SEQUENCE: 78
gggacgacag gaat                                               14

<210> SEQ ID NO 79
<211> LENGTH: 16
<212> TYPE: DNA
<213> ORGANISM: Homo sapiens

<400> SEQUENCE: 79
gtaccagtta cggcag                                             16

<210> SEQ ID NO 80
<211> LENGTH: 31
<212> TYPE: DNA
<213> ORGANISM: Homo sapiens

<400> SEQUENCE: 80
gtgcaccagt tacggttacg tggaccagtt a                            31

<210> SEQ ID NO 81
<211> LENGTH: 14
<212> TYPE: DNA
<213> ORGANISM: Homo sapiens

<400> SEQUENCE: 81
gagtacgcgc gctt                                               14

<210> SEQ ID NO 82
<211> LENGTH: 14
<212> TYPE: DNA
<213> ORGANISM: Homo sapiens

<400> SEQUENCE: 82
gagttcgtgc gctt                                               14

<210> SEQ ID NO 83
<211> LENGTH: 14
<212> TYPE: DNA
<213> ORGANISM: Homo sapiens

<400> SEQUENCE: 83
gagctcgtgc gctt                                               14

<210> SEQ ID NO 84
<211> LENGTH: 14
<212> TYPE: DNA
<213> ORGANISM: Homo sapiens

<400> SEQUENCE: 84
gagttcgcgc gctt                                               14

<210> SEQ ID NO 85
<211> LENGTH: 15
<212> TYPE: DNA
```

```
<213> ORGANISM: Homo sapiens

<400> SEQUENCE: 85
tacaaccggc aggag                                            15

<210> SEQ ID NO 86
<211> LENGTH: 15
<212> TYPE: DNA
<213> ORGANISM: Homo sapiens

<400> SEQUENCE: 86
tacaacaggc aggag                                            15

<210> SEQ ID NO 87
<211> LENGTH: 14
<212> TYPE: DNA
<213> ORGANISM: Homo sapiens

<400> SEQUENCE: 87
tgctgcggag tact                                             14

<210> SEQ ID NO 88
<211> LENGTH: 17
<212> TYPE: DNA
<213> ORGANISM: Homo sapiens

<400> SEQUENCE: 88
gcctgatgag gagtact                                          17

<210> SEQ ID NO 89
<211> LENGTH: 16
<212> TYPE: DNA
<213> ORGANISM: Homo sapiens

<400> SEQUENCE: 89
cctgacgagg agtact                                           16

<210> SEQ ID NO 90
<211> LENGTH: 15
<212> TYPE: DNA
<213> ORGANISM: Homo sapiens

<400> SEQUENCE: 90
ctgaggcgga gtact                                            15

<210> SEQ ID NO 91
<211> LENGTH: 17
<212> TYPE: DNA
<213> ORGANISM: Homo sapiens

<400> SEQUENCE: 91
gcctgatgag gactact                                          17

<210> SEQ ID NO 92
<211> LENGTH: 15
<212> TYPE: DNA
<213> ORGANISM: Homo sapiens

<400> SEQUENCE: 92
gaaggacatc ctgga                                            15

<210> SEQ ID NO 93
<211> LENGTH: 14
```

```
<212> TYPE: DNA
<213> ORGANISM: Homo sapiens

<400> SEQUENCE: 93
aaggacctcc tgga                                                       14

<210> SEQ ID NO 94
<211> LENGTH: 15
<212> TYPE: DNA
<213> ORGANISM: Homo sapiens

<400> SEQUENCE: 94
agaaggactt cctgg                                                      15

<210> SEQ ID NO 95
<211> LENGTH: 15
<212> TYPE: DNA
<213> ORGANISM: Homo sapiens

<400> SEQUENCE: 95
agaaggacaa cctgg                                                      15

<210> SEQ ID NO 96
<211> LENGTH: 14
<212> TYPE: DNA
<213> ORGANISM: Homo sapiens

<400> SEQUENCE: 96
gagaagcggg cagt                                                       14

<210> SEQ ID NO 97
<211> LENGTH: 14
<212> TYPE: DNA
<213> ORGANISM: Homo sapiens

<400> SEQUENCE: 97
gaggagcggg cagt                                                       14

<210> SEQ ID NO 98
<211> LENGTH: 14
<212> TYPE: DNA
<213> ORGANISM: Homo sapiens

<400> SEQUENCE: 98
gagaggcggg cagt                                                       14

<210> SEQ ID NO 99
<211> LENGTH: 14
<212> TYPE: DNA
<213> ORGANISM: Homo sapiens

<400> SEQUENCE: 99
gcattgccgg acag                                                       14

<210> SEQ ID NO 100
<211> LENGTH: 15
<212> TYPE: DNA
<213> ORGANISM: Homo sapiens

<400> SEQUENCE: 100
gcagtgctgg acagg                                                      15

<210> SEQ ID NO 101
```

```
<211> LENGTH: 15
<212> TYPE: DNA
<213> ORGANISM: Homo sapiens

<400> SEQUENCE: 101
cagggtatgc agaca                                                    15

<210> SEQ ID NO 102
<211> LENGTH: 16
<212> TYPE: DNA
<213> ORGANISM: Homo sapiens

<400> SEQUENCE: 102
acaggatatg cagaca                                                   16

<210> SEQ ID NO 103
<211> LENGTH: 15
<212> TYPE: DNA
<213> ORGANISM: Homo sapiens

<400> SEQUENCE: 103
acaggatgtg cagac                                                    15

<210> SEQ ID NO 104
<211> LENGTH: 15
<212> TYPE: DNA
<213> ORGANISM: Homo sapiens

<400> SEQUENCE: 104
tacgagctgg acgag                                                    15

<210> SEQ ID NO 105
<211> LENGTH: 14
<212> TYPE: DNA
<213> ORGANISM: Homo sapiens

<400> SEQUENCE: 105
tacgagctgg gcgg                                                     14

<210> SEQ ID NO 106
<211> LENGTH: 14
<212> TYPE: DNA
<213> ORGANISM: Homo sapiens

<400> SEQUENCE: 106
tacgagctgg tcgg                                                     14

<210> SEQ ID NO 107
<211> LENGTH: 16
<212> TYPE: DNA
<213> ORGANISM: Homo sapiens

<400> SEQUENCE: 107
aaggacctcc tgtagg                                                   16

<210> SEQ ID NO 108
<211> LENGTH: 15
<212> TYPE: DNA
<213> ORGANISM: Homo sapiens

<400> SEQUENCE: 108
cagggactgc aggaa                                                    15
```

<210> SEQ ID NO 109
<211> LENGTH: 15
<212> TYPE: DNA
<213> ORGANISM: Homo sapiens

<400> SEQUENCE: 109
aatgctaccc gttta                                                        15

<210> SEQ ID NO 110
<211> LENGTH: 23
<212> TYPE: DNA
<213> ORGANISM: Homo sapiens

<400> SEQUENCE: 110
gccactccag agaattacct ttt                                               23

<210> SEQ ID NO 111
<211> LENGTH: 23
<212> TYPE: DNA
<213> ORGANISM: Homo sapiens

<400> SEQUENCE: 111
ccagagaatt acgtgtacca gtt                                               23

<210> SEQ ID NO 112
<211> LENGTH: 23
<212> TYPE: DNA
<213> ORGANISM: Homo sapiens

<400> SEQUENCE: 112
ccagagaatt acgtgcacca gtt                                               23

<210> SEQ ID NO 113
<211> LENGTH: 17
<212> TYPE: DNA
<213> ORGANISM: Homo sapiens

<400> SEQUENCE: 113
cagggtcatg ggcccgc                                                      17

<210> SEQ ID NO 114
<211> LENGTH: 18
<212> TYPE: DNA
<213> ORGANISM: Homo sapiens

<400> SEQUENCE: 114
gcagggtcat gggcccga                                                     18

<210> SEQ ID NO 115
<211> LENGTH: 18
<212> TYPE: DNA
<213> ORGANISM: Homo sapiens

<400> SEQUENCE: 115
cagggtcacg gcctcgtc                                                     18

<210> SEQ ID NO 116
<211> LENGTH: 20
<212> TYPE: DNA
<213> ORGANISM: Human papillomavirus
<220> FEATURE:
<223> OTHER INFORMATION: Nucleotide sequence in L1 region

<400> SEQUENCE: 116
gcmcagggwc ataayaatgg                                               20

<210> SEQ ID NO 117
<211> LENGTH: 20
<212> TYPE: DNA
<213> ORGANISM: Human papillomavirus
<220> FEATURE:
<223> OTHER INFORMATION: Nucleotide sequence in L1 region

<400> SEQUENCE: 117
cgtccmarrg gawactgatc                                               20

<210> SEQ ID NO 118
<211> LENGTH: 20
<212> TYPE: DNA
<213> ORGANISM: Human papillomavirus
<220> FEATURE:
<223> OTHER INFORMATION: Nucleotide sequence in L1 region

<400> SEQUENCE: 118
gcgacccaat gcaaattggt                                               20

<210> SEQ ID NO 119
<211> LENGTH: 21
<212> TYPE: DNA
<213> ORGANISM: Homo sapiens

<400> SEQUENCE: 119
gtgcacctga ctcctgagga g                                             21

<210> SEQ ID NO 120
<211> LENGTH: 21
<212> TYPE: DNA
<213> ORGANISM: Homo sapiens

<400> SEQUENCE: 120
ccttgatacc aacctgccca g                                             21

<210> SEQ ID NO 121
<211> LENGTH: 22
<212> TYPE: DNA
<213> ORGANISM: Human papillomavirus
<220> FEATURE:
<223> OTHER INFORMATION: Human papillomavirus type 11

<400> SEQUENCE: 121
atctgtgtct aaatctgcta ca                                            22

<210> SEQ ID NO 122
<211> LENGTH: 26
<212> TYPE: DNA
<213> ORGANISM: Human papillomavirus
<220> FEATURE:
<223> OTHER INFORMATION: Human papillomavirus type 11

<400> SEQUENCE: 122
gtacatatct ataagtatcc tccagt                                        26

<210> SEQ ID NO 123
<211> LENGTH: 23
<212> TYPE: DNA
<213> ORGANISM: Human papillomavirus
<220> FEATURE:
<223> OTHER INFORMATION: Human papillomavirus type 16

<400> SEQUENCE: 123

-continued gccatatcta cttcagaaac tac                                    23

<210> SEQ ID NO 124
<211> LENGTH: 19
<212> TYPE: DNA
<213> ORGANISM: Human papillomavirus
<220> FEATURE:
<223> OTHER INFORMATION: Human papillomavirus type 18

<400> SEQUENCE: 124
tgcttctaca cagtctcct                                         19

<210> SEQ ID NO 125
<211> LENGTH: 21
<212> TYPE: DNA
<213> ORGANISM: Human papillomavirus
<220> FEATURE:
<223> OTHER INFORMATION: Human papillomavirus type 18

<400> SEQUENCE: 125
tattttcagc cggtgcagca t                                      21

<210> SEQ ID NO 126
<211> LENGTH: 15
<212> TYPE: DNA
<213> ORGANISM: Human papillomavirus
<220> FEATURE:
<223> OTHER INFORMATION: Human papillomavirus type 26

<400> SEQUENCE: 126
gcatctgcat ccact                                             15

<210> SEQ ID NO 127
<211> LENGTH: 20
<212> TYPE: DNA
<213> ORGANISM: Human papillomavirus
<220> FEATURE:
<223> OTHER INFORMATION: Human papillomavirus type 31

<400> SEQUENCE: 127
gcaattgcaa acagtgatac                                        20

<210> SEQ ID NO 128
<211> LENGTH: 20
<212> TYPE: DNA
<213> ORGANISM: Human papillomavirus
<220> FEATURE:
<223> OTHER INFORMATION: Human papillomavirus type 31

<400> SEQUENCE: 128
gatcttcctt gggcttttgg                                        20

<210> SEQ ID NO 129
<211> LENGTH: 20
<212> TYPE: DNA
<213> ORGANISM: Human papillomavirus
<220> FEATURE:
<223> OTHER INFORMATION: Human papillomavirus type 33

<400> SEQUENCE: 129
tgcacacaag taactagtga                                        20

<210> SEQ ID NO 130
<211> LENGTH: 21
<212> TYPE: DNA

```
<213> ORGANISM: Human papillomavirus
<220> FEATURE:
<223> OTHER INFORMATION: Human papillomavirus type 33

<400> SEQUENCE: 130
tttggaggta ctgtttttg a                                              21

<210> SEQ ID NO 131
<211> LENGTH: 19
<212> TYPE: DNA
<213> ORGANISM: Human papillomavirus
<220> FEATURE:
<223> OTHER INFORMATION: Human papillomavirus type 35

<400> SEQUENCE: 131
ctgctgtgtc ttctagtga                                                19

<210> SEQ ID NO 132
<211> LENGTH: 20
<212> TYPE: DNA
<213> ORGANISM: Human papillomavirus
<220> FEATURE:
<223> OTHER INFORMATION: Human papillomavirus type 39

<400> SEQUENCE: 132
tacattacta cctctataga                                               20

<210> SEQ ID NO 133
<211> LENGTH: 24
<212> TYPE: DNA
<213> ORGANISM: Human papillomavirus
<220> FEATURE:
<223> OTHER INFORMATION: Human papillomavirus type 39

<400> SEQUENCE: 133
gcagactgta ggtatctgta agtg                                          24

<210> SEQ ID NO 134
<211> LENGTH: 20
<212> TYPE: DNA
<213> ORGANISM: Human papillomavirus
<220> FEATURE:
<223> OTHER INFORMATION: Human papillomavirus type 40

<400> SEQUENCE: 134
ccacaccaac cccatataat                                               20

<210> SEQ ID NO 135
<211> LENGTH: 19
<212> TYPE: DNA
<213> ORGANISM: Human papillomavirus
<220> FEATURE:
<223> OTHER INFORMATION: Human papillomavirus type 42

<400> SEQUENCE: 135
gccactgcaa catctggtg                                                19

<210> SEQ ID NO 136
<211> LENGTH: 20
<212> TYPE: DNA
<213> ORGANISM: Human papillomavirus
<220> FEATURE:
<223> OTHER INFORMATION: Human papillomavirus type 42

<400> SEQUENCE: 136
gcgttgttac cttagcctga                                               20
```

<210> SEQ ID NO 137
<211> LENGTH: 18
<212> TYPE: DNA
<213> ORGANISM: Human papillomavirus
<220> FEATURE:
<223> OTHER INFORMATION: Human papillomavirus type 43

<400> SEQUENCE: 137
tctactgacc ctactgtg                                                 18

<210> SEQ ID NO 138
<211> LENGTH: 21
<212> TYPE: DNA
<213> ORGANISM: Human papillomavirus
<220> FEATURE:
<223> OTHER INFORMATION: Human papillomavirus type 44

<400> SEQUENCE: 138
tactagtgaa caatataagc a                                             21

<210> SEQ ID NO 139
<211> LENGTH: 21
<212> TYPE: DNA
<213> ORGANISM: Human papillomavirus
<220> FEATURE:
<223> OTHER INFORMATION: Human papillomavirus type 44

<400> SEQUENCE: 139
ttaattttgc atagggtcc t                                              21

<210> SEQ ID NO 140
<211> LENGTH: 21
<212> TYPE: DNA
<213> ORGANISM: Human papillomavirus
<220> FEATURE:
<223> OTHER INFORMATION: Human papillomavirus type 45

<400> SEQUENCE: 140
taatttaaca ttatgtgcct c                                             21

<210> SEQ ID NO 141
<211> LENGTH: 23
<212> TYPE: DNA
<213> ORGANISM: Human papillomavirus
<220> FEATURE:
<223> OTHER INFORMATION: Human papillomavirus type 51

<400> SEQUENCE: 141
cccaacattt actccaagt aact                                           23

<210> SEQ ID NO 142
<211> LENGTH: 21
<212> TYPE: DNA
<213> ORGANISM: Human papillomavirus
<220> FEATURE:
<223> OTHER INFORMATION: Human papillomavirus type 51

<400> SEQUENCE: 142
ctgttcaaga atggtaggat c                                             21

<210> SEQ ID NO 143
<211> LENGTH: 30
<212> TYPE: DNA
<213> ORGANISM: Human papillomavirus
<220> FEATURE:

<223> OTHER INFORMATION: Human papillomavirus type 52

<400> SEQUENCE: 143
tgctgaggtt aaaaaggaaa gcacatataa                                30

<210> SEQ ID NO 144
<211> LENGTH: 19
<212> TYPE: DNA
<213> ORGANISM: Human papillomavirus
<220> FEATURE:
<223> OTHER INFORMATION: Human papillomavirus type 53

<400> SEQUENCE: 144
ccacacagtc tatgtctac                                            19

<210> SEQ ID NO 145
<211> LENGTH: 22
<212> TYPE: DNA
<213> ORGANISM: Human papillomavirus
<220> FEATURE:
<223> OTHER INFORMATION: Human papillomavirus type 53

<400> SEQUENCE: 145
ccagtcttcc agtaaggtag aa                                        22

<210> SEQ ID NO 146
<211> LENGTH: 18
<212> TYPE: DNA
<213> ORGANISM: Human papillomavirus
<220> FEATURE:
<223> OTHER INFORMATION: Human papillomavirus type 54

<400> SEQUENCE: 146
attgtgtgct acagcatc                                             18

<210> SEQ ID NO 147
<211> LENGTH: 20
<212> TYPE: DNA
<213> ORGANISM: Human papillomavirus
<220> FEATURE:
<223> OTHER INFORMATION: Human papillomavirus type 55

<400> SEQUENCE: 147
acaactcagt ctccatctac                                           20

<210> SEQ ID NO 148
<211> LENGTH: 21
<212> TYPE: DNA
<213> ORGANISM: Human papillomavirus
<220> FEATURE:
<223> OTHER INFORMATION: Human papillomavirus type 56

<400> SEQUENCE: 148
gatgcacgaa aaattaatca g                                         21

<210> SEQ ID NO 149
<211> LENGTH: 20
<212> TYPE: DNA
<213> ORGANISM: Human papillomavirus
<220> FEATURE:
<223> OTHER INFORMATION: Human papillomavirus type 56

<400> SEQUENCE: 149
tcctccagta ggttagcatt                                           20

```
<210> SEQ ID NO 150
<211> LENGTH: 22
<212> TYPE: DNA
<213> ORGANISM: Human papillomavirus
<220> FEATURE:
<223> OTHER INFORMATION: Human papillomavirus type 57

<400> SEQUENCE: 150
ccactgtaac cacagaaact aa                                              22

<210> SEQ ID NO 151
<211> LENGTH: 23
<212> TYPE: DNA
<213> ORGANISM: Human papillomavirus
<220> FEATURE:
<223> OTHER INFORMATION: Human papillomavirus type 58

<400> SEQUENCE: 151
actgaagtaa ctaaggaagg tac                                             23

<210> SEQ ID NO 152
<211> LENGTH: 19
<212> TYPE: DNA
<213> ORGANISM: Human papillomavirus
<220> FEATURE:
<223> OTHER INFORMATION: Human papillomavirus type 59

<400> SEQUENCE: 152
agaatatgcc agacatgtg                                                  19

<210> SEQ ID NO 153
<211> LENGTH: 18
<212> TYPE: DNA
<213> ORGANISM: Human papillomavirus
<220> FEATURE:
<223> OTHER INFORMATION: Human papillomavirus type 59

<400> SEQUENCE: 153
gggtcctgtt taactggc                                                   18

<210> SEQ ID NO 154
<211> LENGTH: 20
<212> TYPE: DNA
<213> ORGANISM: Human papillomavirus
<220> FEATURE:
<223> OTHER INFORMATION: Human papillomavirus type 6

<400> SEQUENCE: 154
catccgtaac tacatcttcc                                                 20

<210> SEQ ID NO 155
<211> LENGTH: 23
<212> TYPE: DNA
<213> ORGANISM: Human papillomavirus
<220> FEATURE:
<223> OTHER INFORMATION: Human papillomavirus type 61

<400> SEQUENCE: 155
cctgtatctg aatataaagc cac                                             23

<210> SEQ ID NO 156
<211> LENGTH: 22
<212> TYPE: DNA
<213> ORGANISM: Human papillomavirus
<220> FEATURE:
<223> OTHER INFORMATION: Human papillomavirus type 66
```

-continued

```
<400> SEQUENCE: 156
cgtgaaatca atcaatacct tc                                              22

<210> SEQ ID NO 157
<211> LENGTH: 29
<212> TYPE: DNA
<213> ORGANISM: Human papillomavirus
<220> FEATURE:
<223> OTHER INFORMATION: Human papillomavirus type 66

<400> SEQUENCE: 157
cgtctaataa agtattattc atattatgc                                       29

<210> SEQ ID NO 158
<211> LENGTH: 19
<212> TYPE: DNA
<213> ORGANISM: Human papillomavirus
<220> FEATURE:
<223> OTHER INFORMATION: Human papillomavirus type 68

<400> SEQUENCE: 158
ctgaatcagc tgtaccaaa                                                  19

<210> SEQ ID NO 159
<211> LENGTH: 20
<212> TYPE: DNA
<213> ORGANISM: Human papillomavirus
<220> FEATURE:
<223> OTHER INFORMATION: Human papillomavirus type 70

<400> SEQUENCE: 159
gccatacctg ctgtatatag                                                 20

<210> SEQ ID NO 160
<211> LENGTH: 20
<212> TYPE: DNA
<213> ORGANISM: Human papillomavirus
<220> FEATURE:
<223> OTHER INFORMATION: Human papillomavirus type 71

<400> SEQUENCE: 160
gctaccaaaa ctgttgagtc                                                 20

<210> SEQ ID NO 161
<211> LENGTH: 17
<212> TYPE: DNA
<213> ORGANISM: Human papillomavirus
<220> FEATURE:
<223> OTHER INFORMATION: Human papillomavirus type 72

<400> SEQUENCE: 161
cagcgtcctc tgtatca                                                    17

<210> SEQ ID NO 162
<211> LENGTH: 21
<212> TYPE: DNA
<213> ORGANISM: Human papillomavirus
<220> FEATURE:
<223> OTHER INFORMATION: Human papillomavirus type 73

<400> SEQUENCE: 162
gtatgccaac tcwaatttta a                                               21

<210> SEQ ID NO 163
<211> LENGTH: 30
```

```
<212> TYPE: DNA
<213> ORGANISM: Human papillomavirus
<220> FEATURE:
<223> OTHER INFORMATION: Human papillomavirus type 81

<400> SEQUENCE: 163
gcacagctac atctgatgct gcagaataca                                        30

<210> SEQ ID NO 164
<211> LENGTH: 20
<212> TYPE: DNA
<213> ORGANISM: Human papillomavirus
<220> FEATURE:
<223> OTHER INFORMATION: Human papillomavirus type 81

<400> SEQUENCE: 164
gaacaaggca ctgttggatg                                                   20

<210> SEQ ID NO 165
<211> LENGTH: 20
<212> TYPE: DNA
<213> ORGANISM: Human papillomavirus
<220> FEATURE:
<223> OTHER INFORMATION: Human papillomavirus type 82

<400> SEQUENCE: 165
tactccatct gttgcacaaa                                                   20

<210> SEQ ID NO 166
<211> LENGTH: 18
<212> TYPE: DNA
<213> ORGANISM: Human papillomavirus
<220> FEATURE:
<223> OTHER INFORMATION: Human papillomavirus type 82

<400> SEQUENCE: 166
acaggatgtt gctgcatt                                                     18

<210> SEQ ID NO 167
<211> LENGTH: 19
<212> TYPE: DNA
<213> ORGANISM: Human papillomavirus
<220> FEATURE:
<223> OTHER INFORMATION: Human papillomavirus type 84

<400> SEQUENCE: 167
ctaccaacac cgaatcaga                                                    19

<210> SEQ ID NO 168
<211> LENGTH: 26
<212> TYPE: DNA
<213> ORGANISM: Homo sapiens

<400> SEQUENCE: 168
aaggtgaacg aggatgaagt tggtgg                                            26

<210> SEQ ID NO 169
<211> LENGTH: 19
<212> TYPE: DNA
<213> ORGANISM: Artificial sequence
<220> FEATURE:
<223> OTHER INFORMATION: A random synthetic nongenus nucleotide sequence

<400> SEQUENCE: 169
gttccaacta ggaacatca                                                    19
```

<210> SEQ ID NO 170
<211> LENGTH: 36
<212> TYPE: DNA
<213> ORGANISM: Artificial sequence
<220> FEATURE:
<223> OTHER INFORMATION: Papillomaviridae nucleotide sequence with
      modified bases
<220> FEATURE:
<221> NAME/KEY: misc_feature
<222> LOCATION: (6)...(6)
<223> OTHER INFORMATION: n represents inosine
<220> FEATURE:
<221> NAME/KEY: misc_feature
<222> LOCATION: (12)...(12)
<223> OTHER INFORMATION: n represents LNA modified base A
<220> FEATURE:
<221> NAME/KEY: misc_feature
<222> LOCATION: (27)...(27)
<223> OTHER INFORMATION: n represents LNA modified base T
<220> FEATURE:
<221> NAME/KEY: misc_feature
<222> LOCATION: (32)...(32)
<223> OTHER INFORMATION: n represents LNA modified base T

<400> SEQUENCE: 170
catgbnggag gngtttgatt tacaatntat gnttca                                 36

<210> SEQ ID NO 171
<211> LENGTH: 29
<212> TYPE: DNA
<213> ORGANISM: Artificial Sequence
<220> FEATURE:
<223> OTHER INFORMATION: Papillomaviridae nucleotide sequence with
      modified bases
<220> FEATURE:
<221> NAME/KEY: misc_feature
<222> LOCATION: (9)...(9)
<223> OTHER INFORMATION: n represent LNA modified base T
<220> FEATURE:
<221> NAME/KEY: misc_feature
<222> LOCATION: (25)...(25)
<223> OTHER INFORMATION: n represents LNA modified base T

<400> SEQUENCE: 171
gaagagtang atttgcaatt tatanttca                                         29

<210> SEQ ID NO 172
<211> LENGTH: 23
<212> TYPE: DNA
<213> ORGANISM: Artificial Sequence
<220> FEATURE:
<223> OTHER INFORMATION: Papillomaviridae nucleotide sequence with
      modified bases
<220> FEATURE:
<221> NAME/KEY: misc_feature
<222> LOCATION: (5)...(5)
<223> OTHER INFORMATION: n represents LNA modified base T
<220> FEATURE:
<221> NAME/KEY: misc_feature
<222> LOCATION: (19)...(19)
<223> OTHER INFORMATION: n represents LNA modified base A

<400> SEQUENCE: 172
tttgntactg tggtagatnc tac                                               23

<210> SEQ ID NO 173
<211> LENGTH: 25
<212> TYPE: DNA
<213> ORGANISM: Artificial Sequence
<220> FEATURE:
<223> OTHER INFORMATION: Papillomaviridae nucleotide sequence with
      modified bases

```
<220> FEATURE:
<221> NAME/KEY: misc_feature
<222> LOCATION: (3)...(3)
<223> OTHER INFORMATION: n represents LNA modified base A
<220> FEATURE:
<221> NAME/KEY: misc_feature
<222> LOCATION: (9)...(9)
<223> OTHER INFORMATION: n represents LNA modified base A
<220> FEATURE:
<221> NAME/KEY: misc_feature
<222> LOCATION: (24)...(24)
<223> OTHER INFORMATION: n represents LNA modified base T

<400> SEQUENCE: 173
ganaaatana ctgtaaatca tatnc                                           25

<210> SEQ ID NO 174
<211> LENGTH: 20
<212> TYPE: DNA
<213> ORGANISM: Artificial sequence
<220> FEATURE:
<223> OTHER INFORMATION: Primer

<400> SEQUENCE: 174
tcaacatccg gccggtggtc                                                 20

<210> SEQ ID NO 175
<211> LENGTH: 21
<212> TYPE: DNA
<213> ORGANISM: Artificial sequence
<220> FEATURE:
<223> OTHER INFORMATION: Primer

<400> SEQUENCE: 175
ccggcacgct cacgtgacag a                                               21

<210> SEQ ID NO 176
<211> LENGTH: 21
<212> TYPE: DNA
<213> ORGANISM: Artificial sequence
<220> FEATURE:
<223> OTHER INFORMATION: Primer

<400> SEQUENCE: 176
tggcaccgga accggtaagg a                                               21

<210> SEQ ID NO 177
<211> LENGTH: 19
<212> TYPE: DNA
<213> ORGANISM: Artificial sequence
<220> FEATURE:
<223> OTHER INFORMATION: Primer

<400> SEQUENCE: 177
cgccagcagg gctcttcgt                                                  19

<210> SEQ ID NO 178
<211> LENGTH: 22
<212> TYPE: DNA
<213> ORGANISM: Artificial sequence
<220> FEATURE:
<223> OTHER INFORMATION: Primer

<400> SEQUENCE: 178
aagttcccgc cggaaatcgc ag                                              22

<210> SEQ ID NO 179
```

```
<211> LENGTH: 24
<212> TYPE: DNA
<213> ORGANISM: Artificial sequence
<220> FEATURE:
<223> OTHER INFORMATION: Primer

<400> SEQUENCE: 179
ccggtaacca ggactgaacg ggat                                            24

<210> SEQ ID NO 180
<211> LENGTH: 19
<212> TYPE: DNA
<213> ORGANISM: Artificial sequence
<220> FEATURE:
<223> OTHER INFORMATION: Primer

<400> SEQUENCE: 180
cgagttcccg cccataacc                                                  19

<210> SEQ ID NO 181
<211> LENGTH: 19
<212> TYPE: DNA
<213> ORGANISM: Artificial sequence
<220> FEATURE:
<223> OTHER INFORMATION: Primer

<400> SEQUENCE: 181
ggaagttgca acgccgtcc                                                  19

<210> SEQ ID NO 182
<211> LENGTH: 15
<212> TYPE: DNA
<213> ORGANISM: Artificial sequence
<220> FEATURE:
<223> OTHER INFORMATION: Probe

<400> SEQUENCE: 182
gctggtgccg aagaa                                                      15

<210> SEQ ID NO 183
<211> LENGTH: 18
<212> TYPE: DNA
<213> ORGANISM: Artificial sequence
<220> FEATURE:
<223> OTHER INFORMATION: Probe

<400> SEQUENCE: 183
cggggtgttc gtccatac                                                   18

<210> SEQ ID NO 184
<211> LENGTH: 20
<212> TYPE: DNA
<213> ORGANISM: Artificial sequence
<220> FEATURE:
<223> OTHER INFORMATION: Probe

<400> SEQUENCE: 184
ggtatgtcca cgagcgtaac                                                 20

<210> SEQ ID NO 185
<211> LENGTH: 17
<212> TYPE: DNA
<213> ORGANISM: Artificial sequence
<220> FEATURE:
<223> OTHER INFORMATION: Probe

<400> SEQUENCE: 185
```

```
ggttgttctg gtccatg                                                    17

<210> SEQ ID NO 186
<211> LENGTH: 17
<212> TYPE: DNA
<213> ORGANISM: Artificial sequence
<220> FEATURE:
<223> OTHER INFORMATION: Probe

<400> SEQUENCE: 186
tgacccacaa gcgccga                                                    17

<210> SEQ ID NO 187
<211> LENGTH: 15
<212> TYPE: DNA
<213> ORGANISM: Artificial sequence
<220> FEATURE:
<223> OTHER INFORMATION: Probe

<400> SEQUENCE: 187
gactgtcggc gctgg                                                      15

<210> SEQ ID NO 188
<211> LENGTH: 17
<212> TYPE: DNA
<213> ORGANISM: Artificial sequence
<220> FEATURE:
<223> OTHER INFORMATION: Probe

<400> SEQUENCE: 188
gatgccgctg gtgatcg                                                    17

<210> SEQ ID NO 189
<211> LENGTH: 17
<212> TYPE: DNA
<213> ORGANISM: Artificial sequence
<220> FEATURE:
<223> OTHER INFORMATION: Probe

<400> SEQUENCE: 189
aacctatcgt ctcgccg                                                    17

<210> SEQ ID NO 190
<211> LENGTH: 18
<212> TYPE: DNA
<213> ORGANISM: Artificial sequence
<220> FEATURE:
<223> OTHER INFORMATION: Probe

<400> SEQUENCE: 190
ggttgttctg gaccatga                                                   18

<210> SEQ ID NO 191
<211> LENGTH: 17
<212> TYPE: DNA
<213> ORGANISM: Artificial sequence
<220> FEATURE:
<223> OTHER INFORMATION: Probe

<400> SEQUENCE: 191
ggttgttctg gcccatg                                                    17

<210> SEQ ID NO 192
<211> LENGTH: 16
<212> TYPE: DNA
```

```
<213> ORGANISM: Artificial sequence
<220> FEATURE:
<223> OTHER INFORMATION: Probe

<400> SEQUENCE: 192
gaccgacaag cgccga                                                    16

<210> SEQ ID NO 193
<211> LENGTH: 17
<212> TYPE: DNA
<213> ORGANISM: Artificial sequence
<220> FEATURE:
<223> OTHER INFORMATION: Probe

<400> SEQUENCE: 193
gcgcttgtag gtcaacc                                                   17

<210> SEQ ID NO 194
<211> LENGTH: 16
<212> TYPE: DNA
<213> ORGANISM: Artificial sequence
<220> FEATURE:
<223> OTHER INFORMATION: Probe

<400> SEQUENCE: 194
gcgcttgagg gtcaac                                                    16

<210> SEQ ID NO 195
<211> LENGTH: 16
<212> TYPE: DNA
<213> ORGANISM: Artificial sequence
<220> FEATURE:
<223> OTHER INFORMATION: Probe

<400> SEQUENCE: 195
ccccagcgcc aacagt                                                    16

<210> SEQ ID NO 196
<211> LENGTH: 15
<212> TYPE: DNA
<213> ORGANISM: Artificial sequence
<220> FEATURE:
<223> OTHER INFORMATION: Probe

<400> SEQUENCE: 196
gactgtgggc gctgg                                                     15

<210> SEQ ID NO 197
<211> LENGTH: 16
<212> TYPE: DNA
<213> ORGANISM: Artificial sequence
<220> FEATURE:
<223> OTHER INFORMATION: Probe

<400> SEQUENCE: 197
gatgccggtg gtgatc                                                    16

<210> SEQ ID NO 198
<211> LENGTH: 17
<212> TYPE: DNA
<213> ORGANISM: Artificial sequence
<220> FEATURE:
<223> OTHER INFORMATION: Probe

<400> SEQUENCE: 198
gatgcctgtg gtgatcg                                                   17
```

```
<210> SEQ ID NO 199
<211> LENGTH: 18
<212> TYPE: DNA
<213> ORGANISM: Artificial sequence
<220> FEATURE:
<223> OTHER INFORMATION: Probe

<400> SEQUENCE: 199
caacctatca tctcgccg                                                      18

<210> SEQ ID NO 200
<211> LENGTH: 19
<212> TYPE: DNA
<213> ORGANISM: Artificial sequence
<220> FEATURE:
<223> OTHER INFORMATION: Probe

<400> SEQUENCE: 200
ctcgaatgcc tcgtatcat                                                     19

<210> SEQ ID NO 201
<211> LENGTH: 26
<212> TYPE: DNA
<213> ORGANISM: Artificial sequence
<220> FEATURE:
<223> OTHER INFORMATION: Primer

<400> SEQUENCE: 201
gtacggctgt catcacttag acctca                                             26

<210> SEQ ID NO 202
<211> LENGTH: 24
<212> TYPE: DNA
<213> ORGANISM: Artificial sequence
<220> FEATURE:
<223> OTHER INFORMATION: Primer

<400> SEQUENCE: 202 ttatccccttt cctatgacat gaac                                              24

<210> SEQ ID NO 203
<211> LENGTH: 20
<212> TYPE: DNA
<213> ORGANISM: Artificial sequence
<220> FEATURE:
<223> OTHER INFORMATION: Primer

<400> SEQUENCE: 203
gtgtacacat attgaccaaa                                                    20

<210> SEQ ID NO 204
<211> LENGTH: 18
<212> TYPE: DNA
<213> ORGANISM: Artificial sequence
<220> FEATURE:
<223> OTHER INFORMATION: Primer

<400> SEQUENCE: 204
gcaagaaagc gagcttag                                                      18

<210> SEQ ID NO 205
<211> LENGTH: 20
<212> TYPE: DNA
<213> ORGANISM: Artificial sequence
<220> FEATURE:
```

```
<223> OTHER INFORMATION: Primer

<400> SEQUENCE: 205
gtatctctaa gcaagagaac                                               20

<210> SEQ ID NO 206
<211> LENGTH: 19
<212> TYPE: DNA
<213> ORGANISM: Artificial sequence
<220> FEATURE:
<223> OTHER INFORMATION: Probe

<400> SEQUENCE: 206
agacaccatg gtgcatctg                                                19

<210> SEQ ID NO 207
<211> LENGTH: 18
<212> TYPE: DNA
<213> ORGANISM: Artificial sequence
<220> FEATURE:
<223> OTHER INFORMATION: Probe

<400> SEQUENCE: 207
agacaccatg gtgcacct                                                 18

<210> SEQ ID NO 208
<211> LENGTH: 18
<212> TYPE: DNA
<213> ORGANISM: Artificial sequence
<220> FEATURE:
<223> OTHER INFORMATION: Probe

<400> SEQUENCE: 208
caaacagaca ccagggtg                                                 18

<210> SEQ ID NO 209
<211> LENGTH: 19
<212> TYPE: DNA
<213> ORGANISM: Artificial sequence
<220> FEATURE:
<223> OTHER INFORMATION: Probe

<400> SEQUENCE: 209
gctgggcata aaagtcagg                                                19

<210> SEQ ID NO 210
<211> LENGTH: 19
<212> TYPE: DNA
<213> ORGANISM: Artificial sequence
<220> FEATURE:
<223> OTHER INFORMATION: Probe

<400> SEQUENCE: 210
cctgacttct atgcccagc                                                19

<210> SEQ ID NO 211
<211> LENGTH: 17
<212> TYPE: DNA
<213> ORGANISM: Artificial sequence
<220> FEATURE:
<223> OTHER INFORMATION: Probe

<400> SEQUENCE: 211
ccctgacttt catgccc                                                  17
```

```
<210> SEQ ID NO 212
<211> LENGTH: 18
<212> TYPE: DNA
<213> ORGANISM: Artificial sequence
<220> FEATURE:
<223> OTHER INFORMATION: Probe

<400> SEQUENCE: 212
gcatctgact cctgagga                                                 18

<210> SEQ ID NO 213
<211> LENGTH: 17
<212> TYPE: DNA
<213> ORGANISM: Artificial sequence
<220> FEATURE:
<223> OTHER INFORMATION: Probe

<400> SEQUENCE: 213
gcacctgact cctgagg                                                  17

<210> SEQ ID NO 214
<211> LENGTH: 19
<212> TYPE: DNA
<213> ORGANISM: Artificial sequence
<220> FEATURE:
<223> OTHER INFORMATION: Probe

<400> SEQUENCE: 214
acttctcctc gagtcagat                                                19

<210> SEQ ID NO 215
<211> LENGTH: 16
<212> TYPE: DNA
<213> ORGANISM: Artificial sequence
<220> FEATURE:
<223> OTHER INFORMATION: Probe

<400> SEQUENCE: 215
cagggcctca ccacca                                                   16

<210> SEQ ID NO 216
<211> LENGTH: 17
<212> TYPE: DNA
<213> ORGANISM: Artificial sequence
<220> FEATURE:
<223> OTHER INFORMATION: Probe

<400> SEQUENCE: 216
gttggtggta aggccct                                                  17

<210> SEQ ID NO 217
<211> LENGTH: 15
<212> TYPE: DNA
<213> ORGANISM: Artificial sequence
<220> FEATURE:
<223> OTHER INFORMATION: Probe

<400> SEQUENCE: 217
ccaggggcct cacca                                                    15

<210> SEQ ID NO 218
<211> LENGTH: 20
<212> TYPE: DNA
<213> ORGANISM: Artificial sequence
<220> FEATURE:
<223> OTHER INFORMATION: Probe
```

<400> SEQUENCE: 218
aggagaagtc tgccgttact                                            20

<210> SEQ ID NO 219
<211> LENGTH: 19
<212> TYPE: DNA
<213> ORGANISM: Artificial sequence
<220> FEATURE:
<223> OTHER INFORMATION: Probe

<400> SEQUENCE: 219
aggagaaggt ctgccgtta                                             19

<210> SEQ ID NO 220
<211> LENGTH: 21
<212> TYPE: DNA
<213> ORGANISM: Artificial sequence
<220> FEATURE:
<223> OTHER INFORMATION: Probe

<400> SEQUENCE: 220
gaggttcttt gagtcctttg g                                          21

<210> SEQ ID NO 221
<211> LENGTH: 19
<212> TYPE: DNA
<213> ORGANISM: Artificial sequence
<220> FEATURE:
<223> OTHER INFORMATION: Probe

<400> SEQUENCE: 221
caaaggactc aacctctgg                                             19

<210> SEQ ID NO 222
<211> LENGTH: 19
<212> TYPE: DNA
<213> ORGANISM: Artificial sequence
<220> FEATURE:
<223> OTHER INFORMATION: Probe

<400> SEQUENCE: 222
cccagaggtt cttttagtc                                             19

<210> SEQ ID NO 223
<211> LENGTH: 17
<212> TYPE: DNA
<213> ORGANISM: Artificial sequence
<220> FEATURE:
<223> OTHER INFORMATION: Probe

<400> SEQUENCE: 223
tgtggggcaa ggtgaac                                               17

<210> SEQ ID NO 224
<211> LENGTH: 18
<212> TYPE: DNA
<213> ORGANISM: Artificial sequence
<220> FEATURE:
<223> OTHER INFORMATION: Probe

<400> SEQUENCE: 224
ccgttactgc cctgtagg                                              18

<210> SEQ ID NO 225
<211> LENGTH: 17

```
<212> TYPE: DNA
<213> ORGANISM: Artificial sequence
<220> FEATURE:
<223> OTHER INFORMATION: Probe

<400> SEQUENCE: 225
ctgtggggaa ggtgaac                                                    17

<210> SEQ ID NO 226
<211> LENGTH: 18
<212> TYPE: DNA
<213> ORGANISM: Artificial sequence
<220> FEATURE:
<223> OTHER INFORMATION: Probe

<400> SEQUENCE: 226
tgtggggcta ggtgaacg                                                   18

<210> SEQ ID NO 227
<211> LENGTH: 18
<212> TYPE: DNA
<213> ORGANISM: Artificial sequence
<220> FEATURE:
<223> OTHER INFORMATION: Probe

<400> SEQUENCE: 227
cttcatccac gctcacct                                                   18

<210> SEQ ID NO 228
<211> LENGTH: 18
<212> TYPE: DNA
<213> ORGANISM: Artificial sequence
<220> FEATURE:
<223> OTHER INFORMATION: Probe

<400> SEQUENCE: 228
tgataccaac ctgcccag                                                   18

<210> SEQ ID NO 229
<211> LENGTH: 18
<212> TYPE: DNA
<213> ORGANISM: Artificial sequence
<220> FEATURE:
<223> OTHER INFORMATION: Probe

<400> SEQUENCE: 229
ctgggcagat tggtatca                                                   18

<210> SEQ ID NO 230
<211> LENGTH: 19
<212> TYPE: DNA
<213> ORGANISM: Artificial sequence
<220> FEATURE:
<223> OTHER INFORMATION: Probe

<400> SEQUENCE: 230
ccctgggcag tttggtatc                                                  19

<210> SEQ ID NO 231
<211> LENGTH: 21
<212> TYPE: DNA
<213> ORGANISM: Artificial sequence
<220> FEATURE:
<223> OTHER INFORMATION: Probe

<400> SEQUENCE: 231
```

```
gcaggttgct atcaaggtta c                                              21

<210> SEQ ID NO 232
<211> LENGTH: 17
<212> TYPE: DNA
<213> ORGANISM: Artificial sequence
<220> FEATURE:
<223> OTHER INFORMATION: Probe

<400> SEQUENCE: 232
ataccaacgt gcccagg                                                   17

<210> SEQ ID NO 233
<211> LENGTH: 18
<212> TYPE: DNA
<213> ORGANISM: Artificial sequence
<220> FEATURE:
<223> OTHER INFORMATION: Probe

<400> SEQUENCE: 233
ggtgccttta gtgatggc                                                  18

<210> SEQ ID NO 234
<211> LENGTH: 19
<212> TYPE: DNA
<213> ORGANISM: Artificial sequence
<220> FEATURE:
<223> OTHER INFORMATION: Probe

<400> SEQUENCE: 234
tcggtgcctt taagtgatg                                                 19

<210> SEQ ID NO 235
<211> LENGTH: 22
<212> TYPE: DNA
<213> ORGANISM: Artificial sequence
<220> FEATURE:
<223> OTHER INFORMATION: Probe

<400> SEQUENCE: 235
tgggttaagg caatagcaat at                                             22

<210> SEQ ID NO 236
<211> LENGTH: 21
<212> TYPE: DNA
<213> ORGANISM: Artificial sequence
<220> FEATURE:
<223> OTHER INFORMATION: Probe

<400> SEQUENCE: 236
atattgctat taccttaacc c                                              21

<210> SEQ ID NO 237
<211> LENGTH: 20
<212> TYPE: DNA
<213> ORGANISM: Artificial sequence
<220> FEATURE:
<223> OTHER INFORMATION: Probe

<400> SEQUENCE: 237
catacctctt atcttcctcc                                                20

<210> SEQ ID NO 238
<211> LENGTH: 23
<212> TYPE: DNA
<213> ORGANISM: Artificial sequence
```

```
<220> FEATURE:
<223> OTHER INFORMATION: Probe

<400> SEQUENCE: 238
tgtaacaagt agagattcaa gta                                              23

<210> SEQ ID NO 239
<211> LENGTH: 20
<212> TYPE: DNA
<213> ORGANISM: Artificial sequence
<220> FEATURE:
<223> OTHER INFORMATION: Probe

<400> SEQUENCE: 239
gaacttcagg gtgagtctat                                                  20

<210> SEQ ID NO 240
<211> LENGTH: 21
<212> TYPE: DNA
<213> ORGANISM: Artificial sequence
<220> FEATURE:
<223> OTHER INFORMATION: Probe

<400> SEQUENCE: 240
gaacttcagg atgagtctat g                                                21

<210> SEQ ID NO 241
<211> LENGTH: 20
<212> TYPE: DNA
<213> ORGANISM: Artificial sequence
<220> FEATURE:
<223> OTHER INFORMATION: Primer

<400> SEQUENCE: 241
acgyagcgcc tcattttgtg                                                  20

<210> SEQ ID NO 242
<211> LENGTH: 19
<212> TYPE: DNA
<213> ORGANISM: Artificial sequence
<220> FEATURE:
<223> OTHER INFORMATION: Primer

<400> SEQUENCE: 242
cactgcatgg cctgaggat                                                   19

<210> SEQ ID NO 243
<211> LENGTH: 19
<212> TYPE: DNA
<213> ORGANISM: Artificial sequence
<220> FEATURE:
<223> OTHER INFORMATION: Primer

<400> SEQUENCE: 243
cgagttcccg cccataacc                                                   19

<210> SEQ ID NO 244
<211> LENGTH: 19
<212> TYPE: DNA
<213> ORGANISM: Artificial sequence
<220> FEATURE:
<223> OTHER INFORMATION: Primer

<400> SEQUENCE: 244
ggaagttgca acgccgtcc                                                   19
```

<210> SEQ ID NO 245
<211> LENGTH: 14
<212> TYPE: DNA
<213> ORGANISM: Artificial sequence
<220> FEATURE:
<223> OTHER INFORMATION: Primer

<400> SEQUENCE: 245
ccacaagcca acca                                                      14

<210> SEQ ID NO 246
<211> LENGTH: 14
<212> TYPE: DNA
<213> ORGANISM: Artificial sequence
<220> FEATURE:
<223> OTHER INFORMATION: Primer

<400> SEQUENCE: 246
ccagcagcca acca                                                      14

<210> SEQ ID NO 247
<211> LENGTH: 16
<212> TYPE: DNA
<213> ORGANISM: Artificial sequence
<220> FEATURE:
<223> OTHER INFORMATION: Primer

<400> SEQUENCE: 247
gccaactcag aaaatc                                                    16

<210> SEQ ID NO 248
<211> LENGTH: 16
<212> TYPE: DNA
<213> ORGANISM: Artificial sequence
<220> FEATURE:
<223> OTHER INFORMATION: Primer

<400> SEQUENCE: 248
gccaactccg acaatc                                                    16

<210> SEQ ID NO 249
<211> LENGTH: 16
<212> TYPE: DNA
<213> ORGANISM: Artificial sequence
<220> FEATURE:
<223> OTHER INFORMATION: Primer

<400> SEQUENCE: 249
agaggcaaat caggta                                                    16

<210> SEQ ID NO 250
<211> LENGTH: 16
<212> TYPE: DNA
<213> ORGANISM: Artificial sequence
<220> FEATURE:
<223> OTHER INFORMATION: Primer

<400> SEQUENCE: 250
agcggcacac caggta                                                    16

<210> SEQ ID NO 251
<211> LENGTH: 16
<212> TYPE: DNA
<213> ORGANISM: Artificial sequence
<220> FEATURE:
<223> OTHER INFORMATION: Primer

<400> SEQUENCE: 251
ccaacaagga cacctg     16

<210> SEQ ID NO 252
<211> LENGTH: 16
<212> TYPE: DNA
<213> ORGANISM: Artificial sequence
<220> FEATURE:
<223> OTHER INFORMATION: Primer

<400> SEQUENCE: 252
ccaacaagga ccctg     16

<210> SEQ ID NO 253
<211> LENGTH: 14
<212> TYPE: DNA
<213> ORGANISM: Artificial sequence
<220> FEATURE:
<223> OTHER INFORMATION: Primer

<400> SEQUENCE: 253
ccactggaca gaag     14

<210> SEQ ID NO 254
<211> LENGTH: 15
<212> TYPE: DNA
<213> ORGANISM: Artificial sequence
<220> FEATURE:
<223> OTHER INFORMATION: Primer

<400> SEQUENCE: 254
cagaccatca gctgg     15

<210> SEQ ID NO 255
<211> LENGTH: 16
<212> TYPE: DNA
<213> ORGANISM: Artificial sequence
<220> FEATURE:
<223> OTHER INFORMATION: Primer

<400> SEQUENCE: 255
gcaaatacca acaatc     16

<210> SEQ ID NO 256
<211> LENGTH: 16
<212> TYPE: DNA
<213> ORGANISM: Artificial sequence
<220> FEATURE:
<223> OTHER INFORMATION: Primer

<400> SEQUENCE: 256
caacctcgcc accaga     16

<210> SEQ ID NO 257
<211> LENGTH: 16
<212> TYPE: DNA
<213> ORGANISM: Artificial sequence
<220> FEATURE:
<223> OTHER INFORMATION: Primer

<400> SEQUENCE: 257
gtcaccatat tcttgg     16

<210> SEQ ID NO 258

<211> LENGTH: 19
<212> TYPE: DNA
<213> ORGANISM: Artificial sequence
<220> FEATURE:
<223> OTHER INFORMATION: Primer

<400> SEQUENCE: 258
ctcgaatgcc tcgtatcat                                                                     19

<210> SEQ ID NO 259
<211> LENGTH: 19
<212> TYPE: DNA
<213> ORGANISM: Artificial sequence
<220> FEATURE:
<223> OTHER INFORMATION: Primer

<400> SEQUENCE: 259
gttccaacta ggaacatca                                                                     19

<210> SEQ ID NO 260
<211> LENGTH: 19
<212> TYPE: DNA
<213> ORGANISM: Artificial sequence
<220> FEATURE:
<223> OTHER INFORMATION: Primer

<400> SEQUENCE: 260
gttccaacta ggaacatca                                                                     19

<210> SEQ ID NO 261
<211> LENGTH: 560
<212> TYPE: DNA
<213> ORGANISM: Artificial sequence
<220> FEATURE:
<223> OTHER INFORMATION: HBV positive control sequence

<400> SEQUENCE: 261
tgggattcta tataagaggg aaactacacg tagcgcctca ttttgcgggt caccatattc        60
ttgggaacaa gagctacatc atgggaggtt ggtcatcaaa acctcgcaaa ggcatgggga       120 cgaaccttc tgttcccaac cctctgggat tctttcccga tcatcagttg gaccctgcat        180
tcggagccaa ttcaaacaat ccagattggg acttcaaccc catcaaggac cactggccac      240
aagccaacca gtaggagtg ggagcattcg ggccagggtt cactccccca cacggaggtg       300
ttttggggtg gagccctcag gctcagggca tattggccac agtgccagca gtgcctcctc     360
ctgcctccac caatcggcag tcaggaaggc agcctactcc catctctcca cctctaagag     420
acagtcatcc tcaggccatg cagtggaatt ccacagcttt ccaccaagct ctgcaagatc     480
ccagagtcag gggcctgtat tttcctgctg gtggctccag ttcaggaaca ctcaaccctg     540
ttccaactat tgcctctcac                                                 560

<210> SEQ ID NO 262
<211> LENGTH: 500
<212> TYPE: DNA
<213> ORGANISM: Artificial sequence
<220> FEATURE:
<223> OTHER INFORMATION: Internal amplification control sequence

<400> SEQUENCE: 262
gagacaggtt cgtccaatcc cgtgccgcgg ccttggcagg gggttcgcag gccccacccg        60
aagcgttgct gaaggctcag gcctctgagc gacaaaagct ttaaacgcga gttcccgccc      120
ataacctgga ccgaatgcgg gaccatgcat cgttccactg tgtttgtccc atgtaggacg      180

```
ggcgcaaggc gtgcttagct cagcctcgaa tgcctcgtat cattgtgcac ccgccggtca    240
ccagccaacg atgtgcggac ggcgttgcaa cttccggggc ccaacctgac cgtcctgggt    300
accgcactct gggcagtgcg aggtaatgcc agtcgcccag tgccgaacaa cacctgacct    360
aacggtaaga ggctcacata atggctccgc cggcgcgccc agggtacatt aggtcagcat    420
cggatggact gacatgaacc ttcacaccga agcggaaacg ggtgcgtgga ccagcgagga    480
gcaaacgaaa attcctggcc                                                500
```

<210> SEQ ID NO 263
<211> LENGTH: 40
<212> TYPE: DNA
<213> ORGANISM: Artificial sequence
<220> FEATURE:
<223> OTHER INFORMATION: Primer

<400> SEQUENCE: 263

```
gaccacaacg ctacgacgct aatcaatgcc cgggattggt                           40
```

<210> SEQ ID NO 264
<211> LENGTH: 40
<212> TYPE: DNA
<213> ORGANISM: Artificial sequence
<220> FEATURE:
<223> OTHER INFORMATION: Primer

<400> SEQUENCE: 264

```
ttctgcttgt ccggctacga tccggagcga gttacgaaga                           40
```

<210> SEQ ID NO 265
<211> LENGTH: 40
<212> TYPE: DNA
<213> ORGANISM: Artificial sequence
<220> FEATURE:
<223> OTHER INFORMATION: Primer

<400> SEQUENCE: 265

```
gaccacaacg ctacgacgct aacgaggcat tgaagcaaag                           40
```

<210> SEQ ID NO 266
<211> LENGTH: 40
<212> TYPE: DNA
<213> ORGANISM: Artificial sequence
<220> FEATURE:
<223> OTHER INFORMATION: Primer

<400> SEQUENCE: 266

```
ttctgcttgt ccggctacga ctgctgtttc aagtcgtcca                           40
```

<210> SEQ ID NO 267
<211> LENGTH: 41
<212> TYPE: DNA
<213> ORGANISM: Artificial sequence
<220> FEATURE:
<223> OTHER INFORMATION: Primer

<400> SEQUENCE: 267

```
gaccacaacg ctacgacgct actgtggtag ataccacacg c                         41
```

<210> SEQ ID NO 268
<211> LENGTH: 41
<212> TYPE: DNA
<213> ORGANISM: Artificial sequence
<220> FEATURE:

<223> OTHER INFORMATION: Primer

<400> SEQUENCE: 268
ttctgcttgt ccggctacga acaggtaatg gcctgtgact g         41

<210> SEQ ID NO 269
<211> LENGTH: 43
<212> TYPE: DNA
<213> ORGANISM: Artificial sequence
<220> FEATURE:
<223> OTHER INFORMATION: Primer

<400> SEQUENCE: 269
gaccacaacg ctacgacgct gttgatgaaa ccttaacccc ttg       43

<210> SEQ ID NO 270
<211> LENGTH: 43
<212> TYPE: DNA
<213> ORGANISM: Artificial sequence
<220> FEATURE:
<223> OTHER INFORMATION: Primer

<400> SEQUENCE: 270
ttctgcttgt ccggctacga gttgaggggt tttccatttt tgc       43

<210> SEQ ID NO 271
<211> LENGTH: 44
<212> TYPE: DNA
<213> ORGANISM: Artificial sequence
<220> FEATURE:
<223> OTHER INFORMATION: Primer

<400> SEQUENCE: 271
gaccacaacg ctacgacgct gtcaggatca tcaaatcaat tcac      44

<210> SEQ ID NO 272
<211> LENGTH: 40
<212> TYPE: DNA
<213> ORGANISM: Artificial sequence
<220> FEATURE:
<223> OTHER INFORMATION: Primer

<400> SEQUENCE: 272
ttctgcttgt ccggctacga caacttggat aggacggtca           40

<210> SEQ ID NO 273
<211> LENGTH: 41
<212> TYPE: DNA
<213> ORGANISM: Artificial sequence
<220> FEATURE:
<223> OTHER INFORMATION: Primer

<400> SEQUENCE: 273
gaccacaacg ctacgacgct cagagccatc agccctttc a          41

<210> SEQ ID NO 274
<211> LENGTH: 42
<212> TYPE: DNA
<213> ORGANISM: Artificial sequence
<220> FEATURE:
<223> OTHER INFORMATION: Primer

<400> SEQUENCE: 274
ttctgcttgt ccggctacga gaagtttgtc ccagttgcgg tt        42

```
<210> SEQ ID NO 275
<211> LENGTH: 40
<212> TYPE: DNA
<213> ORGANISM: Artificial sequence
<220> FEATURE:
<223> OTHER INFORMATION: Primer

<400> SEQUENCE: 275
gaccacaacg ctacgacgct actccatgaa gtcggaatcg                           40

<210> SEQ ID NO 276
<211> LENGTH: 40
<212> TYPE: DNA
<213> ORGANISM: Artificial sequence
<220> FEATURE:
<223> OTHER INFORMATION: Primer

<400> SEQUENCE: 276
ttctgcttgt ccggctacga cccacgttct cgtagggata                           40

<210> SEQ ID NO 277
<211> LENGTH: 41
<212> TYPE: DNA
<213> ORGANISM: Artificial sequence
<220> FEATURE:
<223> OTHER INFORMATION: Primer

<400> SEQUENCE: 277
gaccacaacg ctacgacgct gttggagctg gaatagttgc t                         41

<210> SEQ ID NO 278
<211> LENGTH: 41
<212> TYPE: DNA
<213> ORGANISM: Artificial sequence
<220> FEATURE:
<223> OTHER INFORMATION: Primer

<400> SEQUENCE: 278
ttctgcttgt ccggctacga cagctgatgt aagtgcagca t                         41

<210> SEQ ID NO 279
<211> LENGTH: 41
<212> TYPE: DNA
<213> ORGANISM: Artificial sequence
<220> FEATURE:
<223> OTHER INFORMATION: Primer

<400> SEQUENCE: 279
gaccacaacg ctacgacgct ccaccatgta ctacaaagac g                         41

<210> SEQ ID NO 280
<211> LENGTH: 38
<212> TYPE: DNA
<213> ORGANISM: Artificial sequence
<220> FEATURE:
<223> OTHER INFORMATION: Primer

<400> SEQUENCE: 280
ttctgcttgt ccggctacga tggtcgtccc ggtgaaac                             38

<210> SEQ ID NO 281
<211> LENGTH: 42
<212> TYPE: DNA
<213> ORGANISM: Artificial sequence
<220> FEATURE:
<223> OTHER INFORMATION: Primer
```

```
<400> SEQUENCE: 281
gaccacaacg ctacgacgct gtcgaacatt ggtcttaccc tc                    42

<210> SEQ ID NO 282
<211> LENGTH: 40
<212> TYPE: DNA
<213> ORGANISM: Artificial sequence
<220> FEATURE:
<223> OTHER INFORMATION: Primer

<400> SEQUENCE: 282
ttctgcttgt ccggctacga tgtgccgtct tcaagtatgc                       40

<210> SEQ ID NO 283
<211> LENGTH: 40
<212> TYPE: DNA
<213> ORGANISM: Artificial sequence
<220> FEATURE:
<223> OTHER INFORMATION: Primer

<400> SEQUENCE: 283
gaccacaacg ctacgacgct gaagagccaa ggacaggtac                       40

<210> SEQ ID NO 284
<211> LENGTH: 41
<212> TYPE: DNA
<213> ORGANISM: Artificial sequence
<220> FEATURE:
<223> OTHER INFORMATION: Primer

<400> SEQUENCE: 284
ttctgcttgt ccggctacga ccttgatacc aacctgccca g                     41

<210> SEQ ID NO 285
<211> LENGTH: 20
<212> TYPE: DNA
<213> ORGANISM: Artificial sequence
<220> FEATURE:
<223> OTHER INFORMATION: Primer

<400> SEQUENCE: 285
gaccacaacg ctacgacgct                                             20

<210> SEQ ID NO 286
<211> LENGTH: 20
<212> TYPE: DNA
<213> ORGANISM: Artificial sequence
<220> FEATURE:
<223> OTHER INFORMATION: Primer

<400> SEQUENCE: 286
ttctgcttgt ccggctacga                                             20

<210> SEQ ID NO 287
<211> LENGTH: 19
<212> TYPE: DNA
<213> ORGANISM: Artificial sequence
<220> FEATURE:
<223> OTHER INFORMATION: Probe

<400> SEQUENCE: 287
agtgcataaa cttctgagg                                              19

<210> SEQ ID NO 288
<211> LENGTH: 20
```

```
<212> TYPE: DNA
<213> ORGANISM: Artificial sequence
<220> FEATURE:
<223> OTHER INFORMATION: Probe

<400> SEQUENCE: 288
tataaacgcc cggcagttac                                          20

<210> SEQ ID NO 289
<211> LENGTH: 20
<212> TYPE: DNA
<213> ORGANISM: Artificial sequence
<220> FEATURE:
<223> OTHER INFORMATION: Probe

<400> SEQUENCE: 289
aaagattact ggagagaacc                                          20

<210> SEQ ID NO 290
<211> LENGTH: 20
<212> TYPE: DNA
<213> ORGANISM: Artificial sequence
<220> FEATURE:
<223> OTHER INFORMATION: Probe

<400> SEQUENCE: 290
tgaacgaagg tagagaagca                                          20

<210> SEQ ID NO 291
<211> LENGTH: 20
<212> TYPE: DNA
<213> ORGANISM: Artificial sequence
<220> FEATURE:
<223> OTHER INFORMATION: Probe

<400> SEQUENCE: 291
tgcggtttac gaaattgaaa                                          20

<210> SEQ ID NO 292
<211> LENGTH: 20
<212> TYPE: DNA
<213> ORGANISM: Artificial sequence
<220> FEATURE:
<223> OTHER INFORMATION: Probe

<400> SEQUENCE: 292
actcatgacg aacgaagaag                                          20

<210> SEQ ID NO 293
<211> LENGTH: 19
<212> TYPE: DNA
<213> ORGANISM: Artificial sequence
<220> FEATURE:
<223> OTHER INFORMATION: Probe

<400> SEQUENCE: 293
gcagaaaaac tatcctcag                                           19

<210> SEQ ID NO 294
<211> LENGTH: 20
<212> TYPE: DNA
<213> ORGANISM: Artificial sequence
<220> FEATURE:
<223> OTHER INFORMATION: Probe

<400> SEQUENCE: 294
```
cagctatgct gcggtgaata    20

<210> SEQ ID NO 295
<211> LENGTH: 19
<212> TYPE: DNA
<213> ORGANISM: Artificial sequence
<220> FEATURE:
<223> OTHER INFORMATION: Probe

<400> SEQUENCE: 295
cttgtcgatc acctcctcg    19

<210> SEQ ID NO 296
<211> LENGTH: 19
<212> TYPE: DNA
<213> ORGANISM: Artificial sequence
<220> FEATURE:
<223> OTHER INFORMATION: Probe

<400> SEQUENCE: 296
ttatgtgcat ccgtaacta    19

<210> SEQ ID NO 297
<211> LENGTH: 22
<212> TYPE: DNA
<213> ORGANISM: Artificial sequence
<220> FEATURE:
<223> OTHER INFORMATION: Probe

<400> SEQUENCE: 297
gtagcagatt tagacacaga tg    22

<210> SEQ ID NO 298
<211> LENGTH: 26
<212> TYPE: DNA
<213> ORGANISM: Artificial sequence
<220> FEATURE:
<223> OTHER INFORMATION: Probe

<400> SEQUENCE: 298
aaggtgaacg tggatgaagt tggtgg    26

<210> SEQ ID NO 299
<211> LENGTH: 20
<212> TYPE: DNA
<213> ORGANISM: Artificial sequence
<220> FEATURE:
<223> OTHER INFORMATION: Probe

<400> SEQUENCE: 299
gaaaatgatg cccagtgctt    20

<210> SEQ ID NO 300
<211> LENGTH: 20
<212> TYPE: DNA
<213> ORGANISM: Artificial sequence
<220> FEATURE:
<223> OTHER INFORMATION: Probe

<400> SEQUENCE: 300
ttgaaggaaa tgccccatta    20

<210> SEQ ID NO 301
<211> LENGTH: 20
<212> TYPE: DNA
<213> ORGANISM: Artificial sequence -continued

```
<220> FEATURE:
<223> OTHER INFORMATION: Probe

<400> SEQUENCE: 301
gaaccaatcc cgtgaaagaa                                               20

<210> SEQ ID NO 302
<211> LENGTH: 20
<212> TYPE: DNA
<213> ORGANISM: Artificial sequence
<220> FEATURE:
<223> OTHER INFORMATION: Probe

<400> SEQUENCE: 302
agctgcccat gaatagcact                                               20

<210> SEQ ID NO 303
<211> LENGTH: 19
<212> TYPE: DNA
<213> ORGANISM: Artificial sequence
<220> FEATURE:
<223> OTHER INFORMATION: Probe

<400> SEQUENCE: 303
ggttacccca aaggccacc                                                19

<210> SEQ ID NO 304
<211> LENGTH: 20
<212> TYPE: DNA
<213> ORGANISM: Artificial sequence
<220> FEATURE:
<223> OTHER INFORMATION: Probe

<400> SEQUENCE: 304
aagcggaaga atgtgtcagc                                               20

<210> SEQ ID NO 305
<211> LENGTH: 20
<212> TYPE: DNA
<213> ORGANISM: Artificial sequence
<220> FEATURE:
<223> OTHER INFORMATION: Probe

<400> SEQUENCE: 305
tttggggagc tgaaggacta                                               20

<210> SEQ ID NO 306
<211> LENGTH: 20
<212> TYPE: DNA
<213> ORGANISM: Artificial sequence
<220> FEATURE:
<223> OTHER INFORMATION: Probe

<400> SEQUENCE: 306
ctttgtgacc attccggttt                                               20

<210> SEQ ID NO 307
<211> LENGTH: 15
<212> TYPE: DNA
<213> ORGANISM: Artificial sequence
<220> FEATURE:
<223> OTHER INFORMATION: Probe

<400> SEQUENCE: 307
ggacaggcga ggaat                                                    15
```

```
<210> SEQ ID NO 308
<211> LENGTH: 16
<212> TYPE: DNA
<213> ORGANISM: Artificial sequence
<220> FEATURE:
<223> OTHER INFORMATION: Probe

<400> SEQUENCE: 308
tggacaggca aggaat                                              16

<210> SEQ ID NO 309
<211> LENGTH: 14
<212> TYPE: DNA
<213> ORGANISM: Artificial sequence
<220> FEATURE:
<223> OTHER INFORMATION: Probe

<400> SEQUENCE: 309
tctcagcgag cctc                                                14

<210> SEQ ID NO 310
<211> LENGTH: 14
<212> TYPE: DNA
<213> ORGANISM: Artificial sequence
<220> FEATURE:
<223> OTHER INFORMATION: Probe

<400> SEQUENCE: 310
actctcagca agcc                                                14

<210> SEQ ID NO 311
<211> LENGTH: 15
<212> TYPE: DNA
<213> ORGANISM: Artificial sequence
<220> FEATURE:
<223> OTHER INFORMATION: Probe

<400> SEQUENCE: 311
cgggagccga tttca                                               15

<210> SEQ ID NO 312
<211> LENGTH: 17
<212> TYPE: DNA
<213> ORGANISM: Artificial sequence
<220> FEATURE:
<223> OTHER INFORMATION: Probe

<400> SEQUENCE: 312
atgatgaaat cgactcc                                             17

<210> SEQ ID NO 313
<211> LENGTH: 17
<212> TYPE: DNA
<213> ORGANISM: Artificial sequence
<220> FEATURE:
<223> OTHER INFORMATION: Probe

<400> SEQUENCE: 313
cagtgaagaa agtgtct                                             17

<210> SEQ ID NO 314
<211> LENGTH: 17
<212> TYPE: DNA
<213> ORGANISM: Artificial sequence
<220> FEATURE:
<223> OTHER INFORMATION: Probe
```

-continued

<400> SEQUENCE: 314

```
gaccagtgaa gcaagtg                                                     17
```

RAPID GENOTYPING ANALYSIS AND DEVICES THEREOF

CROSS-REFERENCE TO RELATED APPLICATIONS

This is a continuation-in-part application of U.S. Ser. No. 12/770,034, filed Apr. 29, 2010. The content of the preceding application is hereby incorporated in its entirety by reference into this application.

FIELD OF INVENTION

The present invention is related to the field of identification of various genotypes associated with human diseases.

BACKGROUND OF THE INVENTION

Identification of Human Leukocytic Antigens (HLA)

Accurate HLA typing is essential for matching donor and recipient in organ or marrow transplantation (4) to prevent the development of acute graft-versus-host disease (GVHD). This is generally accomplished by standard serological typing (2). Recent studies have demonstrated that DNA genotyping can provide more accurate and definitive result (7, 9, 8). Results of HLA-DQ, DR and DP genotyping provided data for accurate matching which is necessary in selecting potential organ donors (3). HLA genotyping using sequence-specific primers polymerase chain reaction (SSP-PCR) amplifications has been previously reported. However, due to highly polymorphic nature of HLA-DQ, DR and DP loci, the number of SSP required will be in the hundreds, and, therefore, exceed the limit of multiplex-PCR for efficient PCR amplification. To ensure the results of HLA genotyping have practical clinical application, multiple of 50 to 100 of separate PCR reactions have to be setup. A kit that is available on the market today includes an amplification process of carrying out a 96 PCR separate reactions, then followed by analysis on gel electrophoresis size separation. This is not only time consuming and costly but prone to error due to the complexity of the reaction setup and sizing uncertainty of the gel electrophoresis. Thus, DNA sequencing is still considered the method of choice for accurate genotyping of the HLA cluster. Unfortunately, because of the existence of highly homologous sequence of pseudogene(s) that may be co-amplified during the polymerase chain reaction (PCR) amplification process, accurate genotyping by DNA sequencing alone may prove more difficult and costly. U.S. Pat. Nos. 5,471,547 and 6,020,187, issued to J. W. O. Tam, disclose a fast annealing process that uses a very inexpensive device for accurate mutation detection, genotyping and fingerprinting analysis. The present invention discloses a method of rapidly analyzing HLA loci of DP, DR and DQ beta sequences by ASO oligoprobes using an improved flow-through format.

DNA Fingerprinting for Rapid Identification of Human Beings and Organisms

DNA fingerprinting by restriction fragment length polymorphism (RFLP) was first introduced in 1985 (12) for human identification, and was subsequently applied to identification of other organisms. In practical applications, DNA fingerprinting has been widely accepted as the best forensic tool for identification of suspects in criminal cases, for paternity disputes and for establishing or verifying the identity of a person. The time consuming RFLP method has been gradually replaced by high throughput automated processes. Using PCR amplification for analyzing the number of short tandem repeat (STR), first discovered in 1991 (11), from 10, 16, 18 or more loci in the human genome, single cell identification is now possible. However, both STR and/or variable number of tandem repeats (VNTR) are relatively expensive because these methods require the use of sophisticated equipment, and labor intensive and time consuming process like the Southern blotting hybridization. Sporadic mutations (10) may reduce the accuracy and the power for definitive identification. Furthermore, STR data suggested that the frequency of mutation, particularly in cancer patients, is not uncommon. Hence, new alternative method is needed. Single nucleotide polymorphism (SNP) genotyping provides greater discriminating power by selecting an appropriate number of SNPs at unlink loci, and the mutation frequency in each locus (site) is lower than VNTR or STR systems for forensic or individual personal identification. This invention presents a method of making rapid, definitive biometric identification of an individual, such as a human being, animal, plant or any organism, using SNP genotyping.

HPV Genotyping

Human papillomaviruses (HPV) attack mucosal cells and is very heterogeneous; about 200 different genotypes have been reported in world-wide population with different prevalence among the species. According to their disease causing severity HPV strains are categorized into high risk (HR) and low risk (LR) strains. HR types are more frequently found in premalignant or malignant cervical lesions, while LR types in benign cases (4). There are about half million new cases of cervical cancer and estimated deaths of over 250,000 annually. Thus, HPV infection and cervical cancer remain one of the major female cancers worldwide (5). For this reason, HPV screening for the cervical cancer prevention is recommended since it is more sensitive than cytology (6,7).

Clinical studies revealed that 99.7% of cervical carcinoma was found to be associated with HR-HPV infections. Although HPV may be cleared for most infections, persistence of HR-HPV infection would lead to the development of high grade cervical intraepithelial neoplasia (i.e. CIN I; CIN II or CIN III) and the progression to cervical cancer (7, 8). Hence assays targeting to HPV viral DNA are developed and commercially available. The U.S. FDA has approved Hybrid Capture 2 (HC2) system (Digene Corporation, Gaithersburg, Md., USA), and the AMPLICOR HPV Test (Roche Molecular Diagnostics, Branchburg, N.J., USA). These screening tests identify the presence of either HR or LR of the most prevalent types of HPV in groups without differentiating genotypes. Although these tests provide good assays for HPV screening, the inability of genotyping HPV limits their use for clinical diagnostic and prognostic applications because the disease causing severity is very different, among them type 16 is most serve followed by 18, 33, 45 and 59 and so on (8). Furthermore persistent infection with the same HPV genotype will further increase the risk for cervical cancer (9). Hence effective and affordable genotyping assays are most needed.

The LINEAR ARRAY HPV Genotyping Test (covering 37 types by Roche Molecular Diagnostics, Branchburg, N.J., USA), and the INNO-LiPA HPV Genotyping covering 28 types (Innogenetics, Belgium), could complement either HC2 or the AMPLICOR HPV Test assay in distinguishing specific genotypes, and identify infections involving multiple genotypes. Given the facts that 1) oncogenic potential varies among HR-HPVs; 2) risk is elevated with persistent infection of the same genotypes; and 3) HPV vaccines available could not prevent all types of HPV infections, HPV genotyping is needed in addition to just generic screening for the presence or absence of HPV viruses. However, the above assays are expensive and still use conventional hybridization processes that require high running cost and hands on time. Most importantly, these genotyping kits lack the ability to detect HPV viruses outside their predetermined genotyping panel and therefore results in higher false negative rate in HPV screening. Hence, there is a need for HPV genotyping assays that are faster, cheaper, cover more genotypes and therefore more effective as an affordable alternative for HPV detection.

Tubuculosis Detection

Tuberculosis (TB) is caused by *Mycobacterium tuberculosis* (MTB). The emergence of anti-tuberculosis drug resistance is a serious problem for TB control programs in industrialized and developing countries alike. In addition to its clinical and epidemiological importance, multidrug-resistant tuberculosis (DR-MTB) has important economic impact because the cost of treatment is higher than that of normal MTB. DR-MTB is defined as resistance to at least two of the most effective first-line drugs, rifampin (RIF) and isoniazid (INH). These cases are on the rise globally, resulting in significant morbidity and mortality. Resistance to first-line anti-tuberculosis drugs has been linked to mutations in several genes in the MTB genome: rpoB for RIF resistance; katG and inhA for INH resistance.

Several technologies exist for DR-MTB detection. Conventional phenotypic Drug susceptibility testing (DST) remains the gold standard for MTB drug resistance testing but can take up to eight weeks to complete. Treatment would often begin before the results are confirmed. Conventional DNA sequencing for detection of MTB drug resistance mutations is not routinely available in the commercial setting because of the expense, necessary expertise and time-consuming nature. Alternatively, by utilizing polymerase chain reaction (PCR) and "Flow-through" hybridization technology, the present invention provides GenoFlow™ DR-MTB Array Test that can detect MTB drug resistance (from DNA extraction to analysis) within 4 hours with highly specific and sensitive result.

Beta Thalassemia Detection

Beta Thalassemia is a common hemoglobinopathy that is caused by autosomal mutations, which can be sub-divided into categories depending on the extent to which beta-globin production is affected. Some mutations result in mild reductions in the production of beta-globin (denoted as $\beta^+$), whereas some cause absolute silencing of the beta-globin gene, or the production of non-functional beta-globin (denoted as $\beta^0$). It is estimated that around 1.5% of the world's population are beta-thalassemia heterozygotes, or carriers, and the coupling of two carriers may produce offsprings that are homozygous for the disease. Disease severity manifests in three different degrees: from mild (thalassemia minor, $\beta^+/\beta$ or $\beta^0/\beta$) to intermediary (thalassemia intermedia, $\beta^+/\beta$ or $\beta^0/\beta$ to severe (thalassemia major, $\beta^+/\beta^+$, $\beta^0/\beta^+$ or $\beta^0/\beta^0$). Individuals that inherit the thalassemia major trait develop hypochromic anemia, and may require life-long blood transfusion. The best method of beta-thalassemia control is prevention of birth of thalassemic children, by genetic counseling of prospective parents and prenatal diagnosis, which have proven to be the most effective management for the disease.

Beta-thalassemia is endemic in temperate regions such as Mediterranean countries, Middle East and Southeast Asia. The molecular bases for beta-thalassemia has been extensively studied and micro-mapped to point mutations along the beta-globin gene. Different geographic regions have different mutation spectra, and the frequency of mutations is not homogeneous in each region.

Current detection technologies include microarray, AS-PCR and direct sequencing. Alternatively, DNA testing using PCR with reverse dot blot hybridization has offered a highly sensitive and specific method for beta-globin mutant detection and has further permitted for the genotyping which assist the diagnosis of beta-thalassemia.

Hepatitis B Virus Detection

HBV is the smallest DNA virus comprising 3000 nucleotides surrounded by a protein capsid. It can be transmitted through contact with blood or body fluids of an infected individual. Approximately 2 billion people are infected with HBV; in which over 350 million become HBV carriers. About one-fifth would develop HBV-related cirrhosis or eventually liver cancer. Detection of HBV can be diagnosed by surface antigen using simple blood tests and HBV DNA measurement using polymerase chain reaction (PCR).

In addition, analysis of the divergence of HBV genome sequences has led to the identification of 10 HBV genotypes (A to J) and several subtypes. HBV genotypes and subtypes show a distinct geographical distribution. It has been discovered that pathogenic and therapeutic differences exist among various HBV genotypes. The determination of HBV genotypes can provide information for the management of chronic HBV infection and pre-treatment evaluation. DNA sequencing has been considered as the gold standard method for the detection of HBV genotypes. However, it is less efficient in detecting mixed genotypes. Alternatively, using molecular DNA techniques has offered a highly sensitive and specific method for HBV genotype detection.

Detection of Sexually Transmitted Disease

Sexually transmitted diseases (STDs) are common worldwide. According to 2005 WHO estimates, 448 million new cases of curable STDs (syphilis, gonorrhoea, chlamydia and trichomoniasis) occur annually throughout the world in adults aged 15-49 years. In Hong Kong, around 1 in 550 was diagnosed with Sexually Transmitted diseases (not including HIV) in 2010. For pregnant woman, STDs can infect her baby before, during, or after the baby's birth. Untreated gonorrhea and chlamydia may result in infertility. Therefore, pre-married couples and pre-pregnancy women are also potential users of STDs detection. In addition, China is also a potential market of STDs diagnosis, as the number of STDs patient increase dramatically in past 20 years. The fast, low-price and accurate STDs diagnostic kit is necessary for controlling STDs in China.

Thrombophilia Identification

Thrombophilia is an abnormality of blood coagulation that increases the risk of thrombosis. Studies report that about 40% of thrombophilia cases presenting with thrombosis are inherited and has been shown to be a risk factor for cardiovascular disease including venous thrombosis as well as reproductive disorders including recurrent miscarriage. There is a growing view that inherited thrombophilia would predispose women towards adverse pregnancy outcomes including recurrent pregnancy losses, intrauterine fetal death, intrauterine growth retardation, preeclampsia and placental abruption.

Over the past two decades, several gene variants have been identified for inherited thrombophilia. The top 4 mutations are located at Factor V Leiden (FVL) [1691G>A], Factor II (Prothrombin) [20210G>A], Methylenetetrahydrofolate Reductase (MTHFR) [677C>T] and Methylenetetrahydrofolate Reductase (MTHFR) [1298A>C].

Testing for these genetic variations can greatly contribute to identification of high risk population of venous thrombosis and recurrent miscarriage, so as to help lowering the individual's risk and preventing the diseases and also providing prophylactic treatment guidance.

SUMMARY OF THE PRESENT INVENTION

HLA Genotyping

Preliminary results suggested that the Allelic-Specific-Oligonucleotide Reversed-Dot-Blotting (ASO-RDB) direct flow-through hybridization is a better alternative for the detection of specific target HLA DNA sequences. The data obtained refer to the specific segments of HLA loci of DP, DR and DQ beta that are able to provide accurate determination of the genotypes. Using one pair of PCR primer and 35 ASO oligo-probes, 83 $DPB_1$ alleles identified by the World Health Organization (WHO) can be effectively classified. Similarly, using one common PCR primer pair and 18 ASO oligo-probes, this simple hybridization protocol can identify the first 2 digit codes of the specific genotypes of the DR and DQ beta loci, enough to distinguish between these major classes of HLA. ASO data are validated by direct PCR sequencing. However, when the same PCR primer pairs are used to perform direct sequencing on the DR and DQ loci, un-interpretable sequencing data occurred frequently. This is because the same pair of primers can also co-amplify highly homologous endogenous pseudogene fragment within the HLA cluster. For this reason DNA sequencing (considered by many as the gold standard) may not be able to guarantee the results for HLA classification. In these cases, to confirm the ASO data, many sets of PCR primers corresponding to each specific HLA types in question were created, and used to perform PCR amplification in separate reactions to create amplicons for sequencing. The positive amplicon(s) were then sequenced. This is the primary reason that direct sequencing may prove to be costly and time consuming. In contrast, the present invention provides a cost effective procedure for HLA identification by using common primer pairs to perform a simple multiplex PCR followed by hybridization with the required numbers of ASO-probes in a Low-Density Array format. The amplified HLA fragments (including the pseudogenes) can be analyzed in a single membrane embedded with the ASO-probes for definitive HLA classification. Hence, this is a far superior method than other DNA or serological methods currently available. Although further detailed classification of the DR, DQ subtypes requires additional oligo-probes when using the direct flow-through method, the number of such oligo-probes is well within the capability of the present format. This invention provides a HLA typing technique which is faster and simpler, does not require expensive equipment, and is therefore less costly to manufacture and operate than direct DNA sequencing and multiplex PCR gel electrophoresis procedures.

The primers and oligo-probes disclosed herein for HLA genotyping have been tested and confirmed to be useful for the classification of HLA genotypes corresponding to the DR, DB and DP genes reported above. Following the scheme presented in FIG. 1 or FIG. 1A, additional primers and/or oligo-probes can be obtained, tested and validated for a more comprehensive genotyping. Although, in the data validating examples, PCR was used for amplification, any method that can produce specific target sequence(s) in sufficient quantity for the ASO-RDB flow-through hybridization analysis may be used. Other appropriate amplification methods or technique is readily apparent to one of ordinary skill in the art reading the teaching herein Amplification may not be necessary if sufficient quantity of the target sequence(s) can be obtained for the ASO-RDB flow-through hybridization analysis. Detection can be accomplished by labeling of the target DNA or conjugates.

Although HLA genotyping is exemplified in this application, the SNP-based genotyping technique can be applied to other genetic materials and/or sequences obtained from any organism following the teaching of this application, such as the procedures shown in FIG. 1 or FIG. 1A. A flow-through device similar to those described in the U.S. Pat. No. 5,741, 547 or 6,020,187, or any new embodiments capable of carrying out flow-through hybridization process can be used.

SNP Genotyping

The human genome and the genome of many other organisms have been sequenced and mapped. Within any species, the general DNA sequence information is very similar. However, each species has its own distinct set of genetic information. Hence, many scientists have attempted to characterize disease-related variation among populations. For example, anthropologists use genetic variation to reconstruct human species' history, and to understand the role of culture and geography in the global distribution of human variation. Single nucleotide polymorphism (SNP) data can serve these purposes (12). Brightwell et al. reported the application of SNP genotyping using a simple and rapid single-tube modification of ARMS illustrated by analysis of 6 SNPs in a population of males with FRAXA repeat expansions (15).

The present invention describes the use of allele specific oligonucleotide (ASO) arrays. The number of SNP needed to provide adequate discriminating power is easily attainable by one of ordinary skill in the art following the teaching of this application. The membrane-based micro-array ASO-RDB flow-through hybridization format (e.g., see U.S. Pat. No. 5,741,647) may be used to facilitate SNP genotyping. Micro-array hybridization format of the present invention produces visible dots which can be analyzed by visual inspection and/or by using a less costly image analyzer. In contrast, commercially available hybridization format requires high resolution image analyzer for analysis. In principle, SNP of sufficient number may be used anywhere in the genome for discriminating purposes. However, this may compromise the accuracy of paternity and kinship analyses because of the variability of mutation rate in different parts of the genome. Hence, highly polymorphic sites or points in the genome where the mutation rate is relatively low including, but is not limited to, the coding region or any regions that satisfy the conditions of relatively low mutation rate may be selected to ensure the inherence nature for kinship identification. Preliminary data obtained using SNPs from 9 highly polymorphic chromosome loci shows that these SNPs were sufficient for SNP genotyping. The number of loci required will depend on the discriminating power required, which is readily apparent to a person of ordinary skill in the art reading the teaching herein. In constructing a polymorphic frequency database for each site, the sequenced DNA samples from 50-150 unrelated individuals is obtained. The kinship analyses of 20 families were performed in parallel with STR Profiler Plus human identity kit, and the results were 100% in agreement. SNP-based flow-through format has proven to be a better alternative for human identification. In addition to data already accumulated and analyzed, expansion of the polymorphic frequency database can be easily accomplished by one of ordinary skill in the art following the teaching of the present application.

SNP Genotyping as a Diagnostic Tool

Other than for DNA fingerprinting, SNP genotyping can be utilized for identification of gene fragments, or polymorphism of genes that have altered or attenuated the function of the gene in question. For this reason, the present invention can be used for rapid, definitive identification of infectious agents, inherited disease caused by the specific DNA sequences, or the presence or absence of such infectious agents or DNA sequences that cause inherited diseases.

HPV Genotyping

The present invention provides a HPV genotyping method comprising a PCR-based assay that includes co-amplification of a human gene as an internal control to measure the integrity of the sample together with the HPV target through the membrane-based flow-through hybridization technology (U.S. Pat. No. 5,741,647). This method identifies 33 high risk (HR) and low risk (LR) HPV viral genotypes (6, 11, 16, 18, 26, 31, 33, 35, 39, 40, 42, 43, 44, 45, 51, 52, 53, 54, 55, 56, 57, 58, 59, 61, 66, 68, 70, 71, 72, 73, 81, 82, 84). In addition, novel universal probe(s) were also designed to capture HPV genotypes that have the HPV consensus generic sequences. Thus, in addition to the 33 genotypes included in the test panel, it has been showed that the universal probe(s) also captured at least 5 other HPV viral subtypes during clinical screening with satisfactory sensitivity and specificity and considerable reduction in the cost (10), thereby providing a better alternative assay for HPV genotyping.

Multidrug-Resistance Tuberculosis Detection

This invention provides a method to detect rifampicin (RIF) and isoniazid (INH) resistant strains of *Mycobacterium Tuberculosis* (MTB) using Polymerase Chain Reaction (PCR) and "Flow-through" hybridization technology. Ten mutation probes are included for detection of drug resistant mutations in rpoB (D516V, D516G, H526D, H526Y, H526L1, S531L and S531W), katG (S315T1 and S315T2), and inhA (−15TC/T) while 5 wild-type probes are present for detection of its wild-type variant. MTB control probes are also present to ensure successful PCR reaction and amplification of rpoB, katG and inhA genes.

Beta Thalassemia Detection

This invention provides a system for the detection of beta-globin mutations including TATA-28 (A>G), TATA-29 (A>G), Initiation Codon (G>A), Codon 5 (−CT), Codons 8/9 (+G), Codon 15 (G>A), Codon 16 (−C), Codon 17 (A>T), Codon 19 (A>G), Codon 26 (G>A) (Hb E), Codons 27/28 (+C), Codon 30 G>C, IVS1.1 (G>T), IVS1.1 (G>A), IVS1.5 (G>C), Codons 41/42 (−TCTT), Codon 43 (G>T), Codons 71/72 (+A), IVS2.1 (G>A), IVS2.654 (C>T), and 619 bp deletion.

Hepatitis B Virus Detection

This invention provides method to detect the presence of 8 HBV genotypes (HBV Genotypes A, B, C, D, E, F, G and H) in human serum samples.

Detection of Sexually Transmitted Disease

This invention provides method to detect the presence of 1 protozoan, 7 bacteria and 4 viruses in urine, urogential swab (urethral, vaginal, cervical and lesion) and Liquid-based cytology specimens (PreservCyt™ and SurePath™). Amplification Control (AC) is included for detection of human DNA materials. DNA hybridization and PCR technologies enable a faster detection of STDs in urine, urogential swab (urethral, vaginal, cervical and lesion) and Liquid-based cytology specimens (PreservCyt™ and SurePath™). The array can detect the presence of 12 common pathogens; 1 protozoan (*Trichomonas vaginalis*), 7 bacteria (*Chlamydia trachomatis, Neisseria gonorrhoeae, Mycoplasma genitalium, Mycoplasma hominis, Ureaplasma urealyticum, Ureaplasma parvum, Treponema pallidum*) and 4 viruses (Herpes simplex virus 1 & 2, Human papillomavirus type 6 &11). These pathogens were selected as they are related to cervicitis, urethritis, trichomoniasis and pelvic inflammatory disease. Universal primer is introduced in the primer system for simpler primer labeling and balanced amplification among different targets. Amplification control is included to check for the presence of sufficient cellular content and validity of the results.

Thrombophilia Identification

This invention provides method for the identification of gene variants related to inherited thrombophilia, including Factor V Leiden (FVL) [1691G>A], Factor II (Prothrombin) [20210G>A], Methylenetetrahydrofolate Reductase (MTHFR) [677C>T] and Methylenetetrahydrofolate Reductase (MTHFR) [1298A>C].

Although PCR was used for amplification in the data validating examples, any method that can produce specific target sequence(s) in sufficient quantity for the ASO-RDB flow-through hybridization analysis may be used. Other appropriate amplification methods or technique is readily apparent to one of ordinary skill in the art reading the teaching herein. Amplification may not be necessary if sufficient quantity of the target sequence(s) can be obtained for the ASO-RDB flow-through hybridization analysis. Detection can be accomplished by labeling of the target DNA or conjugates.

A flow-through device similar to those described in the U.S. Pat. No. 5,741,547 or 6,020,187, or any new embodiments capable of carrying out flow-through hybridization process can be used.

DETAILED DESCRIPTION OF THE DRAWINGS

FIG. 4 shows a sample data for HLA-DRB and DQB genotyping identification.

FIG. 6 shows a membrane of the present invention designed for high throughput analyses.

FIG. 7 shows an exploded view of a hybridization device of the present invention, and arrangements of multiple lateral flow-through detection devices connected to a central control unit. In an embodiment, the hybridization device comprises a central controlling unit connected to one or more lateral flow device. The central controlling unit provides power to and controls the lateral flow device where the hybridization process and developing procedures are carried out. Several reactions (or several samples and/or analytes) can be tested simultaneously in a single lateral flow device or in several devices (controlled individually at different conditions) at the same time. The lateral flow device can be in a format of n×m dot matrix (array) or in the form of linear arrays (as shown). Since, during the reaction process, the test solution flows from one end of the array to the other end of the array (i.e., in an east to west, or in a north to south direction), the sensitivity of the detection is increased substantially. The extent of increase in sensitivity depends on the ratio of the total area of the membrane to the area of the dot or line containing the capturing probes. For example, assuming the total area of membrane is 100 mm square, and the dot size is 1 mm square. In a direct flow-through process (i.e., the solution flows from top surface through the membrane down to the other side of the membrane as in a conventional flow-through process), only 1/100 of the total test solution used will flow through the dot, the location where the target molecule will bind to the probe(s) immobilized on the membrane. However, if a lateral flow-through process is used, the sensitivity is only dependent on the ratio of the width of the dot to the width of the membrane (i.e., the cross section of the membrane). For instance, in a lateral flow-through process, the total amount of solution that will pass through a 1 mm dot provided on a 10 mm×10 mm membrane will be about 1/10, which represents a 10-fold increase in sensitivity using the same amount of target analyte (test solution containing the target molecules). When a line array format is used in the lateral flow-through process, the sensitivity will be further increased since all the target molecules will pass through the line extending across the strip (or membrane). The lateral flow-through process allows quantitative measurements to be taken during the hybridization process because the flow of the analyst is more uniform.

Figure 8:
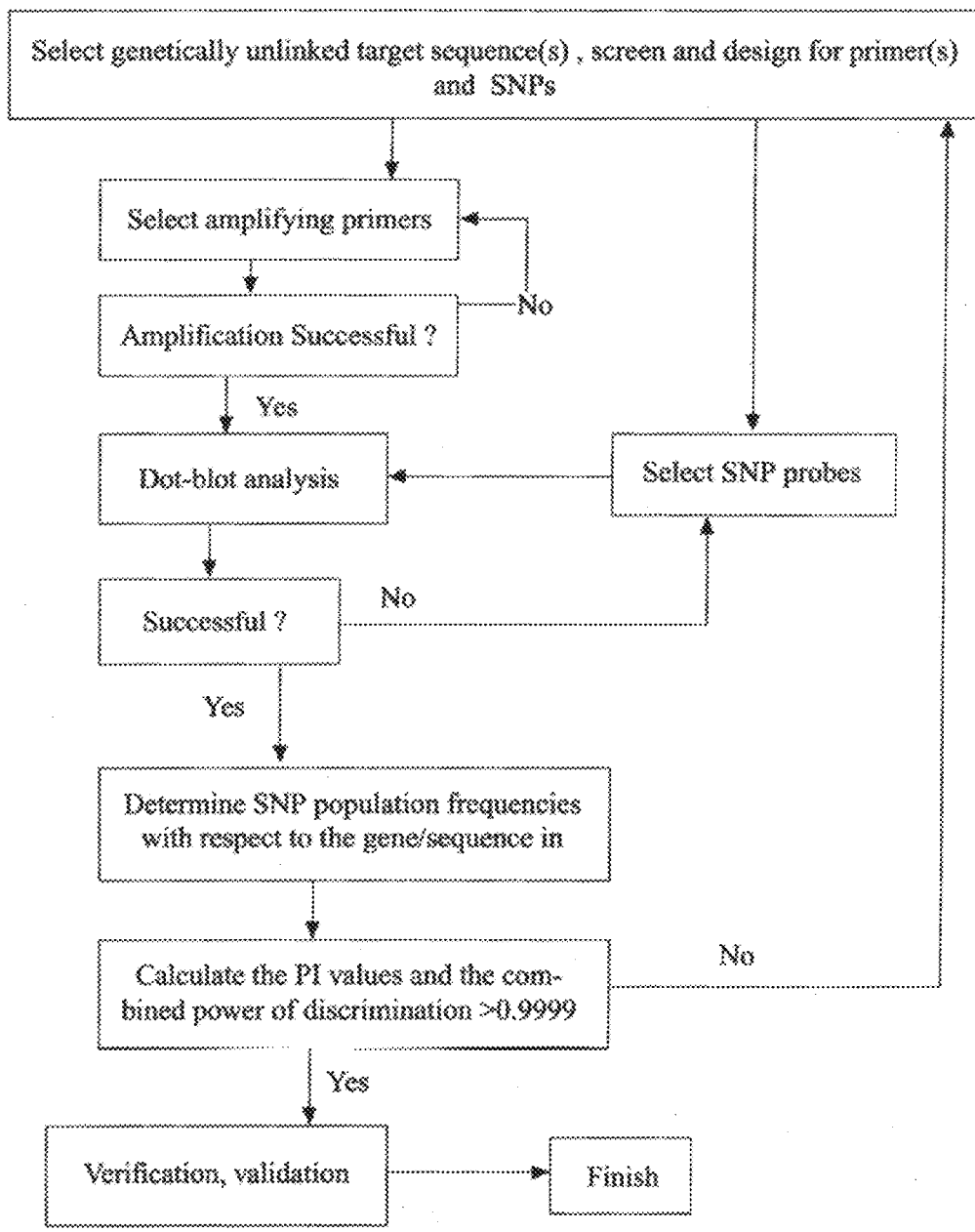

FIG. 8 shows a method of the present invention for constructing a SNP database.

Figures 9, 10:
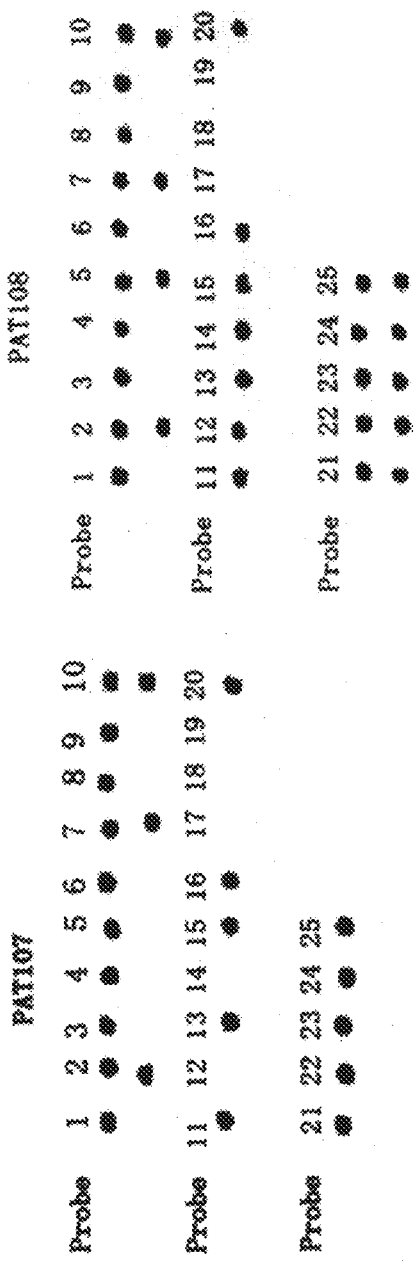

FIG. 9 shows a sample data for identification of a human being or an organism using SNP genotyping.

FIG. 10 shows the loci used for the method in the FIG. 8.

FIG. 11 shows a HLA-DPB1 genotyping results based on samples obtained from a Chinese population (Table 1).

FIG. 12 shows HLA-DPB1 allele and genotype frequencies for a Chinese population (Table 2).

FIG. 13 shows the ASO Oligonucleotide probe sequences identifying the respective HLA genotypes, and the PCR primer sequence pairs for amplify the corresponding fragments for analysis.

FIG. 14 shows the Oligonucleotide probe sequences identifying the respective HPV genotypes, and the PCR primer sequence pairs for amplify the corresponding L1 fragments for analysis. "+A" represents Locked Nucleic Acid-modified adenine, "+T" represents Locked Nucleic Acid-modified thymine.

Figure 15:
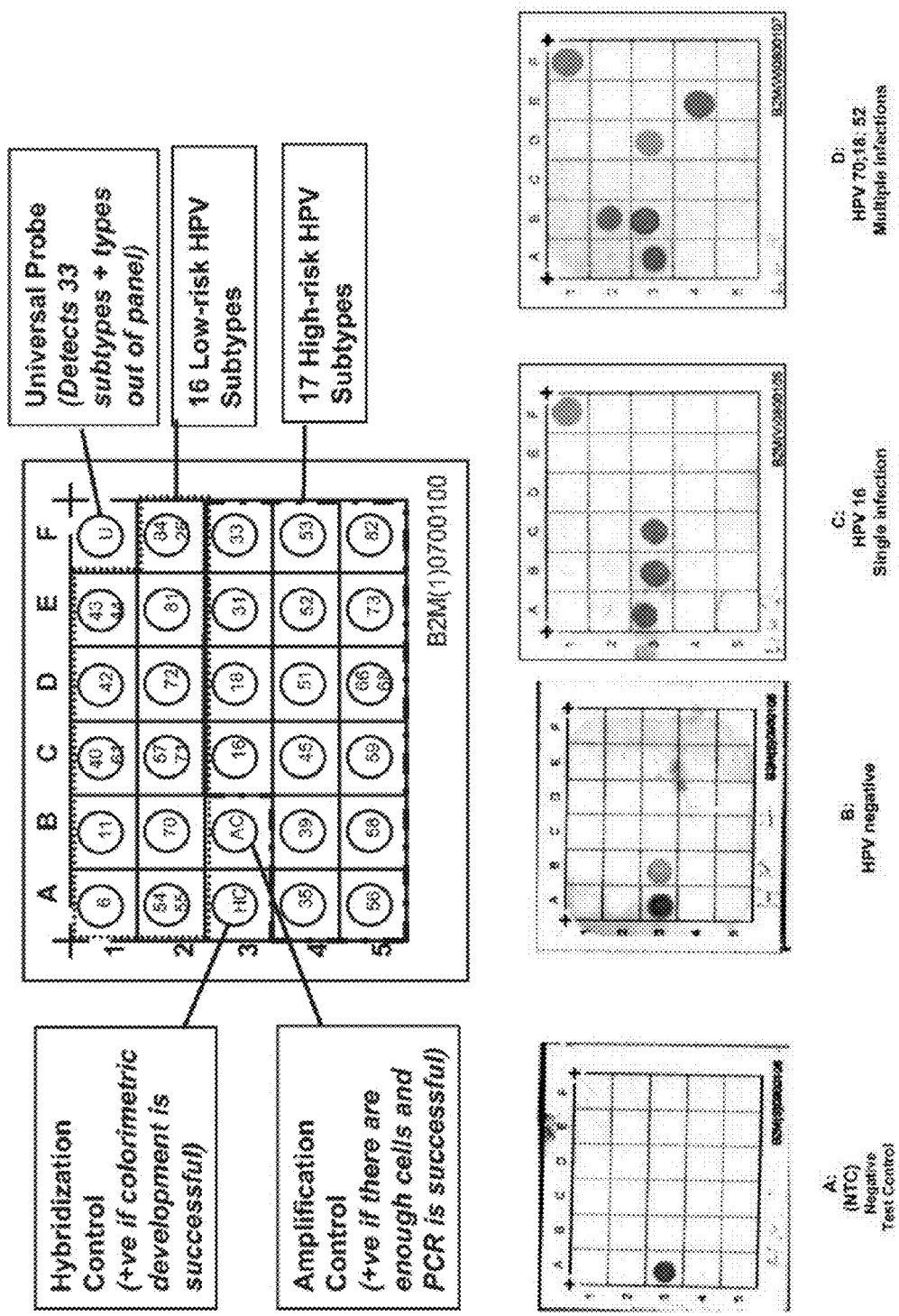

FIG. 15 shows typical images of the HPV-33 genotyping detection array profile for HPV infection.

FIG. 16 shows a typical image of the HR-HPV-14 genotyping detection array profile for HPV infections.

Figure 17:
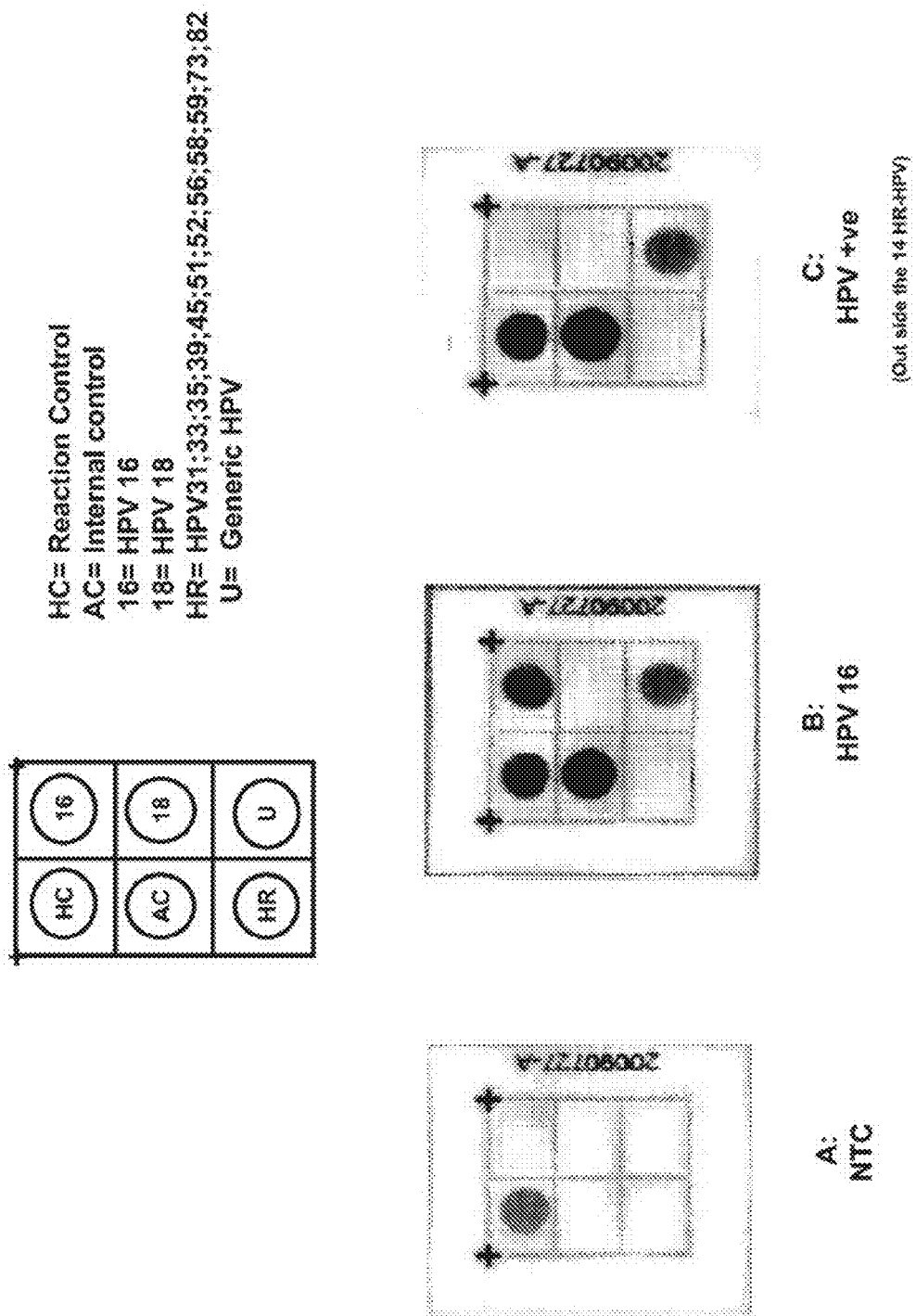

FIG. 17 shows the simplified screening HPV format for inexpensive and higher throughput improvements for HPV detection kit.

FIG. 18 shows the other simplified screening HPV formats for inexpensive and higher throughput improvements for HPV detection kit.

Figure 19:
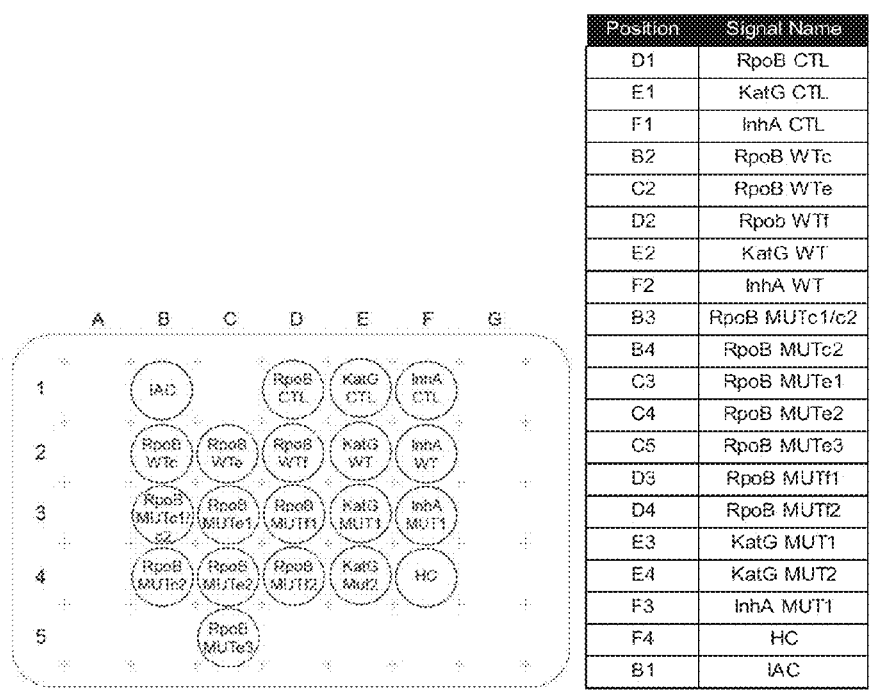

FIG. 19 shows one embodiment of DR-MTB cassette and signal position (grids shown for illustration purpose only).

Figure 20:
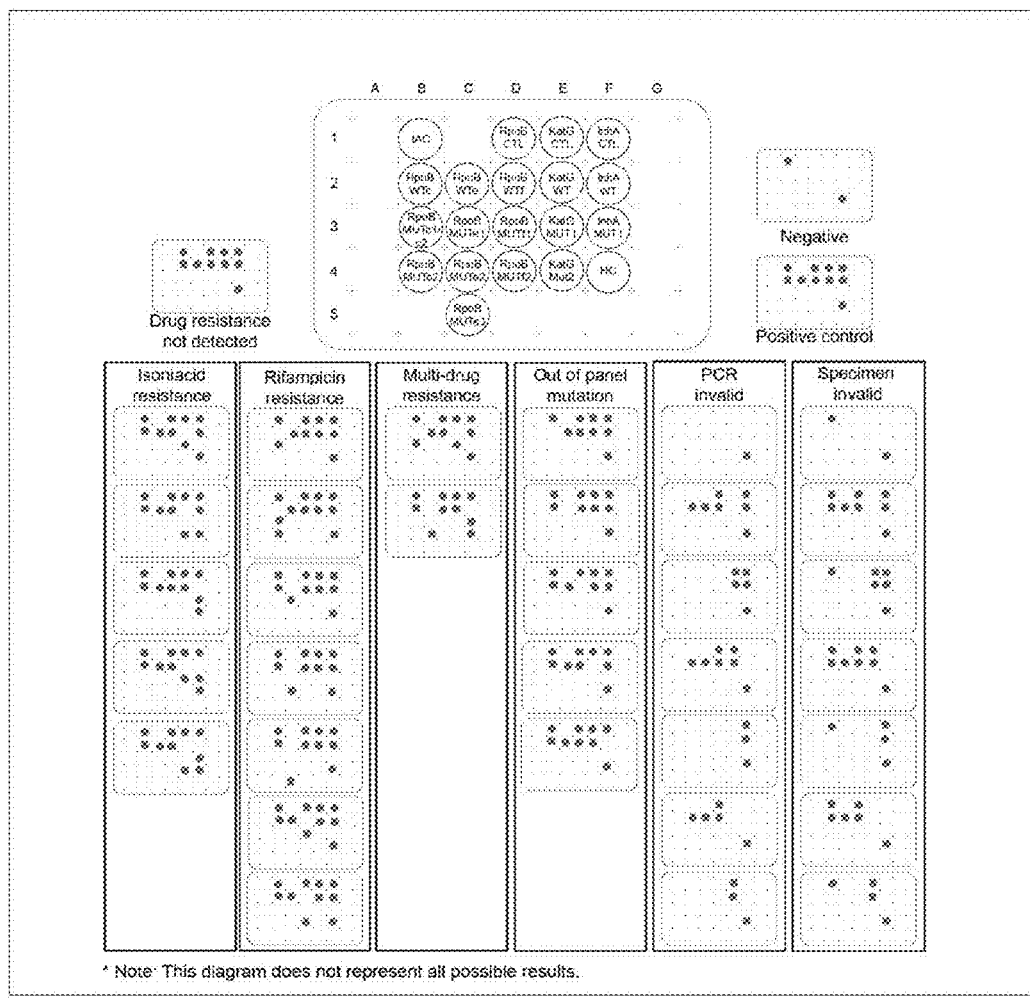

FIG. 20 shows one example of visual interpretation of different MTB mutants.

Figure 21:
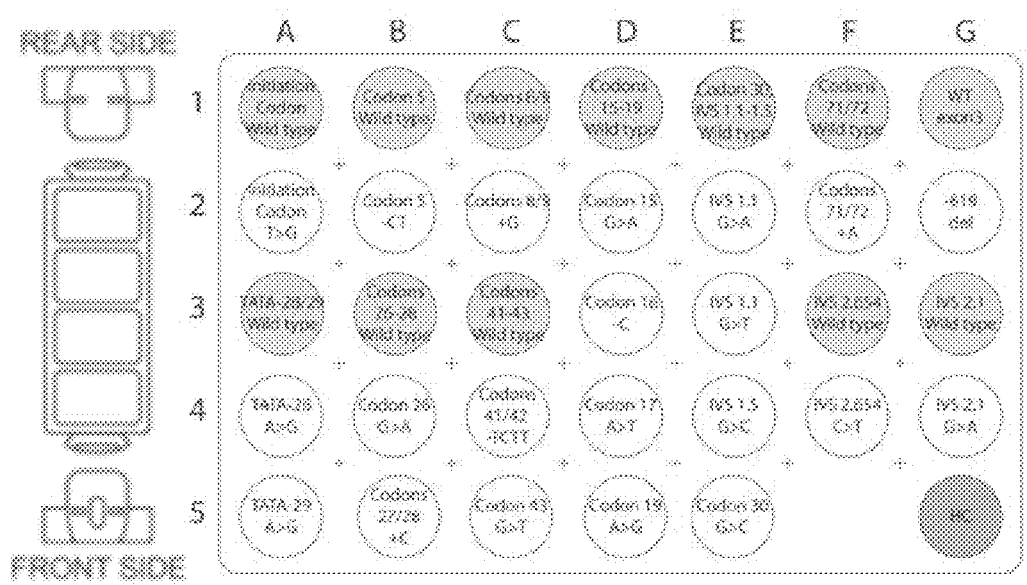

FIG. 21 shows one embodiment of beta-thalassemia cassette and signal position (grids shown for illustration purpose only).

Figure 22:
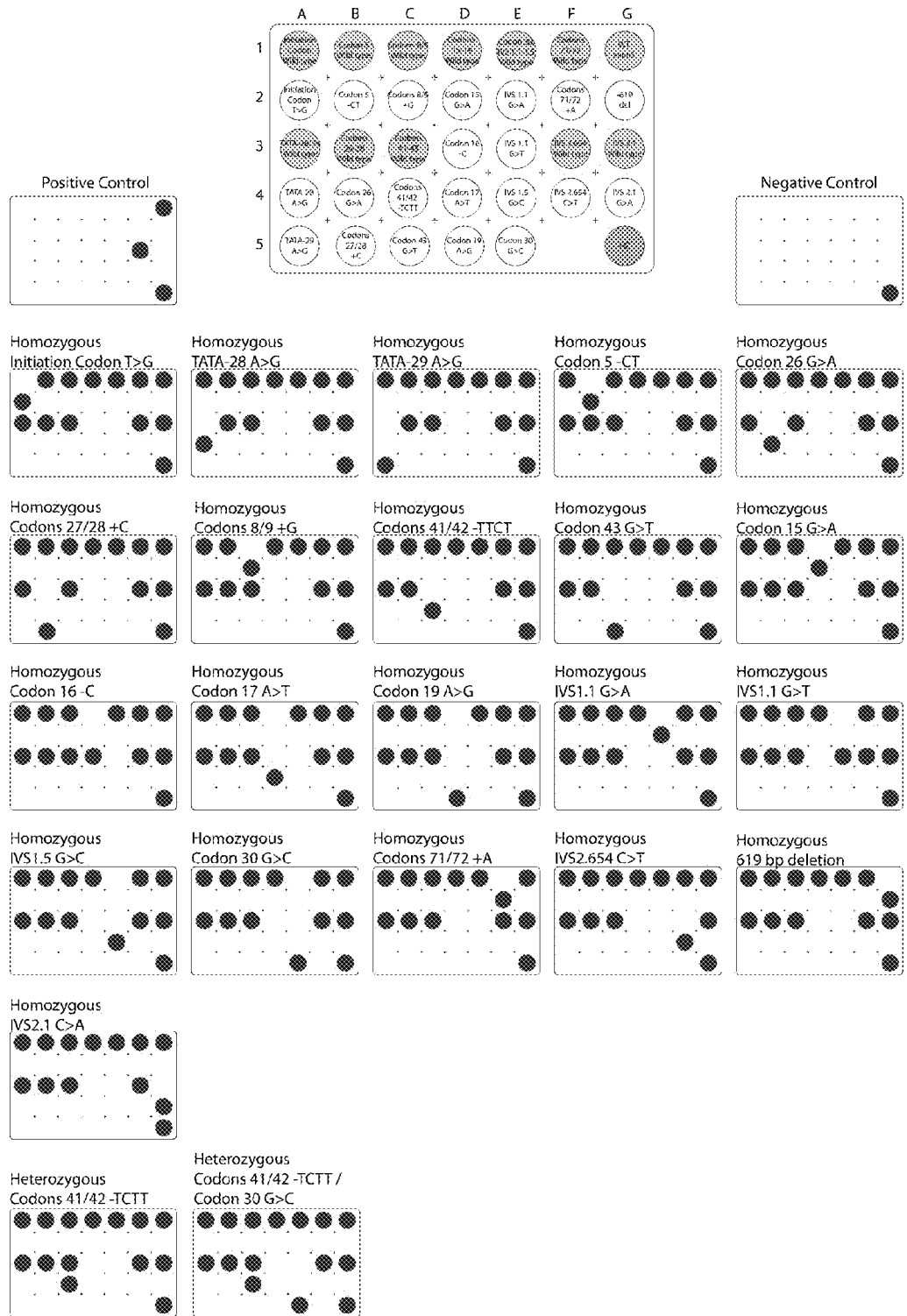

FIG. 22 shows one example of visual interpretation of different beta-thalassemia genotypes.

Figure 23:
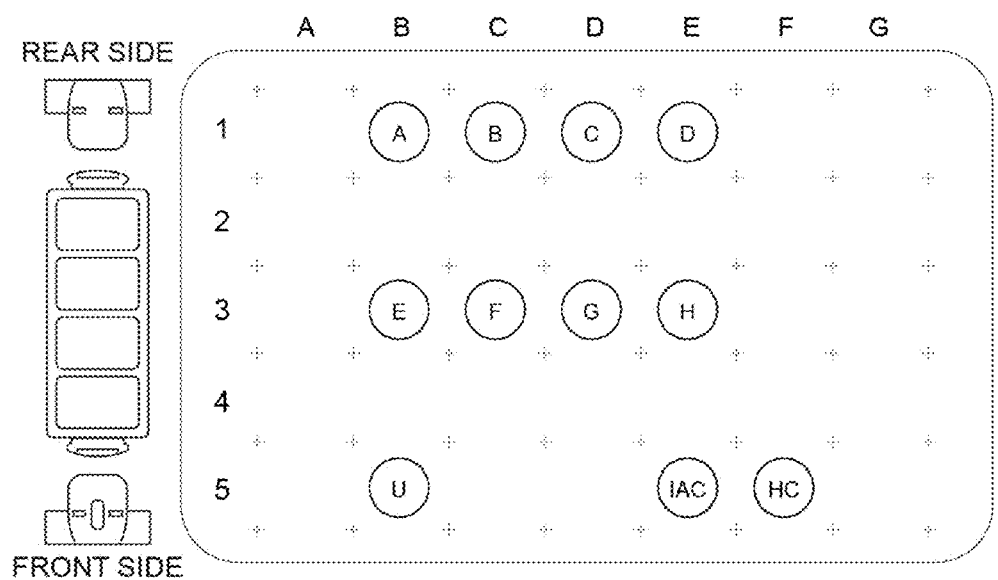

FIG. 23 shows one embodiment of a HBV test kit detecting the presence of 8 HBV genotypes (HBV A, B, C, D, E, F, G and H).

Figure 24:
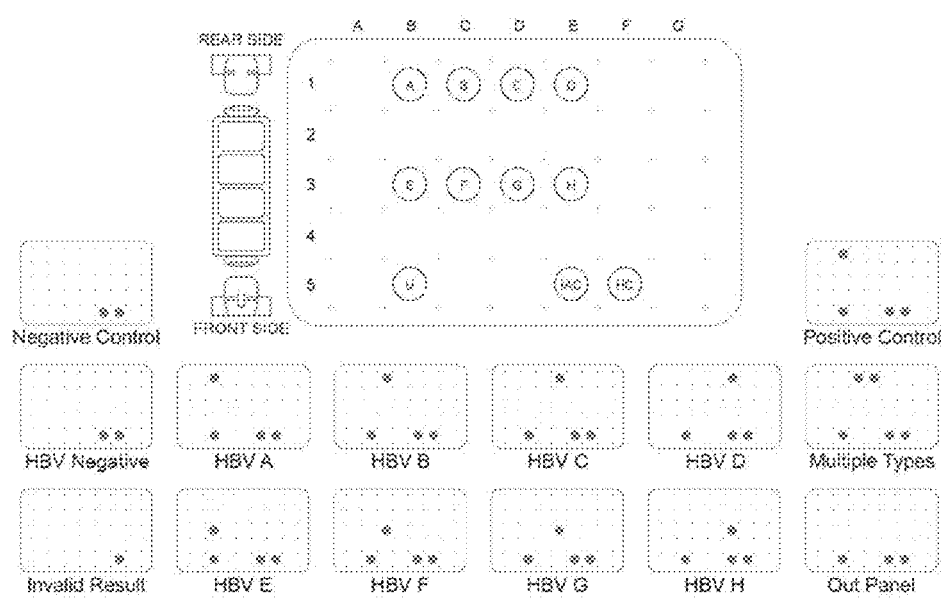

FIG. 24 shows one example of visual interpretation of different HBV genotypes.

Figure 25:
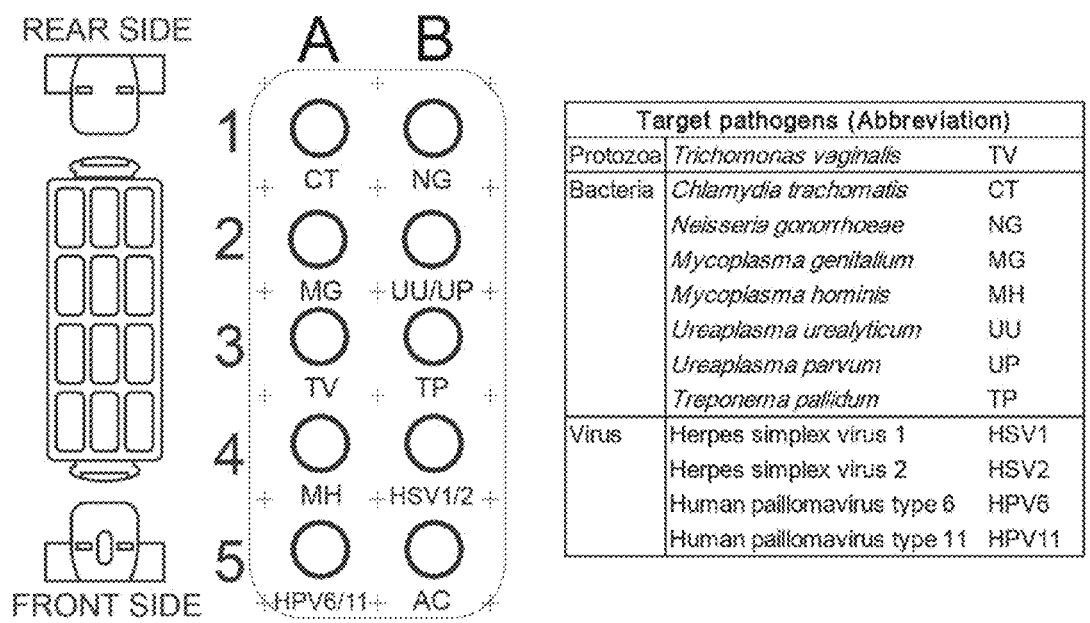

FIG. 25 shows one embodiment of a STD array that can detect the presence of 12 common pathogens; 1 protozoan (*Trichomonas vaginalis*), 7 bacteria (*Chlamydia trachomatis, Neisseria gonorrhoeae, Mycoplasma genitalium, Mycoplasma hominis, Ureaplasma urealyticum, Ureaplasma parvum, Treponema pallidum*) and 4 viruses (Herpes simplex virus 1 & 2, Human papillomavirus type 6 &11). Universal primer is introduced in the primer system for simpler primer labeling and balanced amplification among different targets. Amplification control is included to check for the presence of sufficient cellular content and validity of the results.

Figure 26:
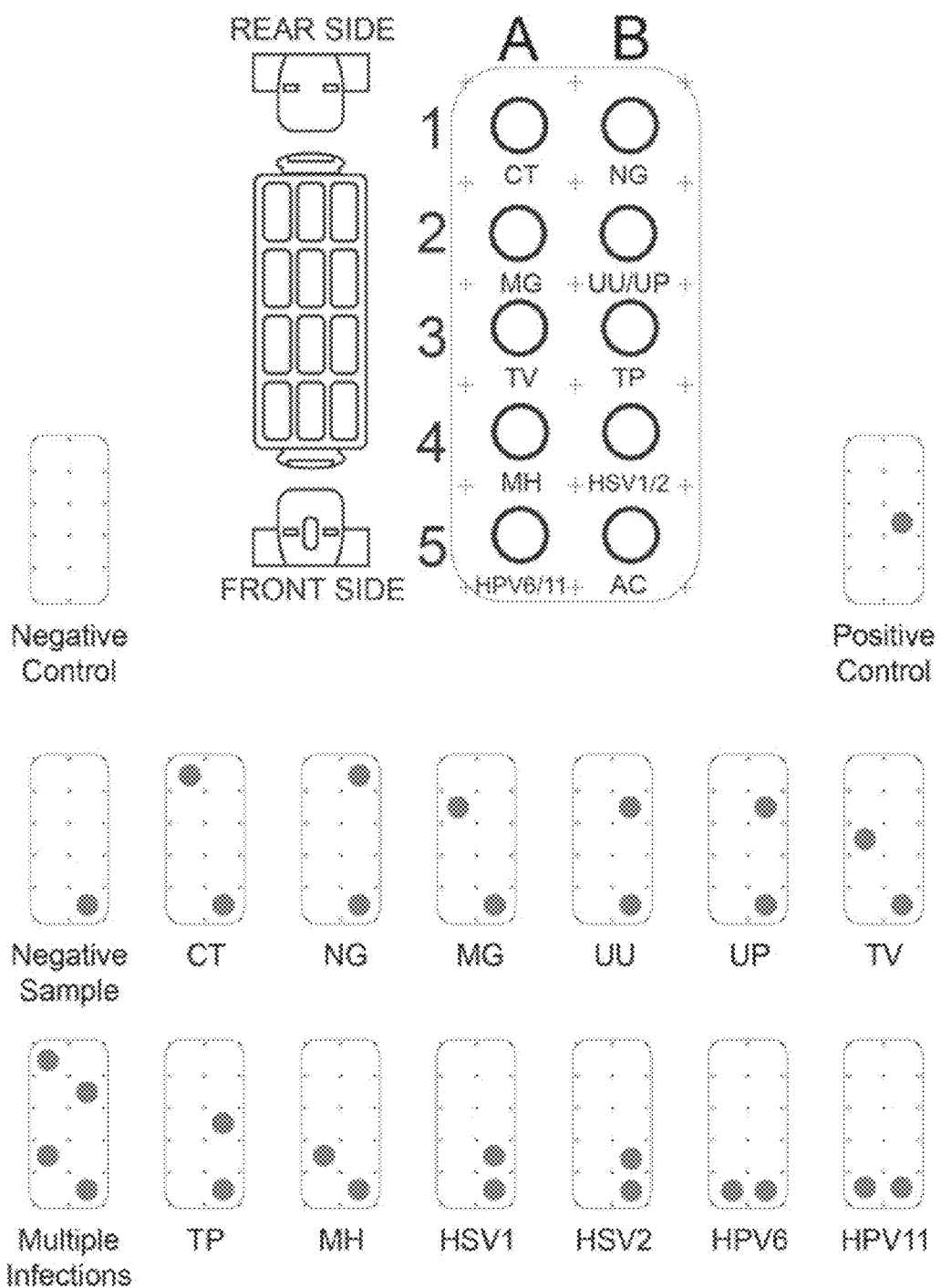

FIG. 26 shows one example of visual interpretation of the STD array.

Figure 27:
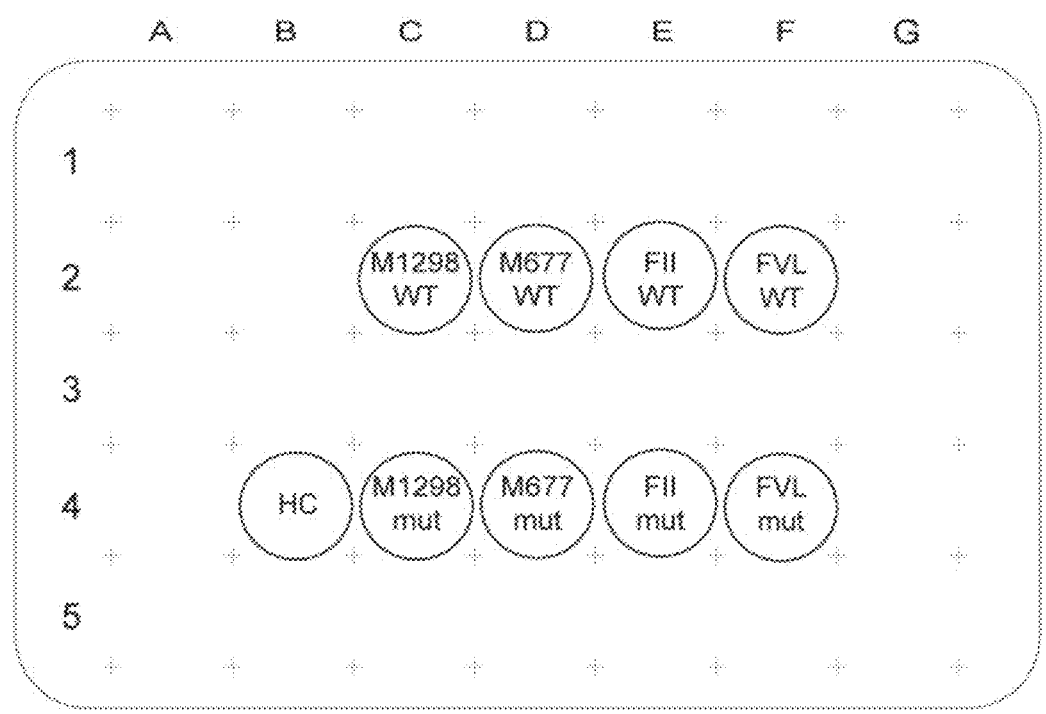

FIG. 27 shows one embodiment of a Thrombophilia array.

Figure 28:
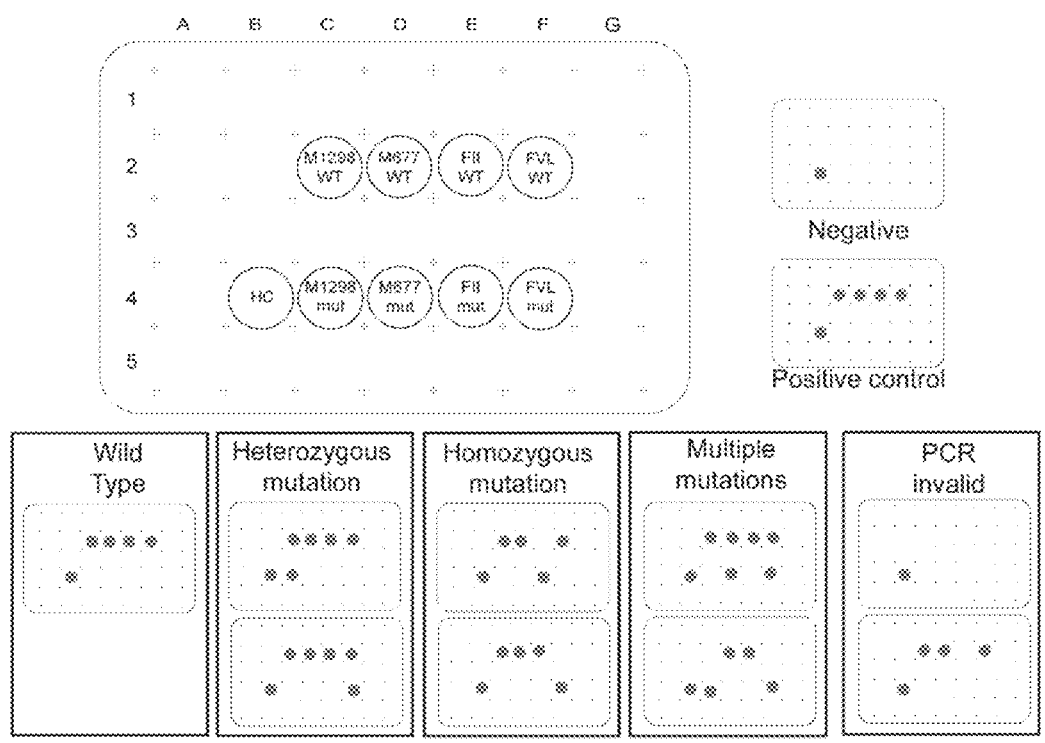

FIG. 28 shows one example of visual interpretation of the Thrombophilia array.

DETAILED DESCRIPTION OF THE INVENTION

The following terms shall be used to describe the present invention. In the absence of a specific definition set forth herein, the terms used to describe the present invention shall be given their common meaning as understood by those of ordinary skill in the art.

As used herein, the expression "Allelic-Specific-Oligonucleotide Reversed-Dot-Blotting (ASO-RDB)" refers to assays using Allelic-Specific-Oligonucleotide probes immobilized on a solid matrix capable of capturing target molecules for detection through hybridization processes.

As used herein, the term "flow-through hybridization" refers to the hybridization process utilizing the technology described in U.S. Pat. No. 5,741,647.

Figure 5:
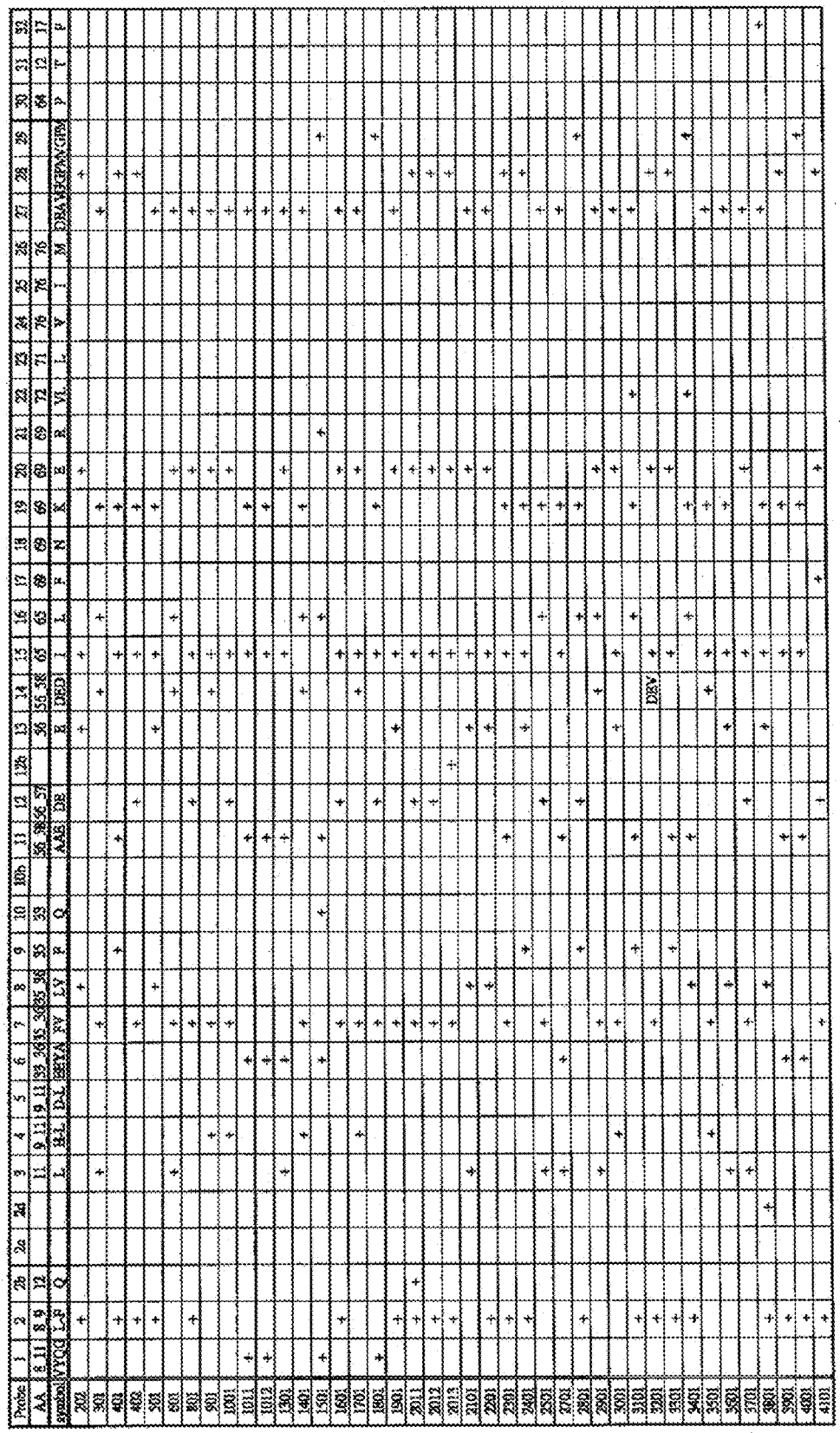
FIG. 5 shows a sample data for HLA-DPB genotyping identification.

As used herein, the term "flow-through hybridization device" or "flow-through device" refers to the device depicted in U.S. Pat. No. 6,020,187 and/or the lateral flow device depicted in FIG. 5 or any flow-through device designed subsequently.

HLA Genotyping

The following describes a method of the present invention for obtaining the HLA genotyping ASO probes and PCR primers from genomic sequence database, and for performing HLA genotyping analysis.

Select appropriate gene segments and determine appropriate PCR primers and ASO sites Select appropriate target sequence(s) to be analyzed by screening data from GenBank and/or by performing population screening by sequencing target genes or DNA segments to obtain SNP or ASO profile appropriate for HLA genotyping.

A method of the present invention for selecting appropriate target sequence(s) is detailed below:

(a) Find all the HLA DNA sequence data from GenBank according to their individual class (i.e., Class I or Class II) and subtypes (i.e., DR or DQ or DP, etc.). Align HLA DNA sequences based on individual classes and subtypes to determine the most polymorphic region(s) that will be appropriate for use in HLA genotyping.

(b) Within polymorphic region(s), identify PCR primer pair(s) that is conserved among the subtypes of interest so that when using these primers, the PCR products can always be amplified for all the subtypes of interest for further analysis using the flow-through hybridization process.

(c) To validate the usefulness of these primers, PCR amplification is performed using a large number of random samples to obtain statistically satisfactory data for positive amplification of the region(s) in question, and to ensure that any drop out of any allele does not result due to false negative amplification process. In addition to statistical validation, internal control (IC) is included to ensure that an inhibitor of PCR is not present in the test sample which will prevent the PCR amplification reaction. The design of IC (may be 1 or more) will depend on the test required. In the case of HLA and SNP fingerprinting, and genotyping of genes responsible for genetic diseases, the nature of IC sequence will be non-homologous to the human genome in question (i.e., a sequence totally unrelated to sequence in question). Since human cells are mostly diploid (except germline) genome, the concentration issue is much simpler because theoretically the concentration of the test loci should be either 1 (homozygous) or 0.5 (heterozygous). Hence, two different sequence fragments flanked by the same PCR primer sequences can be used for IC. This means that using a fragment different from that of the target fragments to be analyzed, one can use loci of known character of homozygous and heterozygous sequences within the fragment (that is two different probes (1 homo; 1 hetero-) in the fragment) as probes so that these IC concentration ratio can be calculated. Since the PCR amplification does not affect the relative concentration, the ratio of signal will be 2:1 theoretically. Any fluctuation will be seen as the hybridization efficiency. The two ICs with a ratio of 2:1 serves as the reference for homozygous and heterozygous, respectively, for the loci in question. If the observed result indicates only one allele, and the concentration in question is equal to or less than 0.5 of the homozygous IC or close to 1 compare to the heterozygous IC, the possibility of loss of heterozygosity should be investigated, meaning: may be one of the two chromosomes has lost or could not amplify. The expected result of ONE dot is homozygous which indicate the two chromosomes are the same, and therefore the concentration should be closer to the homozygous IC than that of the heterozygous IC. Hence, ICs will be important for obtaining accurate results since clinically dependable result is crucial for any diagnostic test.

Additional information on DNA data bank and alignments can be found in the reference section of this application (see Reference No. 5-6).

The procedures described herein for HLA genotyping can also be adopted by one of ordinary skill in the art reading the teaching herein for genotyping of other genes or DNA sequences of interest, or for determining SNP profiles for DNA fingerprinting/identification process performed in combination with flow-through hybridization process.

To maximize the efficiency of PCR amplification, the fragment length of the ASO probes is normally selected or kept as short as possible, preferably to within a few hundred basepairs.

If suitable primer pairs cannot be identified, adjustments on the components in the PCR reaction mixtures and the PCR processes, i.e. the PCR program, can be made to optimize the amplification reaction to ensure the production of amplicons during development of the genotyping process. Such development processes are apparent to persons of ordinary skill in the art after reading the teaching herein. In some cases a totally conserved sequences for PCR Primer cannot be found and degenerate primers or multiple primers for the same loci may have to be use. In these cases, appropriate adjustments to the PCR conditions are made to ensure that all loci will not be missed.

When unique region(s) for successful subtype differentiation cannot be identified, multiplex PCR may be required. The primer pairs are designed to Tm values within the operable range for successful annealing during the amplification process. As used herein, "Tm" means, for example, the temperature of the reaction where the concentration of DNA molecules in double strand as well as single strand is equal. Hence, at higher temperature more double strand DNA will become single strand, and conversely at lower temperature, more single strand molecule will anneal into double strand. For a given population where sequence data is not available, a population screening by direct DNA sequencing is usually performed. For example, a screening of a sample Chinese population was performed as follows: (a) Random samples of over a hundred subjects were amplified by PCR using two pairs of primers, followed by hybridization using the ASO Probes designed based the procedures described in the following sections. (b) The results were confirmed by DNA sequencing.

Using the data obtained above, the ASO sites to be used for genotyping are determined and selected. Determine whether the sites selected are indeed unique for HLA typing within a population using data obtained from GenBank or generated by sequencing random samples. The procedures for designing ASO probes and for validating the uniqueness of the probes are as follows:

(a) From the selected region(s) of the alignments for which satisfactory polymorphism among the subtypes are found, further search for a unique 20-30 nucleotide sequence or fragment is performed. The unique sequence or fragment is used as an allele specific oligonucleotide (ASO) probe to capture the amplified target by hybridization process in order to detect the presence of such unique HLA subtype. As used herein, "unique sequence or fragment" means, for example, that the sequence or fragment is completely homologous to only one sequence, among these subtype sequences.

(b) To verify that the ASO probe(s) is unique, the sequence is matched with all human DNA sequence data which are available in the GenBank or in its European equivalent to determine if indeed the ASO probe has 100% match with ONLY the HLA subtype of interest. This will ensure that at least (until new sequences are discovered) among the available data, the ASO probe(s) is unique for a given region.

(c) Since PCR fragment length is kept short to improve the efficiency of amplification, one ASO probe may not be sufficient to provide a definitive differentiation to determine the unique subtype. Hence, a set of multiple ASO probes within one PCR fragment and/or in different fragments using the multiplex PCR may have to be used to give a definitive genotyping classification. In this case, a specific pattern of the ASO array will be generated by the hybridization process for each of the given HLA subtypes. After thorough analysis of the data, the ASO sequences undergo validation using random human DNA samples.

Figure 2:
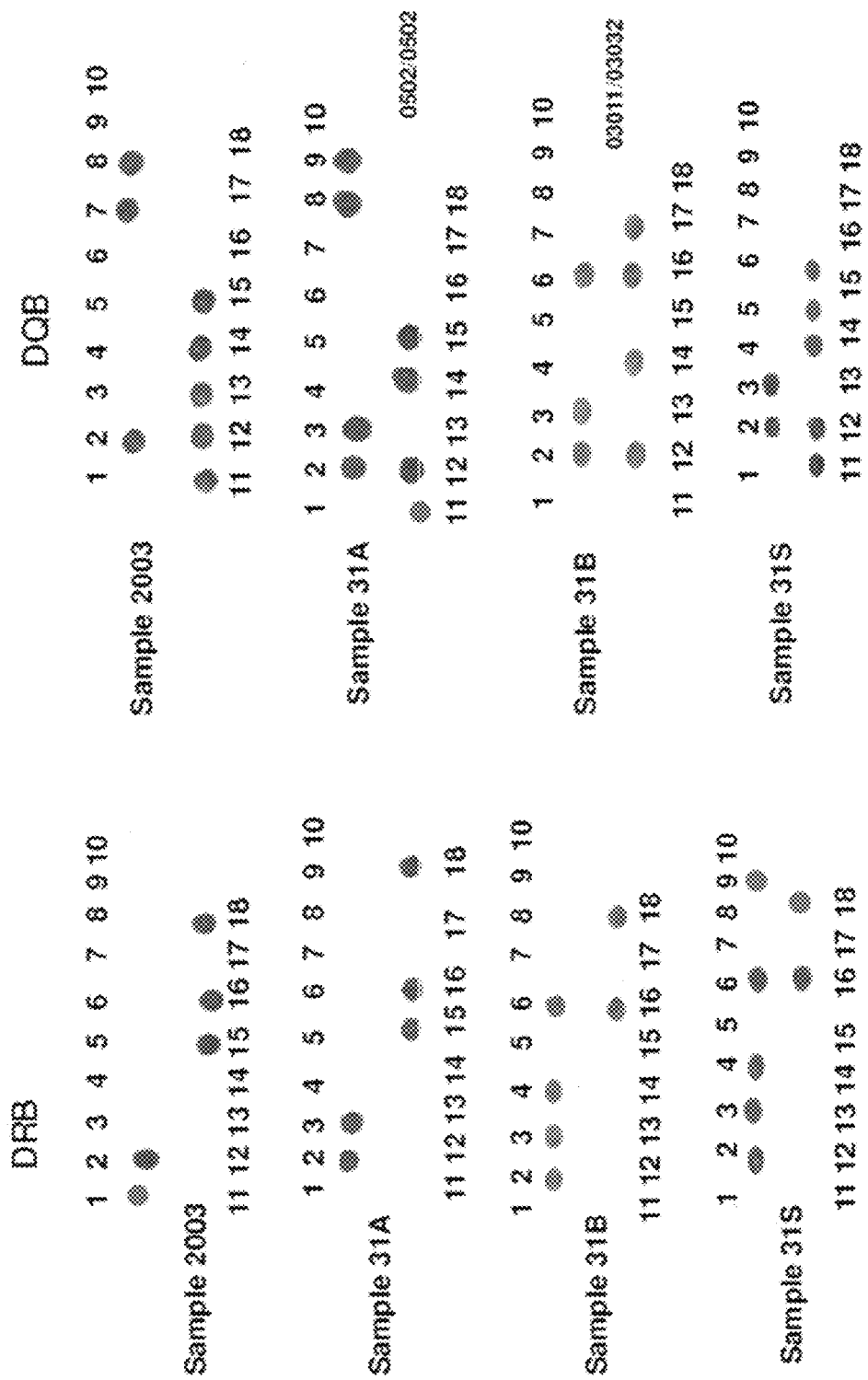
FIG. 2 shows a HLA-DQB genotype ASO detection profile obtained using a method of the present invention.
Figure 3:
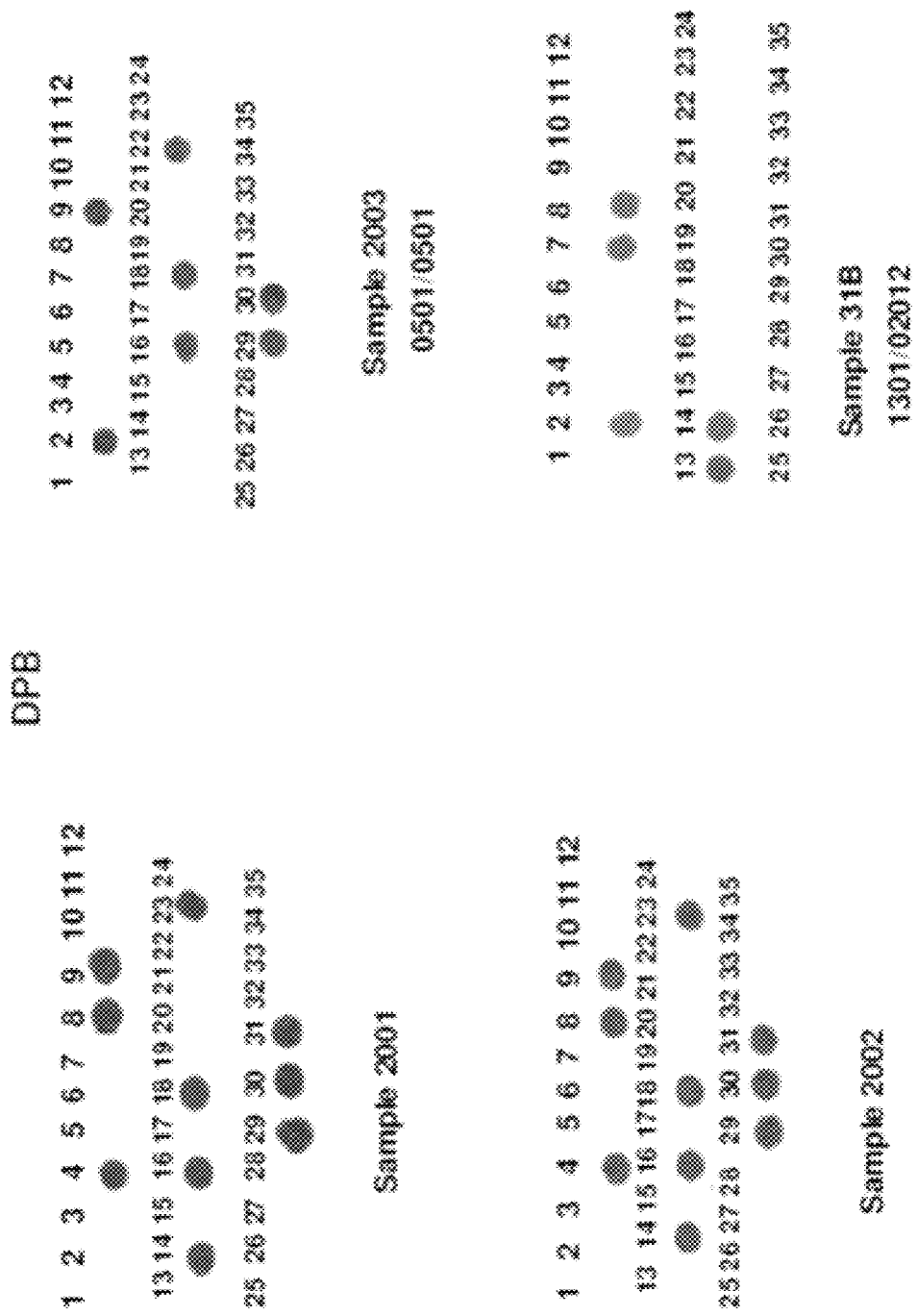
FIG. 3 shows a HLA-DPB1 genotype ASO detection profile obtained using a method of the present invention.

After the number of ASO capture probes is finalized for use, the array patterns for each of the genotypes are determined. Examples of specific array profiles are shown in FIGS. 2 and 3. The array profiles shown in FIGS. 2 and 3 were developed for determination of HLA DRB, DQB and DPB subtypes using 18 ASO probes and 35 ASO probes, respectively.

Figure 4:
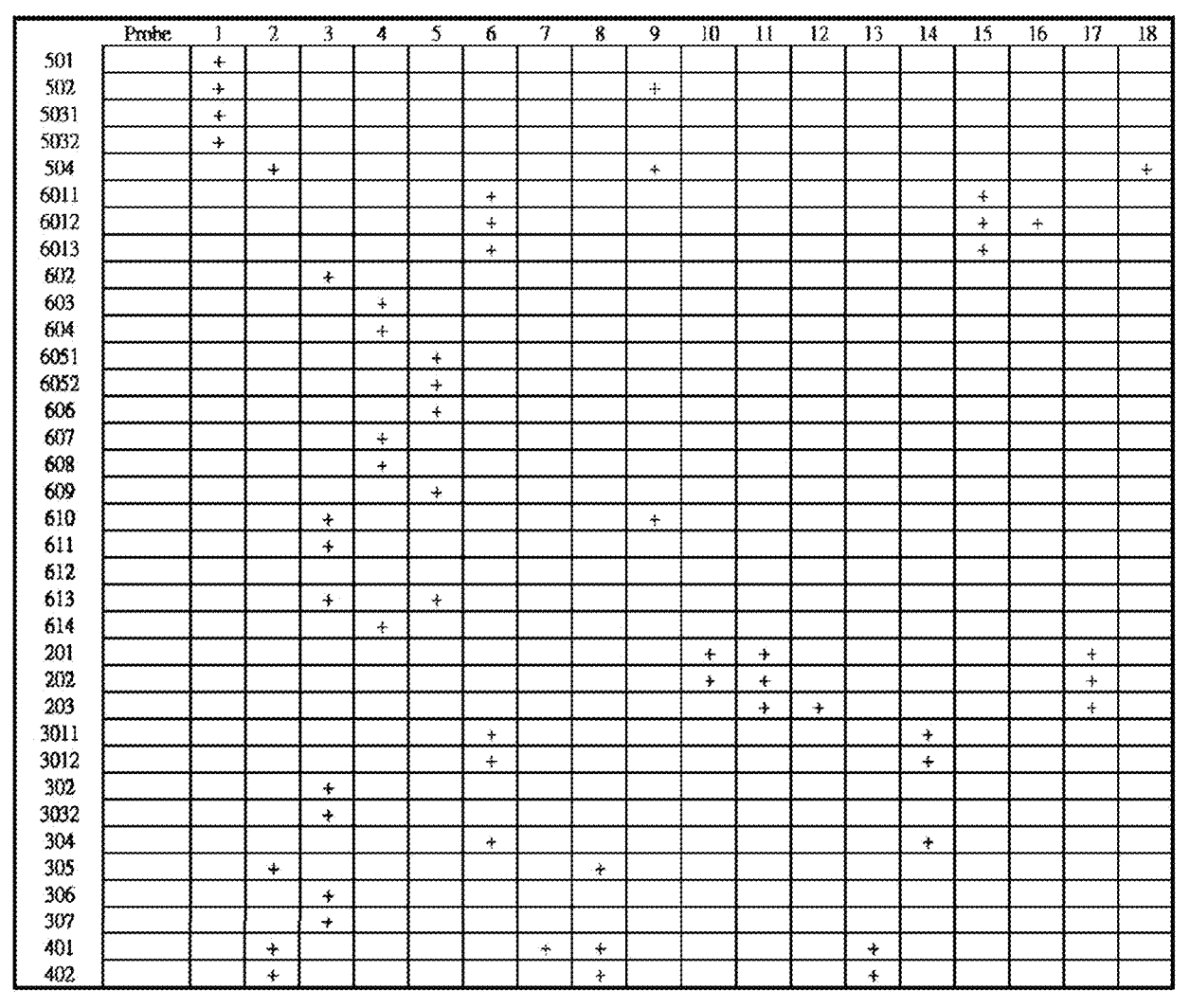

Similar procedures can be used for other genes and genetic materials from other organisms. The primer sequences and the number of ASO probes vary for different genes and for different applications. For example, human identification may require a 50 or more ASO array to obtain definitive identification (see FIGS. 3 and 4). The detection format can include an array of dots or linear lines depending on the configuration of the flow-through hybridization device.

Performing ASO-RDB Detection

ASO oligonucleotides are immobilized on a membrane or any suitable matrix for capturing the target loci. As used herein, "membrane" means, for example, any suitable matrix material capable of immobilizing ASO oligonucleotide probe(s) and porous enough for test solution containing the target nucleic acid molecules to pass through freely. In an embodiment, the membrane or matrix may be constructed of Nylon, NC, Biodyne, Porex, porous metal or durable gel matrixes.

Immobilization of the target sequence (or loci) can be achieved by covalent bonding, non-covalent (i.e., electrostatic, hydrophobic or any other interactions including UV cross-linking) interactions, or interactions through mediators such as receptors or antibodies. The membrane as shown in FIGS. 2 and 3 is Biodyne C using EDC to form covalent linkage between the membrane's COOH and the terminal $NH_2$-modified end of the ASO probes. Avidin-biotin linkage or ASO poly-T tailing for UV cross-linking is equally effective.

Target sequences are amplified using appropriate primers to generate enough amplicons to enable adequate analysis. The target molecules can be appropriately labeled for signal generation according to the method of signal detection used for final analysis. Labeling can be performed on one or both of the primers by covalent linkage of the label molecule at the 5' end or using one of the four dNTP labeled nucleotides during the PCR amplification process for extension labeling of the newly generated amplicons. The label molecule can be of any kind as long as the signal can be monitored and developed. Biotin coupled with avidin-enzyme conjugate can be used for color detection. Other suitable labeling systems including, but is not limited to, colloidal gold conjugate and fluorescence label, magnetic particles conjugate, quantum dots, chemiluminescence label molecules, or other suitable systems already developed or to be developed, may be used as well.

ASO profile analyses are performed using flow-through hybridization process such as the method described in U.S. Pat. No. 5,741,647. Hybridization is performed in the hybridization chamber with ASO capture probes coupled to the membrane. An ASO profile analysis is described below:

(a) Denaturing and contacting solution containing target DNA or sequence with membrane;

(b) Washing membrane with washing (or SSC or blocking) solution, preferably three times; and (c) Developing color for visual inspection or spectrometric measurements. For quantitative measurements, one can use a scanner and imaging software to perform the analysis. Alternatively, target DNA or sequence can be labeled with fluorescence dye and analyzed using a spectrometric imager immediately after the washing step.

The results are compared with known sequence data to ensure accuracy of genotyping assay.

Probes and testing conditions are further modified to improve the accuracy of genotyping assay, and RDB-ASO data is verified by DNA sequencing.

Validation

Validation is performed using random samples. A validation procedure of the present invention is described below:

As mentioned above, once the ASO capturing probe(s) are immobilized on a membrane, random DNA samples of sufficient number are used to perform PCR amplification. Hybridization of target sequence(s) or amplified and labeled DNA products or molecules is performed to generate an ASO array pattern.

HLA subtype and corresponding DNA sequence(s) are determined from ASO probes. Corresponding PCR samples are prepared for direct DNA sequencing. Agreement of the results obtained from DNA sequencing and from flow-through array is needed to validate the HLA genotyping assay. Samples for validating genotyping assay can be obtained from any randomly selected individuals. Once the samples have been obtained, true genotyping can be performed by DNA sequencing as stated in section 3.5. If sequencing data agree with those obtained from flow-through array, the validity of the data is confirmed. Further validation of genotyping assay can be performed through field tests, such as testing random samples, analyzing data and comparing statistically values such as sensitivity, specificity, positive predicted value or negative predicted value, at independent laboratories to evaluate the accuracy of genotyping assay.

The following is a method of the present invention for constructing a SNP database and developing a SNP genotyping assay.

Select SNP Sites and Determine the Power of Exclusion

As used herein, "power of exclusion" means, for example, the accuracy of the method in differentiating people or organisms. For instance, power of exclusion of 1 in 10 billion or 100 billion means that when using a selected number of SNP sites one can only expect to find two identical individuals in screening 10 or 100 billion individuals, respectively.

Select SNP sites and determine the power of exclusion. As used herein, "power of exclusion" means, for example, the accuracy of the method in differentiating people or organisms. For instance, power of exclusion of 1 in 10 billion or 100 billion means that when using a selected number of SNP sites one can only expect to find two identical individuals in screening 10 or 100 billion individuals, respectively.

Select appropriate SNP oligonucleotide probes for capturing specific target sequences to be analyzed either by screening data from GenBank or by performing population screening, i.e., direct DNA sequencing of target genes or target DNA segments, to obtain SNP profile and population frequencies.

From these data, identify the SNP sites to be used for fingerprinting based on polymorphic frequency, and determine whether or not the selected sites are indeed hot spots for mutation within a population by sequencing the samples obtained from random population screening. Determine the number of SNP probes required, and calculate total heterozygosity to determine the power of exclusion with the given number of SNP points used for the analysis profile pattern (i.e., the SNP dot array as shown in FIG. 9).

Power of exclusion depends on the number of SNP in a given loci. For example, in a given loci, if 2 different bases, e.g., G and A, are found in a sample population at 50% each. The probability is ½. If 50 of such sites can be found (these sites are randomly distributed and are not linked to each other in the chromosome) the differentiation power will be ½ to the power of 50.

Perform SNP Profile Pattern (a Combination of SNP Array Showing the Array of Corresponding Genotypes in Each Loci of that Individual) Detection Design appropriate primers for amplification, and select appropriate SNP-probes for hybridization detection after the loci are screened and selected as described above.

Amplify target sequence(s) and perform SNP profile analyses using flow-through hybridization process such as the method described in U.S. Pat. No. 5,741,647.

Compare the data obtained above with known sequence data to evaluate the accuracy of the SNP genotyping analysis.

Modify SNP probes and testing conditions to improve the accuracy of the SNP genotyping analysis. RDB SNP data are verified by DNA sequencing.

Validate the method with random samples.

HPV Genotyping

In one embodiment, the present invention provides a method of rapid identification of human papillomavirus (HPV) genotypes. The invention disclosed herein can also be applied for screening and detection of other viruses, bacteria, parasite or other pathogens. For example, the present invention can be used for genotyping of TB, HBV, HCV, SARS and respiratory infectious viruses individually or in combinations.

In one embodiment, the method for rapid detection of human papillomavirus (HPV) comprises the steps of: (a) obtaining a sample comprising a template nucleic acid; (b)

amplifying the template nucleic acid with primers having the sequences of SEQ ID NOs:116-118, thereby generating HPV L1 amplicons; and (c) hybridizing the HPV L1 amplicons with immobilized oligonucleotide probes selected from the group consisting of SEQ ID NOs:121-173, wherein the resulting hybridization profile would indicate the presence of HPV, including HPV high risk (HR) HPV and low risk (LR) HPV. In one embodiment, the primers comprise a signal generating label. In another embodiment, the primers further comprise primers complimentary to an internal control (e.g. primers having the sequences of SEQ ID NOs:119-120). In another embodiment, the oligonucleotide probes further comprise probes capable of capturing generic HPV viral DNA (e.g. probes having the sequences of SEQ ID NOs:170-173), wherein the probes comprise Locked Nucleic Acid (LNA™). The use of LNA™-modified nucleotides in the present invention is to increases the thermal stability and the target specificity of the oligonucleotides probes in HPV detection.

In one embodiment, the hybridization of the HPV L1 amplicons with the plurality of immobilized oligonucleotide probes is carried out in a flow-through process or a lateral flow-through process. In one embodiment of a flow-through process, the sensitivity of the hybridization depends on the ratio of the area comprising the probes to the total area of the membrane of the array. In one embodiment of a lateral flow-through process, the sensitivity of the hybridization depends on the ratio of the cross sectional area comprising the probes to the total cross sectional area of the membrane across the flow direction.

In one embodiment, the above method can detect one or more of the following HPV genotypes: HPV6, 11, 16, 18, 26, 31, 33, 35, 39, 40, 42, 43, 44, 45, 51, 52, 53, 54, 55, 56, 57, 58, 59, 61, 66, 68, 70, 71, 72, 73, 81, 82, and 84. The HPV genotypes can be separately detected, or the genotypes are detected collectively in one or more groups (see e.g. FIGS. 15-18). In one embodiment, HPV 16 and 18 may be identified separately, wherein HPV31, 33, 35, 39, 45, 51, 52, 56, 58, 59, 73, 82 can be detected collectively in one or more groups (see FIGS. 16-18), e.g. HPV31, 33, 35, 39 are detected as one group, HPV45, 51, 52, 56 are detected as a second group, and HPV58, 59, 73, 82 are identified as a third group. In another embodiment, the method can further detect HPV 6, 11, 26, 40, 42, 43, 44, 53, 54, 55, 57, 61, 66, 70, 71, 72, 73, 81 and 84 collectively in one or more groups (see e.g. FIG. 18).

The present invention also provides a kit for human papillomavirus (HPV) genotyping, comprising primers having the sequences of SEQ ID NOs:116-118 and oligonucleotide probes selected from the group consisting of SEQ ID NOs: 121-173. In one embodiment, the primers further comprise a signal generating label. In another embodiment, the primers further comprise primers complimentary to an internal control (e.g. primers having the sequences of SEQ ID NOs:119-120). In yet another embodiment, the oligonucleotide probes further comprise probes capable of capturing generic HPV viral DNA (e.g. probes having the sequences of SEQ ID NOs:170-173). In one embodiment, the kit can detect one or more of the following HPV genotypes: HPV6, 11, 16, 18, 26, 31, 33, 35, 39, 40, 42, 43, 44, 45, 51, 52, 53, 54, 55, 56, 57, 58, 59, 61, 66, 68, 70, 71, 72, 73, 81, 82, and 84. The HPV genotypes can be separately detected, or the genotypes are detected collectively in one or more groups (see e.g. FIGS. 15-18).

In one embodiment, the present invention provides a method for detecting the presence of multidrug-resistant *Mycobacterium tuberculosis* (DR-MTB), comprising the steps of: (a) obtaining a sample comprising a template nucleic acid; (b) amplifying the template nucleic acid with primers selected from the group consisting of SEQ ID NOs:174-181, thereby generating DR-MTB amplicons; and (c) hybridizing the amplicons with oligonucleotide probes selected from the group consisting of SEQ ID NOs:182-200, wherein the resulting hybridization profile would indicate the presence of multidrug-resistant *Mycobacterium tuberculosis*. In one embodiment, the primers comprise a signal generating label. In one embodiment, hybridization of the amplicons with the plurality of oligonucleotide probes is carried out in a flow-through process or a lateral flow-through process.

In one embodiment, the above method can detect the presence of multidrug-resistant *Mycobacterium tuberculosis* having one or more of the following mutations: one of seven mutations in the rpoB gene; one of two mutations in the katG gene; and one mutation in the inhA gene.

The present invention also provides a kit for detecting the presence of multidrug-resistant *Mycobacterium tuberculosis*, comprising primers selected from the group consisting of SEQ ID NOs:174-181 and oligonucleotide probes selected from the group consisting of SEQ ID NOs: 182-200.

The present invention also provides a method of detecting beta-globin mutations in a subject having beta-thalassemia, comprising the steps of: (a) obtaining from the subject a sample comprising a template nucleic acid; (b) amplifying the template nucleic acid with primers selected from the group consisting of SEQ ID NOs:201-205, thereby generating beta-globin amplicons; and (c) hybridizing the amplicons with oligonucleotide probes selected from the group consisting of SEQ ID NOs:206-240, wherein the resulting hybridization profile would indicate the genotypes of beta-thalassemia. In one embodiment, the primers comprise a signal generating label. In one embodiment, hybridization of the amplicons with the plurality of oligonucleotide probes is carried out in a flow-through process or a lateral flow-through process. In one embodiment, the above method can detect one of twenty one beta-globin mutations.

The present invention also provides a kit for detecting beta-globin mutations, comprising primers selected from the group consisting of SEQ ID NOs:201-205 and oligonucleotide probes selected from the group consisting of SEQ ID NOs: 206-240.

The present invention also provides a method for detecting the presence of HBV, comprising the steps of: (a) obtaining a sample comprising a template nucleic acid; (b) amplifying the template nucleic acid with primers selected from the group consisting of SEQ ID NOs:241-244, thereby generating HBV amplicons; and (c) hybridizing the amplicons with oligonucleotide probes selected from the group consisting of SEQ ID NOs:245-260, wherein the resulting hybridization profile would indicate the presence of HBV. In one embodiment, the primers comprise a signal generating label. In one embodiment, hybridization of the amplicons with the plurality of oligonucleotide probes is carried out in a flow-through process or a lateral flow-through process.

In one embodiment, the above method can detect the presence of HBV having a genotype selected from the group consisting of HBV genotypes A to H. The present invention also provides a kit for detecting the presence of HBV, comprising primers selected from the group consisting of SEQ ID NOs:241-244 and oligonucleotide probes selected from the group consisting of SEQ ID NOs: 245-260.

The present invention also provides a method for detecting the presence of sexually transmitted diseases in a subject, comprising the steps of: (a) obtaining from the subject a sample comprising a template nucleic acid; (b) amplifying the template nucleic acid with primers selected from the group consisting of SEQ ID NOs:263-286, thereby generating amplicons; and (c) hybridizing the amplicons with oligonucleotide probes selected from the group consisting of SEQ ID NOs:287-298, wherein the resulting hybridization profile would indicate the presence of sexually transmitted diseases. In one embodiment, the primers comprise a signal generating label. In one embodiment, hybridization of the amplicons with the plurality of oligonucleotide probes is carried out in a flow-through process or a lateral flow-through process.

In one embodiment, the above method can detect the presence of sexually transmitted diseases caused by an organism selected from the group consisting of *Trichomonas vaginalis, Chlamydia trachomatis, Neisseria gonorrhoeae, Mycoplasma genitalium, Mycoplasma hominis, Ureaplasma urealyticum, Ureaplasma parvum, Treponema pallidum*, Herpes simplex virus 1, Herpes simplex virus 2, Human papillomavirus type 6, and Human papillomavirus type 11. The present invention also provides a kit for detecting the presence of sexually transmitted diseases in a subject, comprising primers selected from the group consisting of SEQ ID NOs:263-286 and oligonucleotide probes selected from the group consisting of SEQ ID NOs: 287-298.

The present invention also provides a method for detecting mutations related to thrombophilia, comprising the steps of: (a) obtaining a sample comprising a template nucleic acid; (b) amplifying the template nucleic acid with primers selected from the group consisting of SEQ ID NOs:299-306, thereby generating amplicons; and (c) hybridizing the amplicons with oligonucleotide probes selected from the group consisting of SEQ ID NOs:307-314, wherein the resulting hybridization profile would indicate the presence of mutations related to thrombophilia. In one embodiment, the primers comprise a signal generating label. In one embodiment, hybridization of the amplicons with the plurality of oligonucleotide probes is carried out in a flow-through process or a lateral flow-through process.

In one embodiment, the above method can detect mutation at a gene selected from the group consisting of Factor V Leiden, Factor II (Prothrombin), and Methylenetetrahydrofolate Reductase. The present invention also provides a kit for detecting the presence of mutations related to thrombophilia, comprising primers selected from the group consisting of SEQ ID NOs:299-306 and oligonucleotide probes selected from the group consisting of SEQ ID NOs: 307-314.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

Test Procedures

Isolation of DNA

The following protocols are recommended, but alternative procedures which are readily apparent to one of ordinary skill in the art and which are equally effective may be employed. Nucleated cells such as white blood cells or tissues are washed with PBS, centrifuged, and the supernatant is removed. The pellet is re-suspended in 200 µl PBS. DNA extraction is performed with QIAamp DNA mini kit (QIAGEN) following Blood and Body Fluid Spin protocol as recommended by the manufacturer. Other commercially available kits for isolating DNA may also be used. However, DNA isolation procedures that produce purified DNA that do not contain DNA polymerase inhibitor are crucial to ensure efficient amplification. Elute DNA in 50-200 µl Buffer AE and store at −20° C. until use.

PCR Amplification

Since PCR is extremely sensitive process, special care must be taken to prevent cross contamination and/or to prevent false positive results. Hence, the following guidelines should be observed: Wear surgical gloves at all times when performing PCR procedures. Preferably, prepare PCR reaction mixtures in a pre-PCR area or a clean PCR preparation station where no amplification products are present. PCR reaction and hybridization should be performed in separate areas. For example, hybridization should be performed in a post-PCR area.

Use 70% ethanol and paper towel to clean the working bench/area. Use 70% ethanol and paper towel to clean all the pipettes before starting PCR amplification. Use filtered/sterile tips for all pipetting steps. Never reuse any tips.

PCR is just one of the many techniques which can be used for amplification. Other amplification techniques, which are readily apparent to one of ordinary skill in the art, such as various methods for isothermal amplification using appropriate primers to amplify target sequence(s) to obtain sufficient quantity of target sequence(s) (or DNA molecules) to carry out flow-through array detection may be used.

PCR reactions are performed using, for example, commercially available polymerase AmpliTaq™ Gold (Applied Biosystem). Five primers pairs (1 pair used for amplifying the DR genes, i.e., forward primer DRB-F1: 5'-ATCCTTCGTGTC-CCCACAGCACG-3' [SEQ ID No. 97] and the reversed primer DRB-R1: 5'-GCCGCTGCACTGTGAAGCTCTC-3' [SEQ ID No. 98]; 1 pair used for amplifying the DQ genes, i.e., the forward primer is DQB-E2-F2: 5'CGGTGATTC-CCCGCAGAGGAT-3' [SEQ ID No. 99] and the reversed primer is DQB-E2-R2: 5'-CCACCTCGTAGTTGT-GTCTGC-3' [SEQ ID No. 100]; and 3 pairs used for amplifying the DP gene, the forward primers [SEQ ID NOs. 101-103] and the reversed primers [SEQ ID NOs. 104-106]) are individually 5'-end labelled with biotin. Other appropriate labelling methods described above can also be used. In 25 µl reactions, prepare a PCR master mix as follows (This example is intended to illustrate one particular program for PCR amplification reaction of the present invention. If other SNP primer sequence(s) are used, the condition for PCR and hybridization must be optimized):

| | Each reaction (µl) | 10 reactions |
|---|---|---|
| PCR-Mix | 19.00 | 190.0 |
| DNA Taq Polymerase | 1 ul (1 unit) | 10 ul (10 units) |
| DNA Template | 5 (~100 ng) | — |
| Total | 25 | 200 |

Amplification program was optimized using PE 9700 thermal cycler:

For PE 9700 (or MJ thermal cycler):

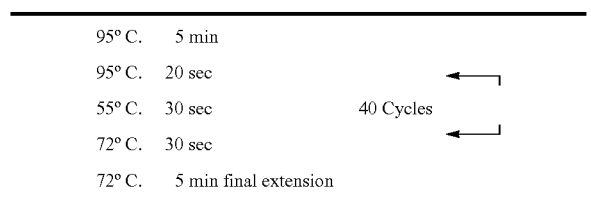

When using different primers or other thermal cycler, modifications to the cycling program may be required.

Quality Control for PCR

It is important to have a positive control and a negative control in every PCR analysis. Positive control is needed to demonstrate the efficiency and specificity of PCR, and negative control is needed to determine whether PCR reagents are contaminated. Internal controls are also needed to provide proper interpretation, and to ensure the dependability and accuracy of the data. The type and the number of IC depend on the type or nature of the test needed. The IC can be used to track each step of the hybridization reaction or procedure. For example, IC can be used to determine whether a sample was added or whether any inhibitors are present in a sample which will prevent PCR reaction from working properly. IC can also be used to track the efficiency of the reaction, or to determine the concentration of target molecule in a semi-quantitative or quantitative manner.

If a quantitative or semi-quantitative measurement is needed, the detection array or membrane can be prepared with a signal generating internal control (IC) onto the membrane to provide a detectable signal at predetermined concentrations when a preprogrammed or predetermined condition has been met. In such embodiment, the IC is developed simultaneously with the test samples after hybridization. In another embodiment, additional IC can be added into the PCR reaction mix to indicate the intrinsic PCR efficiency. This can serve also as an internal control to indicate the presence or absence of inhibitor within the PCR reaction.

The IC system in the PCR reaction mix of the present invention provides several advantages. Since the PCR reaction is carried out in the same reaction tube, the absence of IC and test sample signal indicates the presence of an inhibitor. If the same primer sequences for IC and test samples are used for the PCR amplification, it can serve as an intrinsic control for PCR reaction efficiency. IC can also be used to determine the detection limits or cut off value of the PCR reaction and/or the efficiency of the hybridization process, and to provide an indication of whether hybridization was successfully completed. In addition, IC can be used to determine whether reagents for signal development are acceptable or prepared properly, and whether proper procedures were followed during hybridization.

Preparations Prior to Hybridization:

(1) Pre-warm hybridization solution (i.e., 2×SSC or any commercially available solution/product) to 42° C. in a water bath before use. If precipitate is present in solution B (SSC+ 0.5% SDS), dissolve the precipitate by incubating solution B at 42° C. until the precipitate is dissolved. Keep the temperature at 42° C. through out the hybridization process to maintain set stringency.

(2) Prepare NBT/BCIP working solution by dissolving a tablet in 10 ml of solution C or PBS buffer (phosphate buffer saline). Protect the diluted working NBT/BCIP solution from light and store any unused solution at 4° C.

(3) Equilibrate hybridization solution (2×SSC+0.05% tween 20) to room temperature.

(4) Denature all biotinylated PCR products by heating at 95° C. for 5 min, and then chill on ice immediately for at least 2 min Hybridization Set-Up For the flow through hybridization studies, one can use the direct flow through device described in U.S. Pat. No. 6,020, 187 or a lateral flow device described in this application. Switch on hybridization device to preheat at 42° C. filled with distilled water.

Place the detection membrane(s) which are embedded with capture probe(s), such as those listed in the sequence listing below, in the hybridization chamber. Secure the membrane(s) with, for example, a cover lid.

Hybridization of PCR Products

When the temperature reaches 42° C. (+/−0.5° C.), deliver 1 ml of the pre-warmed hybridization solution for pre-hybridization to cover the membrane. Incubate for at least 2 minutes with the cover closed to prevent heat loss during pre-hybridization. This is to ensure temperature equilibrium at the set temperature.

Add 0.5 ml of the pre-warmed hybridization solution to each denatured PCR products separately for testing, and add the DNA samples into designated well. Contacting DNA samples which contain the target sequence(s) with membrane surface and incubate at 42° C. for 5 minutes, and then allow DNA samples which to flow through the membrane. Hybridization is normally completed within 30 seconds. The 2-5 minutes incubation period ensures that the temperature of the DNA samples will reach the set temperature.

Wash the membrane with 3×0.8 ml of hybridization solution.

Color Development

Set temperature to 37° C. Start pump, and immediately begin dispensing 0.5 ml of blocking solution. Stop pump. Add another 0.5 ml of blocking solution and incubate for 5 min, then pump out the solution.

Turn off pump and add 0.5 ml of the enzyme conjugate. Let the membrane sit for 3 min. Color development works well between 25-37° C. Start pump. Wash the membrane thoroughly, preferably four times, with 0.8 ml of buffered saline solution at pH 7.4.

Turn off pump and add 0.5 ml of the NBT/BCIP solution (from Roche).

Cover lid. Incubate for about 5 minutes or until color develops. Note: DO NOT incubate for over 10 minutes.

Turn pump on to remove NBT/BCIP solution. Wash the membrane, preferably three to four times, with 1 ml of solution B after the color has completely developed. Rinse membrane with 2 ml of dH$_2$O once.

Inspect results as soon as possible, preferably within 1 hour, by direct visualization, or scan the image for semi-quantitative detection.

Result Interpretation

Figure 1:
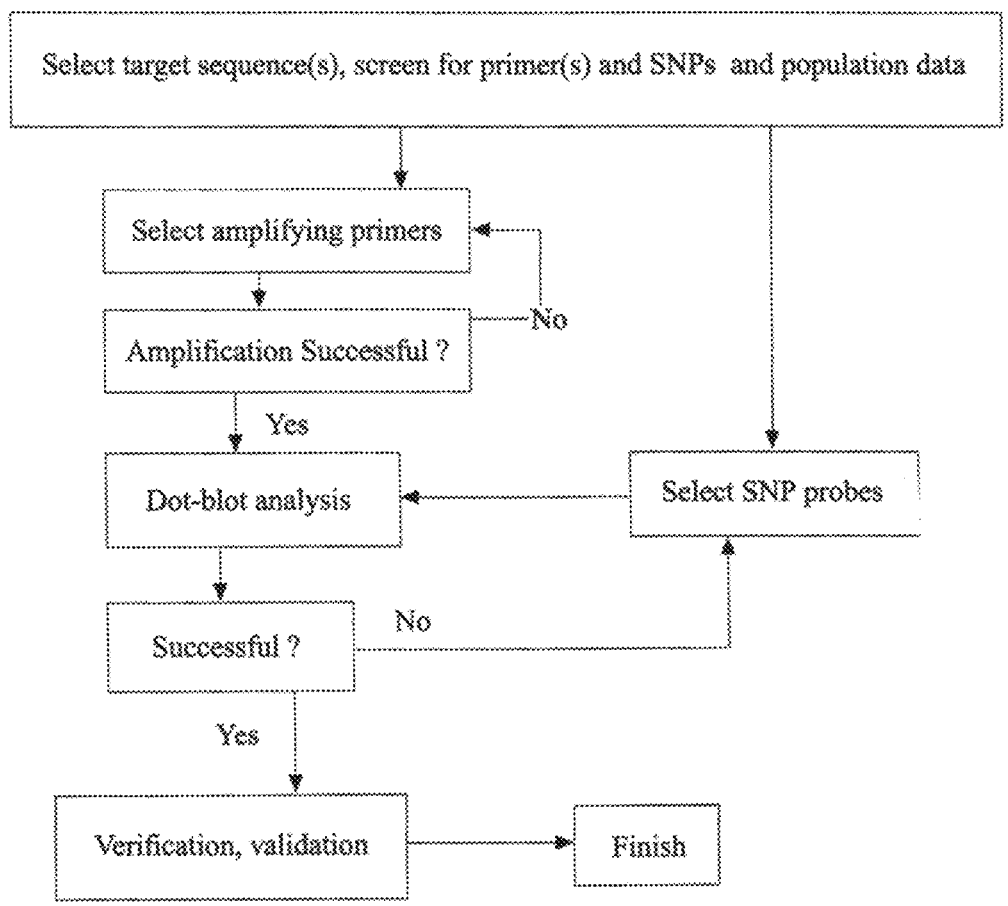
FIG. 1 shows a method of the present invention for constructing an ASO probe and PCR primer database.
Figure 1A:
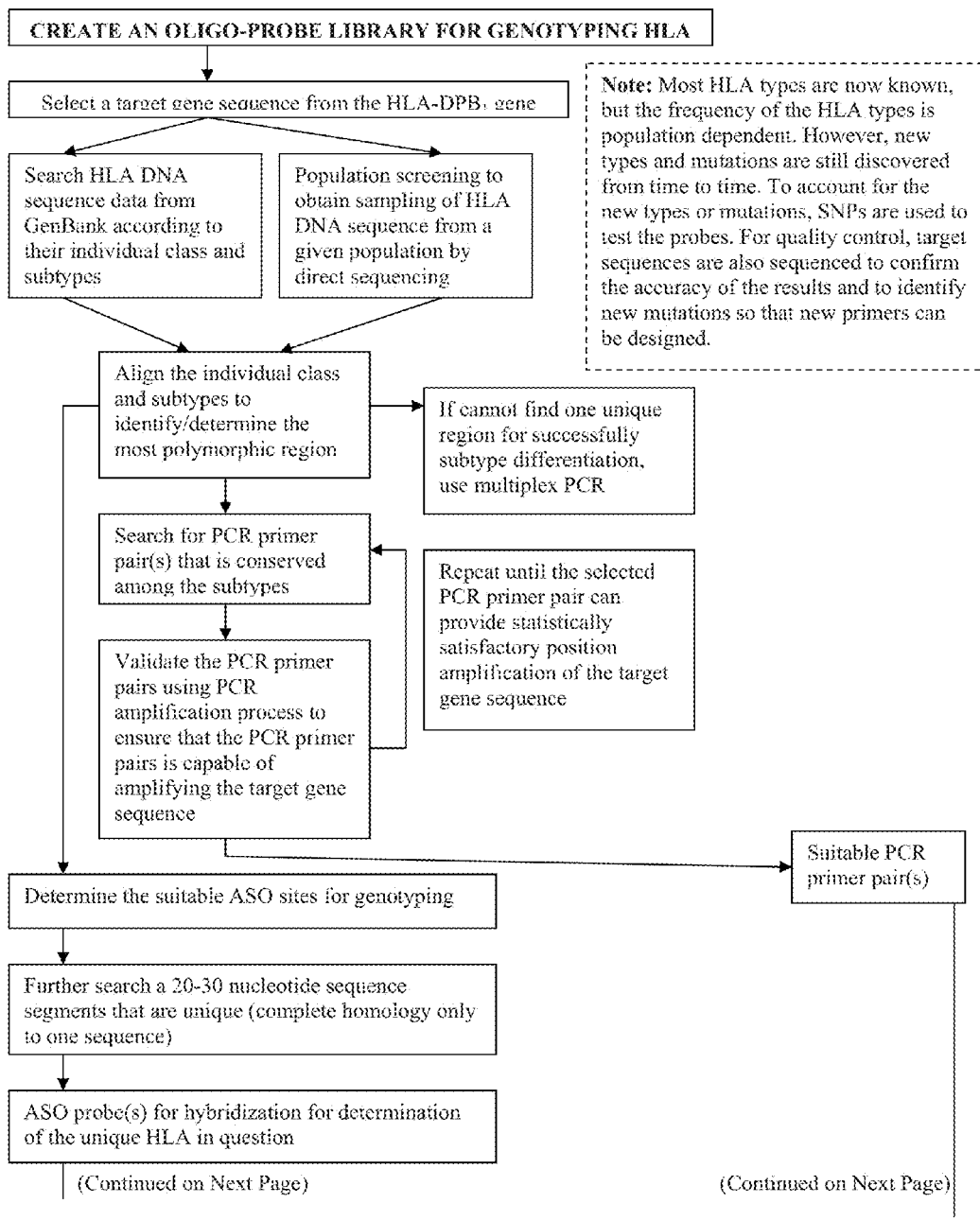
FIG. 1A shows a method of the present invention for building an Oligo-Probe Library for HLA Genotyping.

The presence of a clearly visible dot indicates a positive result. A total of 96 ASO probes (DRB: 29; DQB1: 24 and DPB1: 43), corresponding to SEQ ID 1-96 in the sequence listing for the HLA cluster, and five PCR primer pairs, corresponding to SEQ ID NO 97-106 in the sequence listing for amplification had been designed according to the scheme in FIGS. 1 and 1A. The ASO probes and primer pairs have been evaluated and determined to be suitable for the classification of the HLA DR, DQ and DP genes. FIG. 2 shows the typical results of HLA-DRB and DQB loci using 18 ASO probes each respectively and the classification into genotypes labeled in each of the array profile patterns. Similarly, FIG. 3 shows the results for HLA-DPB1. In this gene, 35 ASO probes of 43 designed (32 probes were finally adopted after screening and validated from random samples) were used in generating the array profile pattern. ASO-HLA DR, DQ and DP data summary are given in FIGS. 4 and 5. Genotypes and allele frequencies are given in Table 1 and 2. All data obtained from reversed dot blot array by flow through hybridization (which used a total of 141 random human samples) were separately confirmed with DNA sequencing. In principle, any known ASO (or SNP) oligonucleotides of any organisms with adequate data to perform genetic analysis can be tested, identified or detected by the rapid, genotyping flow-through hybridization method of the present invention.

Hybridization results are obtained within minutes, which translate into at least a ten-fold increase in speed over conventional hybridization techniques.

Example 2

Simplified Genotyping Protocols and Devices

The flow-through DNA hybridization method and device as described in the U.S. Pat. Nos. 5,741,647 and 6,020,187, respectively, reduces hybridization time from many hours or days to minutes (the whole hybridization assay can be completed in 5-30 minutes depending the method used to generate detection signal). The device is also inexpensive to manufacture, and uses 10 times less reagents than convention hybridization devices which will lead to more affordable DNA diagnosis technology.

The present invention provides an inexpensive platform for studying the nucleic acids, proteins and other chemical interactions using a low-density array format. As illustrated above, the genotyping method of the present invention has been shown to provide significant improvements over conventional hybridization processes.

The present invention further provides additional improvements over existing flow-through hybridization techniques. For example, the hybridization device of the present invention includes a detection membrane, such as the membrane shown in FIG. 6B in a 4×6 array format. With the use of the ELISA 96 wells format, in which each well can be prepared with a 5-dot matrix array, for processing 96 samples and 5 different analysts to simultaneously. This increases the analysis throughput substantially.

The array format may be adapted by one of ordinary skill in the art to accommodate additional wells for analyzing a larger set of nucleotide sequences rapidly and inexpensively. The hybridization device of the present invention is a breakthrough in rapid DNA diagnostics. A lateral flow and miniature embodiment of the device of the present invention is depicted in FIG. 7.

Significant improvements on the hybridization protocols are also disclosed which include:

(i) Elimination of the pre-hybridization step in which the blocking and hybridization steps are combined using an improved reagent mixture (i.e., DNA samples are placed in hybridization solution and flow-through detection membrane without pre-hybridization)

(ii) a single-step hybridization process in which the target sequences or molecules are labeled with fluorescence tags, quantum dot, colloidal gold particles, magnetic particles or other appropriate labeling tags to eliminate the enzyme-link conjugate substrate color development step. These improvements will enable a technician to complete the entire hybridization process in 5 minutes or less. Hence, the method of the present invention should provide further savings in terms of time and reagent cost.

Example 3

Single Nucleotide Polymorphism (SNP)-Based Genotyping

Eight gene clusters and 55 segments from 50 to 400 individual samples were sequenced to identify sites suitable for SNP genotyping. FIG. 9 shows one of the panels which were used for fingerprinting. Results were compared with STR Profiler Plus fingerprinting kit (Applied Biosystems, Inc.) to ensure accuracy. FIG. 10 shows the loci used in the fingerprinting method as shown in FIG. 8. Other probes and primers for other candidate genes/sequences may be readily determined by one of ordinary skill in the art following the teaching of this application. Genes which have been tested include Globin genes for Thalassemia, BRCAs, ApoE, Collagens, p53, G6PD deficiency alleles and HLA DP, DQ and DR. Any known SNPs of any organisms with adequate data to perform genetic analysis can be tested or detected using the rapid SNP genotyping process of the present invention.

To identify the DRB genotypes, the PCR were carried out with the primer pair of DRB-F1: 5'-ATCCTTCGTGTC-CCCACAGCACG-3' [SEQ ID No. 97] and DRB-R1: 5'-GC-CGCTGCACTGTGAAGCTCTC-3' [SEQ ID No. 98] and a 29 ASO probes were tested of which 18 were found to be best for the identification of the HLA-DRB alleles. In the case of DQB1 genotypes, PCR is carried out using DQB-E2-F2: 5'-CGGTGATTCCCCGCAGAGGAT-3' [SEQ ID No. 99] and DQB-E2-R2: 5'-CCACCTCGTAGTTGTGTCTGC-3' [SEQ ID No. 100] as primers which are able to generate a 260 bp. The 24 SSO probes are used as capture probes for this DQB1 classification during hybridization.

To identify DPB1 genotypes, a total of 43 ASO probes were tested of which a set of 35 SSO Probes are shown as the example. In order to amplify a target gene or sequence to a detectable level for hybridization, multiplex PCR amplifications are carried out with a set of primers. Primer1-f, Primer2-f and Primer3-f are used for forward priming. Primers4-r, Primer5-r and Primer6-r are used for reversed priming. These primer pairs are able to generate about 264 bp amplicons of 5' end-labeled for hybridization with color development to identify the genotypes in question.

Example 4

HPV Genotyping

FIG. 14 shows the oligonucleotide probes (SEQ NO:121 to 167) used to capture the L1 of specified HPV amplicons and PCR primers (SEQ NO:116 to 118) for the amplification of the HPV L1 region to achieve HPV detection by DNA hybridization in the membrane Array format as shown. To ensure PCR reaction goes properly and that inhibitor is absent an internal control primer pair (SEQ NO:119 and 120) is included for co-amplification of HPV viral genome. Furthermore the HC, a biotinated oligonucleotide is immobilized onto each array as control reagent for color development.

The HPV genotyping assay utilizing the Flow-through membrane array format is fast, simple to perform and the flow-through device with the exchangeable separator makes it easy to change the array format to accommodate different number of array formats. By varying the size and the number of dots one can optimize the usage of the reaction chamber to achieve maximized cost saving. In one embodiment, the current 5×6 dots array used for the HPV 33 genotyping kit will give 15 assays per run. In another embodiment, the 4×5 dots array format can be expanded into 30 sample assay per run. The 2×3 dots array format is ideal for high throughput screening because it can run 64 arrays using the same device having the size of an ELISA plate used in validating the assay, a very efficient and affordable alternative for screening HPV inflection. In yet another embodiment, array membrane can also be designed for using the miniature hybridization device depicted in FIG. 7.

FIG. 15A shows a typical assay of the 5×6 dot assay format in which a single type of HPV infection is clearly identified. In FIG. 15B, a multiple infections was seen. The array shown in FIG. 16 is the 4×5 array format for the identification of the 14 HR-HPV genotypes recommended for screening in cancer prevention program. FIG. 17 is the 2×3 dot assay format. The HPV detection kit shown in FIG. 17A serves three purposes: (a) clearly identify whether the infection is HPV 16 or 18 or both which cover about 70% of HPV infection. Knowing this will allow the clinician to make appropriate diagnosis, prognosis and treatment, including decision on vaccination despite the presence of HPV infections; (b) HR-HPV dot covering the 12 HR-HPV as a group would provide the clinical data widely recommended by worldwide authorities such as WHO to be the most effective way for cervical cancer prevention; and (c) the Generic dot serves as general HPV screening whereby not only the 14 cancer-causing HR-HPV, others HPV of intermediate, lower or unknown types can also be detected as early screening for HPV prevention. In addition this dot can serve as another internal repeat that ensures test assay confirmation unique to all currently found in the market. Hence this new format of HPV kit will be the most comprehensive, despite its low cost, for HPV and cervical cancer screening and prevention.

PCR Amplification, Signal Development, Result Interpretation and Validation

PCR amplification, hybridization and color development and result interpretation were done similar to what has been described above except that the primer pair used was SEQ NO:116-118 with higher Taq polymerase concentration to compensate for the activity of degenerate primers pairs. It is obvious to one skilled in the art that the image signal can be generated by other development techniques and that results can be interpreted by image scanning technique for quantitative result. However, absolute quantitative result is either not attainable for similar assays with sample variability or unnecessary; visual inspection is sufficient because in HPV initial screening the presence or absence of the virus is enough and affordability is most essential. In the present invention, the HPV L1 region is used for the assay. The forward primer (HPVF) is Biotin-5'-GCMCAGGGWCATAAYAATGG-3' (SEQ ID NO:116). For enhanced amplification, two reversed primers were used, namely HPVR biotin-5'-CGTCCMARRGGAWACTGATC-3' (SEQ ID NO:117) and HPVR2 5'-GCGACCCAATGCAAATTGGT-3' (SEQ ID NO:118).

Amplification program was optimized using PE 9700 thermal cycler and the following was validated for primers SEQ ID NOs:116-118:

For PE 9700 (or MJ thermal cycler):

| | | |
|---|---|---|
| 95° C. | 5 min | |
| 95° C. | 20 sec | |
| 55° C. | 30 sec | 42 Cycles |
| 72° C. | 30 sec | |
| 72° C. | 5 min final extension | |

When using different primers or other thermal cycler, one of skill in the art would readily modify the cycling program to achieve optimal amplification efficiency.

Example 5

Genotyping for Multidrug-Resistant Tuberculosis

In one embodiment, the present invention provides a GenoFlow™ DR-MTB Array Test Kit. It is designed to detect rifampicin (RIF) and isoniazid (INH) resistant strains of *Mycobacterium Tuberculosis* (MTB) using Polymerase Chain Reaction (PCR) and "Flow-through" hybridization technology. Ten mutation probes are included for detection of drug resistant mutations in rpoB (D516V, D516G, H526D, H526Y, H526L1, S531L and S531W), katG (S315T1 and S315T2), and inhA (−15TC/T) while 5 wild-type probes are present for detection of its wild-type variant. MTB control probes are also present to ensure successful PCR reaction and amplification of rpoB, katG and inhA genes.

Primer Sequences

| Primer | Probe sequence (5'-3') | 5' Modification | SEQ ID NO |
|---|---|---|---|
| MTB-DR-Rpob-F | TCAACATCCGGCCGGTGGTC | BIOTIN | 174 |
| MTB-DR-Rpob-R | CCGGCACGCTCACGTGACAGA | BIOTIN | 175 |
| MTB-DR-KatG-F | TGGCACCGGAACCGGTAAGGA | BIOTIN | 176 |
| MTB-DR-KatG-R | CGCCAGCAGGGCTCTTCGT | | 177 |
| MTB-DR-inhA-F | AAGTTCCCGCCGGAAATCGCAG | BIOTIN | 178 |
| MTB-DR-inhA-R | CCGGTAACCAGGACTGAACGGGAT | | 179 |
| RS-IAC-F | CGAGTTCCCGCCCATAACC | | 180 |
| RS-IAC-R | GGAAGTTGCAACGCCGTCC | BIOTIN | 181 |

Probe Sequences

| Probe | Probe sequence (5'-3') | 5' Modification | SEQ ID NO |
|---|---|---|---|
| MTB-DR-Rpob-CTRL | GCTGGTGCCGAAGAA | AMINO | 182 |
| MTB-DR-KatG-CTRL | CGGGGTGTTCGTCCATAC | AMINO | 183 |
| MTB-DR-inhA-CTRL | GGTATGTCCACGAGCGTAAC | AMINO | 184 |
| MTB-DR-Rpob-WTc | GGTTGTTCTGGTCCATG | AMINO | 185 |

-continued

| Probe | Probe sequence (5'-3') | 5' Modification | SEQ ID NO |
|---|---|---|---|
| MTB-DR-Rpob-Wte | TGACCCACAAGCGCCGA | AMINO | 186 |
| MTB-DR-Rpob-Wtf | GACTGTCGGCGCTGG | AMINO | 187 |
| MTB-DR-KatG-WT | GATGCCGCTGGTGATCG | AMINO | 188 |
| MTB-DR-inhA-WT | AACCTATCGTCTCGCCG | AMINO | 189 |
| MTB-DR-Rpob-MUTc1 | GGTTGTTCTGGACCATGA | AMINO | 190 |
| MTB-DR-Rpob-MUTc2 | GGTTGTTCTGGCCCATG | AMINO | 191 |
| MTB-DR-Rpob-MUTe1 | GACCGACAAGCGCCGA | AMINO | 192 |
| MTB-DR-Rpob-MUTe2 | GCGCTTGTAGGTCAACC | AMINO | 193 |
| MTB-DR-Rpob-MUTe3 | GCGCTTGAGGGTCAAC | AMINO | 194 |
| MTB-DR-Rpob-MUTf1 | CCCCAGCGCCAACAGT | AMINO | 195 |
| MTB-DR-Rpob-MUTf2 | GACTGTGGGCGCTGG | AMINO | 196 |
| MTB-DR-KatG-MUT1 | GATGCCGGTGGTGATC | AMINO | 197 |
| MTB-DR-KatG-MUT2 | GATGCCTGTGGTGATCG | AMINO | 198 |
| MTB-DR-inhA-MUT1 | CAACCTATCATCTCGCCG | AMINO | 199 |
| RS-IAC-P | CTCGAATGCCTCGTATCAT | AMINO | 200 |

Below are some example protocols for PCR and hybridization:

| Component | Volume (μL) |
|---|---|
| PCR Master Mix | 19.6 |
| Primer Mix | 2 |
| IAC | 0.1 |
| DNA Taq Polymerase | 0.4 |
| DNase Free Water | 0.9 |
| DNA Template | 2 |
| Total | 25.00 |

| Stage | Step | Temperature (° C.) | Time |
|---|---|---|---|
| Hold | Initial denaturation | 95 | 9 min |
| 45 cycles | Denature | 95 | 20 sec |
| | Annealing | 61 | 25 sec |
| | Extension | 72 | 30 sec |
| Hold | Final Extension | 72 | 8 min |
| Hold | Final Hold | 4 | ∞ |

One Embodiment of Hybridization Protocol:

| Step | Reagent | Volume | Temp. | Time |
|---|---|---|---|---|
| Pre-hybridization | Hybridization Solution | 750 μL | 46° C. | 5 mins |
| Hybridization | Hybridization Solution + PCR Product | 520 μL (500 μL + 20 μL) | | 5 mins |
| Stringent Wash | Stringent Wash Solution | 750 μL | | ×2 times |
| Stringent Wash | Stringent Wash Solution | 750 μL | | 2 mins ×2 times |
| Adjust Device Temperature (DOWN) | | | | |
| Blocking | Blocking Solution | 500 μL | 25° C. | 5 mins |
| Enzyme Conjugation | Enzyme Conjugate | 500 μL | | 5 mins |
| Adjust Device Temperature (UP) | | | | |
| Post-reaction Wash | A Solution | 750 μL | 36° C. | ×4 times |
| Posting Blocking | Blocking Solution | 500 μL | | 1 min |
| Color Development | Detection Solution | 500 μL | | 5 mins |
| | B Solution | 750 μL | | ×3 times |
| Stop Reaction | Stop Solution | 750 μL | | 1 min |

Example 6

Beta Thalassemia Genotyping

This invention provides a system for the detection of beta-globin mutations including TATA-28 (A>G), TATA-29 (A>G), Initiation Codon (G>A), Codon 5 (−CT), Codons 8/9 (+G), Codon 15 (G>A), Codon16 (−C), Codon 17 (A>T), Codon 19 (A>G), Codon 26 (G>A) (Hb E), Codons 27/28 (+C), Codon 30 G>C, IVS1.1 (G>T), IVS1.1 (G>A), IVS1.5 (G>C), Codons 41/42 (−TCTT), Codon 43 (G>T), Codons 71/72 (+A), IVS2.1 (G>A), IVS2.654 (C>T), and 619 bp deletion.

Primer Sequences (Accession # AF007546.1):

| Primer ID | Direction | 5' Modification | Sequence (5'-->3') | SEQ ID NO |
|---|---|---|---|---|
| HBB Primer 1 | Forward | Biotin | GTACGGCTGTCATCACTTAGACCTCA | 201 |
| HBB Primer 2 | Reverse | Biotin | TTATCCCCTTCCTATGACATGAAC | 202 |
| HBB Primer 3 | Forward | Biotin | GTGTACACATATTGACCAAA | 203 |
| HBB Primer 4 | Reverse | Biotin | GCAAGAAAGCGAGCTTAG | 204 |
| HBB Primer 5 | Reverse | Biotin | GTATCTCTAAGCAAGAGAAC | 205 |

Probe Sequences (Accession # AF007546.1):

| Probe ID | Plus/Minus Strand | 5' Modification | Sequence (5'-->3') | SEQ ID NO. |
|---|---|---|---|---|
| HBB2-A1 | Sense | Amine | AGACACCATGGTGCATCTG | 206 |
| HBB2-A1a | Sense | Amine | AGACACCATGGTGCACCT | 207 |
| HBB2-A2 | Sense | Amine | CAAACAGACACCAGGGTG | 208 |
| HBB2-A3 | Sense | Amine | GCTGGGCATAAAAGTCAGG | 209 |
| HBB2-A4 | Anti-sense | Amine | CCTGACTTCTATGCCCAGC | 210 |
| HBB2-A5 | Anti-sense | Amine | CCCTGACTTTCATGCCC | 211 |
| HBB2-B1 | Sense | Amine | GCATCTGACTCCTGAGGA | 212 |
| HBB2-B1a | Sense | Amine | GCACCTGACT<u>CCT</u>GAGG | 213 |
| HBB2-B2 | Anti-sense | Amine | ACTTCTCCTCGAGTCAGAT | 214 |
| HBB2-B3 | Anti-sense | Amine | CAGGGCCTCACCACCA | 215 |
| HBB2-B4 | Sense | Amine | GTTGGTGGTAAGGCCCT | 216 |
| HBB2-B5 | Anti-sense | Amine | CCAGGGGCCTCACCA | 217 |
| HBB2-C1 | Sense | Amine | AGGAGAAGTCTGCCGTTACT | 218 |
| HBB2-C2 | Sense | Amine | AGGAGAAGGTCTGCCGTTA | 219 |
| HBB2-C3 | Sense | Amine | GAGGTTCTTTGAGTCCTTTGG | 220 |
| HBB2-C4 | Anti-sense | Amine | CAAAGGACTCAACCTCTGG | 221 |
| HBB2-D5 | Sense | Amine | CCCAGAGGTTCTTTTAGTC | 222 |
| HBB2-D1 | Sense | Amine | TGTGGGGCAAGGTGAAC | 223 |
| HBB2-D2 | Sense | Amine | CCGTTACTGCCCTGTAGG | 224 |
| HBB2-D3 | Sense | Amine | CTGTGGGGAAGGTGAAC | 225 |
| HBB2-D4 | Anti-sense | Amine | TGTGGGGCTAGGTGAACG | 226 |
| HBB2-D5 | Anti-sense | Amine | CTTCATCCACGCTCACCT | 227 |
| HBB2-E1 | Anti-sense | Amine | TGATACCAACCTGCCCAG | 228 |
| HBB2-E2 | Sense | Amine | CTGGGCAGATTGGTATCA | 229 |
| HBB2-E3 | Sense | Amine | CCCTGGGCAGTTTGGTATC | 230 |

-continued

| Probe ID | Plus/Minus Strand | 5' Modification | Sequence (5'-->3') | SEQ ID NO. |
|---|---|---|---|---|
| HBB2-E4 | Sense | Amine | GCAGGTTGCTATCAAGGTTAC | 231 |
| HBB2-E5 | Anti-sense | Amine | ATACCAACGTGCCCAGG | 232 |
| HBB2-F1 | Sense | Amine | GGTGCCTTTAGTGATGGC | 233 |
| HBB2-F2 | Sense | Amine | TCGGTGCCTTTAAGTGATG | 234 |
| HBB2-F3 | Sense | Amine | TGGGTTAAGGCAATAGCAATAT | 235 |
| HBB2-F4 | Anti-sense | Amine | ATATTGCTATTACCTTAACCC | 236 |
| HBB2-G1 | Sense | Amine | CATACCTCTTATCTTCCTCC | 237 |
| HBB2-G2 | Sense | Amine | TGTAACAAGTAGAGATTCAAGTA | 238 |
| HBB2-G3 | Sense | Amine | GAACTTCAGGGTGAGTCTAT | 239 |
| HBB2-G4 | Anti-sense | Amine | GAACTTCAGGATGAGTCTATG | 240 |

Below are some example protocols for PCR and hybridization:

| Component | Volume (μL) |
|---|---|
| PCR Premix | 19.6 |
| DNA Taq Polymerase | 0.4 |
| DNA Template | 2 to 5.0* |
| DNase Free Water | Variable |
| Total | 25.00 |

| Program | | Temperature | |
|---|---|---|---|
| Step 1 | Denature | 94° C. | 9 min |
| Step 2 | Denature | 94° C. | 1 min |
| Step 3 | Annealing | 60° C. | 30 sec |
| Step 4 | Extension | 72° C. | 30 sec |
| Step 5 | | Go to step 2 for 39 cycles (Total: 40 cycles) | |
| Step 6 | Final Extension | 72° C. | 7 min |
| Step 7 | Final Hold | 4° C. | forever |
| Step 8 | | End | |

Data Interpretation for Beta Globin Mutation:

| | Mutation points | Genotype | Type specific signal |
|---|---|---|---|
| 1 | Initiation codon T > G | $\beta^0$ | A2 |
| 2 | TATA-28 A->G | $\beta^+$ | A4 |
| 3 | TATA-29 A->G | $\beta^+$ | A5 |
| 4 | Codon 5-CT | $\beta^0$ | B3 |
| 5 | Codon 26 G->A | $\beta^+$ | B4 |
| 6 | Codons 27/28 + C | $\beta^0$ | B5 |
| 7 | Codons 8/9 + G | $\beta^0$ | C2 |
| 8 | Codons 41/42-TCTT | $\beta^0$ | C4 |
| 9 | Codon 43 G > T | $\beta^0$ | C5 |
| 10 | Codon 15 G > A | $\beta^0$ | D2 |
| 11 | Codon 16-C | $\beta^0$ | D3 |
| 12 | Codon 17 A > T | $\beta^0$ | D4 |
| 13 | Codon 19 A > G | $\beta^+$ | D5 |
| 14 | IVS1.1 G > A | $\beta^0$ | E2 |
| 15 | IVS1.1 G > T | $\beta^0$ | E3 |
| 16 | IVS 1.5 G > C | $\beta^+$ | E4 |
| 17 | Codon 30 G > C | $\beta^0$ | E5 |
| 18 | Codons 71/72 + A | $\beta^0$ | F2 |
| 19 | IVS2,654 C > T | $\beta^0$ | F4 |
| 20 | 619-bp deletion | $\beta^0$ | G2 |
| 21 | IVS2.1 G > A | $\beta^0$ | G4 |

One Embodiment of Hybridization Protocol:

| Step | Reagent | Volume | Temperature | Time |
|---|---|---|---|---|
| Pre-hybridization | Hybridization Solution | 750 μL | 52° C. | 2 mins |
| Hybridization | Hybridization Solution + PCR Product | 770 μL (750 μL + 20 μL) | | 5 mins |
| Hybridization Wash | Hybridization Solution | 750 μL | | ×4 times |
| Adjust Device Temperature (DOWN) | | | | |
| Blocking | Blocking Solution | 750 μL | 25° C. | 5 mins |
| Enzyme Conjugation | Enzyme Conjugate | 500 μL | | 5 mins |
| Adjust Device Temperature (UP) | | | | |
| Post-reaction Wash | A Solution | 750 μL | 36° C. | ×4 times |
| Blocking | Blocking Solution | 500 μL | | 1 min |
| Color Development | Detection Solution | 500 μL | | 5 mins |
| | A Solution | 750 μL | | ×3 times |
| Stop Reaction | Stop Solution | 750 μL | | 1 min |

Example 7

HBV Genotyping

Primer Sequences:

| Target | Name (R&D) | Sequence (5' → 3') | SEQ ID NO. | Modification |
|---|---|---|---|---|
| HBV | HBV-S-3F | ACGYAGCGCCTCATTTTGTG | 241 | None |
| HBV | HBV-S-3R | CACTGCATGGCCTGAGGAT | 242 | 5'-Biotin |
| IAC | IAC-R-F2 | CGAGTTCCCGCCCATAACC | 243 | None |
| IAC | IAC-R-R2 | GGAAGTTGCAACGCCGTCC | 244 | 5'-Biotin |

Probe Sequences:

| HBV Genotype | Probe Name | Sequence (5' → 3') | SEQ ID NO. | Modification |
|---|---|---|---|---|
| A | HBV-A-4 | CCACAAGCCAACCA | 245 | 5'-Amine |
| A | HBV-A2/A6-1 | CCAGCAGCCAACCA | 246 | 5'-Amine |
| B | HBV-B-5 | GCCAACTCAGAAAATC | 247 | 5'-Amine |
| B | HBV-B6-1 | GCCAACTCCGACAATC | 248 | 5'-Amine |
| C | HBV-C-4 | AGAGGCAAATCAGGTA | 249 | 5'-Amine |
| C | HBV-C-6 | AGCGGCACACCAGGTA | 250 | 5'-Amine |
| D | HBV-D-6 | CCAACAAGGACACCTG | 251 | 5'-Amine |
| D | HBV-D-7 | CCAACAAGGACCCCTG | 252 | 5'-Amine |
| E | HBV-E-4 | CCACTGGACAGAAG | 253 | 5'-Amine |
| F | HBV-F-5 | CAGACCATCAGCTGG | 254 | 5'-Amine |
| G | HBV-G-5 | GCAAATACCAACAATC | 255 | 5'-Amine |
| H | HBV-H-5 | CAACCTCGCCACCAGA | 256 | 5'-Amine |
| HBV Universal | HBV-U-4 | GTCACCATATTCTTGG | 257 | 5'-Amine |
| IAC | IAC-R-P2 | CTCGAATGCCTCGTATCAT | 258 | 5'-Amine |
| HC | Bio-HC | GTTCCAACTAGGAACATCA | 259 | 5'-Amine 3'-Biotin |
| HC | Amine-HC | GTTCCAACTAGGAACATCA | 260 | 5'-Amine |

HBV Positive Control Sequence [560 bp] (Cloned in Vector pUC57):

(SEQ ID NO: 261)
TGGGATTCTATATAAGAGGGAAACTACACGTAGCGCCTCATTTTGCGG
GTCACCATATTCTTGGGAACAAGAGCTACATCATGGGAGGTTGGTCAT
CAAAACCTCGCAAAGGCATGGGGACGAACCTTTCTGTTCCCAACCCTC
TGGGATTCTTTCCCGATCATCAGTTGGACCCTGCATTCGGAGCCAATT
CAAACAATCCAGATTGGGACTTCAACCCCATCAAGGACCACTGGCCAC
AAGCCAACCAGGTAGGAGTGGGAGCATTCGGGCCAGGGTTCACTCCCC
CACACGGAGGTGTTTTGGGGTGGAGCCCTCAGGCTCAGGGCATATTGG
CCACAGTGCCAGCAGTGCCTCCTCCTGCCTCCACCAATCGGCAGTCAG
GAAGGCAGCCTACTCCCATCTCTCCACCTCTAAGAGACAGTCATCCTC
AGGCCATGCAGTGGAATTCCACAGCTTTCCACCAAGCTCTGCAAGATC
CCAGAGTCAGGGGCCTGTATTTTCCTGCTGGTGGCTCCAGTTCAGGAA
CACTCAACCCTGTTCCAACTATTGCCTCTCAC

Internal Amplification Control Sequence [500 bp] (Cloned in Vector pUC57):

(SEQ ID NO: 262)
GAGACAGGTTCGTCCAATCCCGTGCCGCGGCCTTGGCAGGGGGTTCGC
AGGCCCCACCCGAAGCGTTGCTGAAGGCTCAGGCCTCTGAGCGACAAA
AGCTTTAAACGCGAGTTCCCGCCCATAACCTGGACCGAATGCGGGACC
ATGCATCGTTCCACTGTGTTTGTCCCATGTAGGACGGGCGCAAGGCGT
GCTTAGCTCAGCCTCGAATGCCTCGTATCATTGTGCACCCGCCGGTCA
CCAGCCAACGATGTGCGGACGGCGTTGCAACTTCCGGGGCCCAACCTG
ACCGTCCTGGGTACCGCACTCTGGGCAGTGCGAGGTAATGCCAGTCGC
CCAGTGCCGAACAACACCTGACCTAACGGTAAGAGGCTCACATAATGG

-continued

CTCCGCCGGCGCGCCCAGGGTACATTAGGTCAGCATCGGATGGACTGA

CATGAACCTTCACACCGAAGCGGAAACGGGTGCGTGGACCAGCGAGGA

GCAAACGAAAATTCCTGGCC

Below are some example protocols for PCR and hybridization:

| Component | Volume (μL) |
|---|---|
| HBV PCR Premix | 19.6 |
| IAC | 0.1 |
| DNA Taq Polymerase | 0.3 |
| DNA Template | 5.0* |
| DNase Free Water | Variable |
| Total | 25.00 |

*Suggested range of total HBV viral DNA in serum is greater than 4000 IU/mL.

| Stage | Step | Temperature (° C.) | Time |
|---|---|---|---|
| Hold | Initial denaturation | 95 | 10 min |
| 45 cycles | Denature | 95 | 30 sec |
| | Annealing | 58 | 30 sec |
| | Extension | 72 | 30 sec |
| Hold | Final Extension | 72 | 5 min |
| Hold | Final Hold | 4 | ∞ |

This thermal profile is suitable for Applied Biosystems Perkin Elmer (ABI-PE) 9600, GeneAmp PCR System 9700, Veriti (Applied Biosystems), PTC-200 (MJ Research).

One Embodiment of Hybridization Protocol:

| Step | Reagent | Volume | Temperature | Time |
|---|---|---|---|---|
| Pre-hybridization | Hybridization Solution | 750 μL | 40° C. | 2 mins |
| Hybridization | Hybridization Solution + PCR Product | 500 μL (500 μL + 20 μL) | | 5 mins |
| Hybridization Wash | Hybridization Solution | 750 μL | | ×3 times |
| Adjust Device Temperature (DOWN) | | | | |
| Blocking | Blocking Solution | 500 μL | 25° C. | 5 mins |
| Enzyme Conjugation | Enzyme Conjugate | 500 μL | | 5 mins |
| Adjust Device Temperature (UP) | | | | |
| Color Development | Detection Solution | 500 μL | 36° C. | 6 mins |
| Stop Reaction | Stop Solution | 750 μL | | 1 min |

Example 8

Genotyping for Sexually Transmitted Diseases

Primer Sequences:

| Pathogen/Target | Primer | Seq (5' to 3') | SEQ ID NO |
|---|---|---|---|
| Chlamydia trachomatis (CT) (241 + 40 bp) | P14 + CTOF2_F | GACCACAACGCTACGACGCTAATCAATGCCCGGGATTGGT | 263 |
| | P22 + CTOF2_R | TTCTGCTTGTCCGGCTACGATCCGGAGCGAGTTACGAAGA | 264 |
| Neisseria gonorrhoeae (NG) (195 + 40 bp) | P14 + NG_F2 | GACCACAACGCTACGACGCTAACGAGGCATTGAAGCAAAG | 265 |
| | P22 + NG_R2 | TTCTGCTTGTCCGGCTACGACTGCTGTTTCAAGTCGTCCA | 266 |
| HPV6/11 (289 + 40 bp) | P14 + HPV6/11F | GACCACAACGCTACGACGCTACTGTGGTAGATACCACACGC | 267 |
| | P22 + HPV6/11R | TTCTGCTTGTCCGGCTACGAACAGGTAATGGCCTGTGACTG | 268 |
| Mycoplasma genitalium (MG) (281 + 40 bp) | P14 + MG_ad_F | GACCACAACGCTACGACGCTGTTGATGAAACCTTAACCCCTTG | 269 |
| | P22 + MG_ad_R | TTCTGCTTGTCCGGCTACGAGTTGAGGGGTTTTCCATTTTTGC | 270 |
| Ureaplasma urealyticum (UU) (143 + 40 bp) | P14 + UU_F | GACCACAACGCTACGACGCTGTCAGGATCATCAAATCAATTCAC | 271 |
| | P22 + UU_R | TTCTGCTTGTCCGGCTACGACAACTTGGATAGGACGGTCA | 272 |
| Treponema pallidum (TP) (260 + 40 bp) | P14 + TP_F | GACCACAACGCTACGACGCTCAGAGCCATCAGCCCTTTTCA | 273 |
| | P22 + TP_R | TTCTGCTTGTCCGGCTACGAGAAGTTTGTCCCAGTTGCGGTT | 274 |
| Mycoplasma hominis (MH) (200 + 40 bp) | P14 + MHS1 | GACCACAACGCTACGACGCTACTCCATGAAGTCGGAATCG | 275 |
| | P22 + MHA | TTCTGCTTGTCCGGCTACGACCCACGTTCTCGTAGGGATA | 276 |
| Ureaplasma parvum (UP) (199 + 40 bp) | P14 + UMS1 | GACCACAACGCTACGACGCTGTTGGAGCTGGAATAGTTGCT | 277 |
| | P22 + UMA1 | TTCTGCTTGTCCGGCTACGACAGCTGATGTAAGTGCAGCAT | 278 |
| HSV types 1 and 2 (202 + 40 bp) | P14 + HSV1 | GACCACAACGCTACGACGCTCCACCATGTACTACAAAGACG | 279 |
| | P22 + HSV2 | TTCTGCTTGTCCGGCTACGATGGTCGTCCCGTGAAAC | 280 |
| Trichomonas vaginalis (TV) (112 + 40 bp) | Primer14 + TVK3b | GACCACAACGCTACGACGCTGTCGAACATTGGTCTTACCCTC | 281 |
| | Primer22 + TVK7b | TTCTGCTTGTCCGGCTACGATGTGCCGTCTTCAAGTATGC | 282 |
| Beta-globin (AC) (300 + 40 bp) | Primer14 + GH20F | GACCACAACGCTACGACGCTGAAGAGCCAAGGACAGGTAC | 283 |
| | Primer22 + b-455R | TTCTGCTTGTCCGGCTACGACCTTGATACCAACCTGCCCAG | 284 |
| Universal Primer | Primer14 | GACCACAACGCTACGACGCT | 285 |
| | Primer22 | TTCTGCTTGTCCGGCTACGA | 286 |

Probe Sequences:

| Pathogen/Target | Probe | Seq (5' to 3') | 5' Modification | SEQ ID NO |
|---|---|---|---|---|
| CT | CT_IN1 | AGTGCATAAACTTCTGAGG | Amine | 287 |
| NG | NG_Pr2 | TATAAACGCCCGGCAGTTAC | Amine | 288 |
| MG | MG_IN2 | AAAGATTACTGGAGAGAACC | Amine | 289 |
| UU | UU_Pr | TGAACGAAGGTAGAGAAGCA | Amine | 290 |
| UP | UMPr | TGCGGTTTACGAAATTGAAA | Amine | 291 |
| TV | TVKSp | ACTCATGACGAACGAAGAAG | Amine | 292 |
| TP | TP_IN2 | GCAGAAAAACTATCCTCAG | Amine | 293 |
| MH | MHPr | CAGCTATGCTGCGGTGAATA | Amine | 294 |
| HSV1/2 | HSV_Pr1(minus strand) | CTTGTCGATCACCTCCTCG | Amine | 295 |
| HPV6 | HPV6_IN2 | TTATGTGCATCCGTAACTA | Amine | 296 |
| HPV11 | hPV11_Pr (minus strand) | GTAGCAGATTTAGACACAGATG | Amine | 297 |
| AC | b-globin-402T | AAGGTGAACGTGGATGAAGTTGGTGG | Amine | 298 |

Below are some example protocols for PCR and hybridization:

| Component | Volume (μL) |
|---|---|
| PCR Master Mix | 18.6 |
| STD Primer Mix | 1.0 |
| DNA Taq Polymerase | 0.4 |
| STD DNA Control | up to 5.0* |
| DNase Free Water | Variable |
| Total | 25.0 |

*Suggested range of total DNA is 5 ng-100 ng.

| Stage | Step | Temperature (° C.) | Time |
|---|---|---|---|
| Hold | Initial denaturation | 95 | 10 min |
| 43 cycles | Denature | 95 | 30 sec |
|  | Annealing | 60 | 30 sec |
|  | Extension | 72 | 60 sec |
| Hold | Final Extension | 72 | 7 min |
| Hold | Final Hold | 4 | ∞ |

This thermal profile is suitable for the Veriti® Thermal Cycler (Life technologies), S1000™ Thermal Cycler (Bio-rad). A modification of the cycling program may be necessary when using other thermal cyclers (ramp rate 3° C./sec).

One Embodiment of Hybridization Protocol:

| Step | Reagent | Volume | Temperature | Incubation Time |
|---|---|---|---|---|
| Pre-hybridization | Hybridization Solution | 150 μL | 43° C. | 2 min |
| Hybridization | Hybridization Solution + PCR Product | 150 μL (+25 μL PCR product) |  | 5 min |
| Hybridization Wash | Hybridization Solution | 200 μL |  | ×3 times |

-continued

| Step | Reagent | Volume | Temperature | Incubation Time |
|---|---|---|---|---|
| Adjust Device Temperature (DOWN) | | | | |
| Blocking | Blocking Solution | 150 μL | 25° C. | 5 min |
| Enzyme Conjugation | Enzyme Conjugate | 150 μL |  | 5 min |
| Adjust Device Temperature (UP) | | | | |
| Post-reaction Wash | A Solution | 200 μL | 36° C. | ×4 times |
| Color Development | Detection Solution | 150 μL |  | 3 min |
|  | A Solution | 200 μL |  | ×3 times |
| Stop Reaction | Stop Solution | 150 μL |  | 1 min |

Example 9

Genotyping for Thrombophilia

Primer Sequences:

| Primer | Probe sequence (5'-3') | 5' Modification | SEQ ID NO |
|---|---|---|---|
| FVL_F | GAAAATGATGCCCAGTGCTT |  | 299 |
| FVL_R | TTGAAGGAAATGCCCCATTA | Biotin | 300 |
| FII_F | GAACCAATCCCGTGAAAGAA |  | 301 |
| FII_R | AGCTGCCCATGAATAGCACT | Biotin | 302 |
| MTHFR677_F | GGTTACCCCAAAGGCCACC | Biotin | 303 |
| MTHFR677_R | AAGCGGAAGAATGTGTCAGC | Biotin | 304 |
| MTHFR1298_F | TTTGGGGAGCTGAAGGACTA |  | 305 |
| MTHFR1298_R | CTTTGTGACCATTCCGGTTT | Biotin | 306 |

Probe Sequences:

| Probe | Probe sequence (5'-3') | 5' Modification | SEQ ID NO |
|---|---|---|---|
| FVL_WT | GGACAGGCGAGGAAT | AMINO | 307 |
| FVL_MUT | TGGACAGGCAAGGAAT | AMINO | 308 |
| FII_WT | TCTCAGCGAGCCTC | AMINO | 309 |
| FII_MUT | ACTCTCAGCAAGCC | AMINO | 310 |
| MTH677_WT | CGGGAGCCGATTTCA | AMINO | 311 |
| MTH677_MUT | ATGATGAAATCGACTCC | AMINO | 312 |
| MTH1298_WT | CAGTGAAGAAAGTGTCT | AMINO | 313 |
| MTH1298_MUT | GACCAGTGAAGCAAGTG | AMINO | 314 |

Below are some example protocols for PCR and hybridization:

| Component | Volume (µL) |
|---|---|
| Thrombophilia PCR Premix | 21.6 |
| Thrombophilia primer mix | 1.0 |
| DNA Taq Polymerase | 0.4 |
| DNA Template | Up to 2.0 |
| DNase Free Water | Variable |
| Total | 25.00 |

*Suggested range of total DNA is 10 ng-100 ng.

| Stage | Step | Temperature (° C.) | Time |
|---|---|---|---|
| Hold | Initial denaturation | 95 | 5 min |
| 42 cycles | Denature | 95 | 25 sec |
|  | Annealing | 55 | 30 sec |
|  | Extension | 72 | 40 sec |
| Hold | Final Extension | 72 | 8 min |
| Hold | Final Hold | 4 | ∞ |

One Embodiment of Hybridization Protocol:

| Step | Reagent | Volume | Temperature | Time |
|---|---|---|---|---|
| Pre-hybridization | Hybridization Solution | 750 µL | 41° C. | 5 mins |
| Hybridization | Hybridization Solution + PCR Product | 520 µL (500 µL + 20 µL) |  | 5 mins |
| Stringent Wash | Stringent Wash Solution | 750 µL |  | — |
| Stringent Wash | Stringent Wash Solution | 750 µL |  | 1 min ×3 times |
| Adjust Device Temperature (DOWN) |
| Blocking | Blocking Solution | 500 µL | 25° C. | 5 mins |
| Enzyme Conjugation | Enzyme Conjugate | 500 µL |  | 5 mins |
| Adjust Device Temperature (UP) |
| Post-reaction Wash | A Solution | 750 µL | 36° C. | ×4 times |
| Posting Blocking | Blocking Solution | 500 µL |  | 1 min |
| Color Development | Detection Solution | 500 µL |  | 5 mins |
|  | B Solution | 750 µL |  | ×3 times |
| Stop Reaction | Stop Solution | 750 µL |  | 1 min |

REFERENCES

1. Bunce M et al. (1995) Tissue Antigens, 46, 355-367.
2. Mach B et al. (1990) in Molecular Biology of HLA Class II Antigens, ed. Silver J (CRC, Boca Raton, Fla.), pp. 201-223.
3. Joseph Wing On Tam, "Flow Through Nucleic Acid Hybridisation Device", U.S. Pat. No. 6,020,187.
4. Thomas E D (1983) J. Clinical Oncology 1, 517-531).
5. Robinson J, Matthew J. Waller, et al., IMGT/HLA and IMGT/MHC: sequence databases for the study of the major histocompatibility complex, Nucleic Acids Res. 2003 Jan. 1; 31(1):311-4.
6. Robinson J, Waller M J, Parham P, Bodmer J G, Marsh S G., IMGT/HLA Database—a sequence database for the human major histocompatibility complex, Nucleic Acids Res. 2001 Jan. 1; 29(1):210-3.
7. Kaneshige T et. al., Rapid and Practical HLA Class II Genotyping by Reversed Dot Blotting, Transplantation Proceedings, 1993 February; 25(1): 194-198.
8. Mach et al., "DNA sequences coding for the DR beta-chain locus of the human lymphocyte antigen complex and polypeptides, diagnostic typing processes and products related thereto", U.S. Pat. No. 6,818,393, Nov. 16, 2004.
9. Chow R and Tonai R., "High throughput methods for HLA typing", U.S. Pat. No. 6,670,124, Dec. 30, 2003.
10. Chakraborty R, Stivers D N. Paternity exclusion by DNA markers: effects of paternal mutations. J Forensic Sci 1996 July; 41(4): 671-7.
11. Edwards A, Civitello A, Hammond H A, Caskey C T. DNA typing and genetic mapping with trimeric and tetrameric tandem repeats. Am J Hum Genet. 1991 October; 49(4): 746-56.
12. Gill P, Jeffreys A J, Werrett D J. Forensic application of DNA 'fingerprints'. Nature. 1985 Dec. 12-18; 318(6046): 577-9.
13. Weiss K M. In search of human variation. Genome Res 1998 July; 8(7): 691-7
14. Zhao L P, Aragaki C, Hsu L, Quiaoit F. Mapping of complex traits by single-nucleotide polymorphisms. Am J Hum Genet 1998 July; 63(1): 225-40.
15. Brightwell et al. SNP genotyping using a simple and rapid single-tube modification of ARMS illustrated by analysis 16. Munoz, N., F. X. Bosch, S. de Sanjose, R. Herrero, X. Castellsague, K. V. Shah, P. J. Snijders, and C. J. Meijer. 2003. Epidemiologic classification of human papillomavirus types associated with cervical cancer. N Engl J Med 348:518-27.
17. National Cervical Cancer Coalition. 2008. Retrieved Feb. 11, 2009. http://www.nccc-online.org
18. Anttila, A., L. von Karsa, A. Aasmaa, M. Fender, J. Patnick, M. Rebolj, F. Nicula, L. Vass, Z. Valerianova, L. Voti, C. Sauvaget, and G Ronco. 2009. Cervical cancer screening policies and coverage in Europe. Eur J Cancer 45:2649-58.
19. Human Papillomavirus: HPV Information to Clinicians, April 2007 Publication by Center Center for Disease Controland Prevention (CDC)
20. Walboomers, J. M., M. V. Jacobs, M. M. Manos, F. X. Bosch, J. A. Kummer, K. V. Shah, P. J. Snijders, J. Peto, C. J. Meijer, and N. Munoz. 1999. Human papillomavirus is a necessary cause of invasive cervical cancer worldwide. J Pathol 189:12-9.
21. Kjaer, S. K., A. J. van den Brule, G Paull, E. I. Svare, M. E. Sherman, B. L. Thomsen, M. Suntum, J. E. Bock, P. A. Poll, and C. J. Meijer. 2002. Type specific persistence of high risk human papillomavirus (HPV) as indicator of high grade cervical squamous intraepithelial lesions in young women: population based prospective follow up study. BMJ 325:572.
22. Chow, K. 2008. A membrane-based flow-through hybridization technology: a rapid and versatile tool for molecular diagnostics. The Open Biotechnology Journal 2:22-28.

What is claimed is:

1. A method for detecting the presence of multidrug-resistant *Mycobacterium tuberculosis* (DR-MTB), comprising the steps of:

(a) obtaining a sample comprising template nucleic acids;

(b) adding an internal control having the sequence of SEQ ID NO:262 into said sample, wherein said internal control is a nucleic acid that does not comprise any nucleic acid of *Mycobacterium tuberculosis;*

(c) amplifying the template nucleic acids with primers to generate amplicons, said primers have the sequences of SEQ ID NOs:174-181, wherein the primers of SEQ ID NOs:174-179 amplify nucleic acid of *Mycobacterium tuberculosis*, and the primers of SEQ ID NOs:180-181 amplify nucleic acid of the internal control of SEQ ID NO:262;

(d) hybridizing the amplicons with oligonucleotide probes to generate a hybridization profile, said probes have the sequences of SEQ ID NOs:182-200, wherein the oligonucleotide probes of SEQ ID NOs:182-199 are capable of capturing nucleic acid of *Mycobacterium tuberculosis*, and the oligonucleotide probe of SEQ ID NO:200 is capable of capturing amplicons of the internal control SEQ ID NO:262; and (e) detecting the presence of multidrug-resistant *Mycobacterium tuberculosis* from said hybridization profile.

2. The method of claim 1, wherein the primers comprise a signal generating label.

3. The method of claim 1, wherein hybridization of the amplicons with the oligonucleotide probes is carried out in a flow-through process or a lateral flow-through process.

4. The method of claim 1, wherein the method detects the presence of multidrug-resistant *Mycobacterium tuberculosis* having one or more of the following mutations:

one of seven mutations in the rpoB gene;

one of two mutations in the katG gene; and one mutation in the inhA gene.

* * * * *